(12) United States Patent
Patrick et al.

(10) Patent No.: US 12,428,470 B2
(45) Date of Patent: Sep. 30, 2025

(54) COMPOSITIONS CONTAINING ACTIVATABLE ANTIBODIES

(71) Applicant: CytomX Therapeutics, Inc., South San Francisco, CA (US)

(72) Inventors: Sarah Patrick, Menlo Park, CA (US); Claus Krebber, Palo Alto, CA (US); Sridhar Viswanathan, Menlo Park, CA (US); Shanti Gonela Duvur, Fremont, CA (US); Eric Ureno, Daly City, CA (US)

(73) Assignee: CytomX Therapeutics, Inc., South San Francisco, CA (US)

( * ) Notice: Subject to any disclaimer, the term of this patent is extended or adjusted under 35 U.S.C. 154(b) by 573 days.

(21) Appl. No.: 17/227,029

(22) Filed: Apr. 9, 2021

(65) Prior Publication Data

US 2021/0317188 A1     Oct. 14, 2021

Related U.S. Application Data

(60) Provisional application No. 63/007,776, filed on Apr. 9, 2020.

(51) Int. Cl.
C07K 16/00     (2006.01)
C07K 1/22      (2006.01)
C07K 16/28     (2006.01)

(52) U.S. Cl.
CPC ............... C07K 16/00 (2013.01); C07K 1/22 (2013.01); C07K 16/2803 (2013.01); C07K 16/2818 (2013.01); C07K 16/2827 (2013.01)

(58) Field of Classification Search
None
See application file for complete search history.

(56) References Cited

U.S. PATENT DOCUMENTS

| | | | |
|---|---|---|---|
| 7,465,790 B2 | 12/2008 | Waldmann et al. | |
| 7,541,330 B2 * | 6/2009 | Santi ................. | A61K 47/6889 424/134.1 |
| 7,666,817 B2 | 2/2010 | Daugherty et al. | |
| 7,863,426 B2 | 1/2011 | Wan et al. | |
| 7,928,205 B2 | 4/2011 | Dillon et al. | |
| 8,231,876 B2 | 7/2012 | Wan et al. | |
| 8,513,390 B2 | 8/2013 | Stagliano et al. | |
| 8,518,404 B2 | 8/2013 | Daugherty et al. | |
| 8,529,898 B2 | 9/2013 | Daugherty et al. | |
| 8,541,203 B2 | 9/2013 | Daugherty et al. | |
| 8,563,269 B2 | 10/2013 | Stagliano et al. | |
| 8,809,504 B2 | 8/2014 | Lauermann | |
| 8,883,156 B2 | 11/2014 | Wan et al. | |
| 8,895,009 B2 | 11/2014 | Wan et al. | |
| 8,906,372 B2 | 12/2014 | Wan et al. | |
| 8,916,153 B2 | 12/2014 | Wan et al. | |
| 9,096,666 B2 | 8/2015 | Wan et al. | |
| 9,102,723 B2 | 8/2015 | Wan et al. | |
| 9,169,321 B2 | 10/2015 | Daugherty et al. | |
| 9,273,132 B2 | 3/2016 | Wan et al. | |
| 9,328,165 B2 | 5/2016 | Wan et al. | |
| 9,453,078 B2 | 9/2016 | Stagliano et al. | |
| 9,913,902 B2 | 3/2018 | Wan et al. | |
| 10,059,762 B2 | 8/2018 | Stagliano et al. | |
| 10,077,300 B2 | 9/2018 | Daugherty et al. | |
| 10,118,961 B2 | 11/2018 | Stagliano et al. | |
| 10,875,913 B2 | 12/2020 | Stagliano et al. | |
| 11,028,162 B2 | 6/2021 | Daugherty et al. | |
| 11,083,792 B2 | 8/2021 | Wan et al. | |
| 2004/0109855 A1 | 6/2004 | Waldmann et al. | |
| 2009/0062142 A1 | 3/2009 | Daugherty et al. | |
| 2009/0304719 A1 | 12/2009 | Daugherty et al. | |
| 2010/0189651 A1 | 7/2010 | Stagliano et al. | |
| 2012/0149061 A1 | 6/2012 | Stagliano et al. | |
| 2012/0207756 A1 | 8/2012 | Stagliano et al. | |
| 2012/0237512 A1 | 9/2012 | Daugherty et al. | |
| 2012/0237977 A1 | 9/2012 | Daugherty et al. | |
| 2012/0244154 A1 | 9/2012 | Daugherty et al. | |
| 2013/0309230 A1 | 11/2013 | Stagliano et al. | |
| 2014/0024810 A1 | 1/2014 | Stagliano et al. | |
| 2014/0045195 A1 | 2/2014 | Daugherty et al. | |
| 2016/0083453 A1 * | 3/2016 | Hunter .................. | C07K 16/00 530/387.3 |
| 2016/0122425 A1 | 5/2016 | Daugherty et al. | |

(Continued)

FOREIGN PATENT DOCUMENTS

EP     523 503     4/2009
EP     324 771     6/2011

(Continued)

OTHER PUBLICATIONS

Schneider et al. "Tracking of antibody reduction fragments by capillary gel electrophoresis during the coupling to microparticles surface" J. Pharm. and Biomed. Analysis 53 (2010) 172-178 (Year: 2010).*
Kato et al. "Hydrophobic interaction chromatography at low salt concentration for the capture of monoclonal antibodies" J. Chromatography A, 1036 (*2004) 45-50 (Year: 2017).*
Ghosh and Wang, "Purification of humanized monoclonal antibody by hydrophobic interaction membrane chromatography" J. Chromatography A, 1107 (2006) 104-109 (Year: 2012).*
Katterle "How stable are new biologic?" Pharm Ind. 80, nr. 11, pp. 1557-1563 (2018) (Year: 2018).*

(Continued)

*Primary Examiner* — Michael Szperka
(74) *Attorney, Agent, or Firm* — Rothwell, Figg, Ernst & Manbeck, P.C.

(57) ABSTRACT

The invention provides a composition including an intact activatable antibody and a clipped variant thereof, methods of separating clipped variants of intact activatable antibodies from intact activatable antibodies and related methods including methods for determining or monitoring a relative percentage of an activatable antibody and a clipped variant thereof during a composition production process.

44 Claims, 11 Drawing Sheets
Specification includes a Sequence Listing.

(56) References Cited

U.S. PATENT DOCUMENTS

| | | | |
|---|---|---|---|
| 2016/0228546 A1 | 8/2016 | Stagliano et al. | |
| 2017/0081397 A1 | 3/2017 | Stagliano et al. | |
| 2017/0252372 A1 | 9/2017 | Weissman et al. | |
| 2017/0342395 A1 | 11/2017 | Xiang | |
| 2017/0355769 A1 | 12/2017 | Benatuil et al. | |
| 2018/0021696 A1* | 1/2018 | Wang | C07K 1/22 530/351 |
| 2018/0125972 A1 | 5/2018 | Igawa et al. | |
| 2019/0119370 A1 | 4/2019 | Stagliano et al. | |
| 2019/0211089 A1 | 7/2019 | Daugherty et al. | |
| 2019/0359714 A1* | 11/2019 | Tipton | C07K 16/2818 |
| 2021/0284721 A1 | 9/2021 | Stagliano et al. | |
| 2022/0098294 A1 | 3/2022 | Daugherty et al. | |
| 2022/0306727 A1* | 9/2022 | Cunningham | C07K 1/22 |

FOREIGN PATENT DOCUMENTS

| | | | |
|---|---|---|---|
| WO | 2002/030460 | 4/2002 | |
| WO | 2004/009638 | 1/2004 | |
| WO | 2005/042569 A1 | 5/2005 | |
| WO | WO-2006031653 A2 * | 3/2006 | A61K 47/48215 |
| WO | WO-2006122424 A1 * | 11/2006 | C07K 1/22 |
| WO | 2007/105027 | 9/2007 | |
| WO | 2009/025846 | 2/2009 | |
| WO | 2010/081173 | 7/2010 | |
| WO | 2010/096838 | 8/2010 | |
| WO | 2001/91798 | 12/2011 | |
| WO | 2012/025525 | 3/2012 | |
| WO | 2013/128194 | 9/2013 | |
| WO | 2013/163631 | 10/2013 | |
| WO | 2013/176754 A1 | 11/2013 | |
| WO | 2013/192546 | 12/2013 | |
| WO | 2013/192550 | 12/2013 | |
| WO | 2014/026136 | 2/2014 | |
| WO | 2014/052462 A2 | 4/2014 | |
| WO | 2014/107599 | 7/2014 | |
| WO | WO-2014143185 A1 * | 9/2014 | B01D 15/327 |
| WO | 2014/197612 A1 | 12/2014 | |
| WO | 2015/013671 A1 | 1/2015 | |
| WO | 2015/048329 | 4/2015 | |
| WO | 2015/066279 | 5/2015 | |
| WO | 2015/116933 | 8/2015 | |
| WO | 2016/014974 | 1/2016 | |
| WO | 2016/046778 | 3/2016 | |
| WO | 2016/118629 | 7/2016 | |
| WO | 2016/144824 | 9/2016 | |
| WO | 2016/149201 | 9/2016 | |
| WO | 2016/179003 | 11/2016 | |
| WO | 2016/179257 | 11/2016 | |
| WO | 2016/179285 | 11/2016 | |
| WO | 2016/179335 | 11/2016 | |
| WO | 2017/011580 | 1/2017 | |
| WO | 2017/025698 | 2/2017 | |
| WO | 2017/143094 | 8/2017 | |
| WO | 2017/156178 | 9/2017 | |
| WO | 2017/162587 | 9/2017 | |
| WO | 2017/214301 | 12/2017 | |
| WO | 2017/214335 | 12/2017 | |
| WO | 2017/214456 | 12/2017 | |
| WO | 2017/217930 | 12/2017 | |
| WO | 2018/011600 | 1/2018 | |
| WO | 2018/018011 | 1/2018 | |
| WO | 2018/031726 | 2/2018 | |
| WO | 2018/034885 | 2/2018 | |
| WO | 2018/039163 | 3/2018 | |
| WO | 2018/053268 | 3/2018 | |
| WO | 2018/085555 | 5/2018 | |
| WO | WO-2019018828 A1 * | 1/2019 | C07K 16/2803 |
| WO | 2019/075417 | 4/2019 | |
| WO | 2019/108733 A2 | 6/2019 | |
| WO | 2019/149281 A1 | 8/2019 | |
| WO | WO-2019152303 A1 * | 8/2019 | B01D 15/34 |
| WO | WO-2019165143 A1 * | 8/2019 | A61K 51/1027 |
| WO | 2020/252264 A1 | 12/2020 | |

OTHER PUBLICATIONS

Lu et al. "Recent advancement in application of hydrophobic interaction chromatography for aggregate removal in industrial purification process" Current Pharmaceutical Biotechnology, 2009, 10, 427-433 (Year: 2009).*

Kavoosi et al. "Strategy for selecting and characterizing linker peptides for CBM9-tagged fusion proteins expressed in *Escherichia coli*" Biotechnology and Bioengineering, 98(3), 2007 (Year: 2007).*

Aldington and Bonnerjea, "Scale-up of monoclonal antibody purification processes", J. Chromatogr. B (2007) 848(1):64-78. (doi: 10.1016/j.jchromb.2006.11.032).

Anonymous: "HIC—Hydrophobic interaction chromatography", Nov. 2, 2015 (XP055828970), URL:http://wolfson.huji.ac.il/purification/PDF/HCIC/Tosoh_HICb.pdf (Retrieved from Internet on Jul. 29, 2021), 12 pgs.

Antibody Purification, Amersham Biosciences Handbook (2008). (doi: 10.1007/978-1-4020-6754-9_908).

Boulware et al., "Evolutionary optimization of peptide substrates for proteases that exhibit rapid hydrolysis kinetics", Biotechnol. Bioeng. (2010) 106(3): 339-346.

Boyd et al., "HIC resolution of an IgG1 with an oxidized Trp in a complementarity determining region", J. Chromatogr. B (2011) 879(13-14):955-960. (doi: 10.1016/j.jchromb.2011.03.006).

Desnoyers et al., "Tumor-specific activation of an EGFR-targeting probody enhances therapeutic index", Sci. Transl. Med. (2013) 5(207):207ra144. (doi: 10.1126/scitranslmed.3006682), 11 pgs.

Evans et al., "Purification of an Fc-fusion biologic: Clearance of multiple product related impurities by hydrophobic interaction chromatography", J. Chromatogr. A (2008) 1177(2):265-271. (doi: 10.1016/j.chroma.2007.07.049).

GE Healthcare, "Hydrophobic Interaction and Reversed Phase Chromatography", (2010) Available at: www.gehealthcare.com/protein-purificationwww.gehealthcare.comGEHealthcareBio-SciencesAB, 168 pgs.

GE Healthcare, "Multimodal Chromatography", Biopharmaceutical Processing: Development, Design, and Implementation of Manufacturing Processes (2013) pp. 1-115. (doi: 10.1016/B978-0-08-100623-8.00020-7).

GE Healthcare, Capto™ Phenyl ImpRes and Capto Butyl ImpRes, (2013), 4 pgs.

GE Healthcare Life Sciences "Capto MMC ImpRes" Data file 29-0356-74AB (2015), 8 pgs.

Ghose et al., "Purification of monoclonal antibodies by hydrophobic interaction chromatography under No. salt conditions", mABS, (2013) 5(5): 795-800.

Henikoff et al., "Amino acid substitution matrices from protein blocks", Proc. Natl. Acad. Sci. USA (1992) 89(22):10915-10919.

Hyde et al., "General Principles and Strategies for Salting-Out Informed by the Hofmeister Series", Org. Process Res. Dev. (2017) 21(9):1355-1370. (doi: 10.1021/acs.oprd.7b00197).

"Hydrophobic Interaction Chromatography", ToSoh Bioscience (2018), 12 pgs.

"IgG Purity and Heterogeneity Assay Kit", SceiX Application Guide, (2018). Available at: https://sciex.com/Documents/manuals/IgG-kit-APPguide-pa800plus.pdf , 30 pgs.

Irving, "Probodies Empower a New Generation of Antibody Immunotherapies," presented at Keystone Symposia on Molecular and Cellular Biology, Feb. 2015, 25 pages.

Joshi et al., "Aggregation of Monoclonal Antibody Products: Formation and Removal", BioPharm Int. (2013) 26(3).

Kontermann and Brinkmann, "Bispecific Antibodies", Drug Discov. Today (2015) 20(7):838-847 (doi: https://doi.org/10.1016/j.drudis.2015.02.008).

Li et al., "Current Therapeutic Antibody Production and Process Optimization", BioProcess J. (2005) 5(4):8 pgs. (https://doi.org/10.12665/J54.LiZhou).

Mahmuda et al., "Monoclonal antibodies: A review of therapeutic applications and future prospects", Trop. J. Pharm. Res. (2017) 16(3):713-722. (doi: 10.4314/tjpr.v1613.29).

Murphy et al., "Technology advancements in antibody purification", Antibody Tech. J. (2016) 6:17-32. (doi: 10.2147/anti.s64762).

(56) References Cited

OTHER PUBLICATIONS

Ouellette et al., "Comparison of the in vitro and in vivo stability of a succinimide intermediate observed on a therapeutic IgG1 molecule", mAbs (2013) 5(3):432-444. (doi: 10.4161/mabs.24458).

Pace et al., "How to measure and predict the molar absorption coefficient of a protein", Protein Sci. (1995) 4(11):2411-2423. (doi: 10.1002/pro.5560041120).

Schneider et al., "Arginine and the Hofmeister Series: The Role of Ion-Ion Interactions in Protein Aggregation Suppression", J. Phys. Chem. B (2011) 115(22):7447-7458.

Tadeo et al., "Protein stabilization and the Hofmeister effect: the role of hydrophobic solvation", Biophys. J. (2009) 97(9):2595-2603. (doi: 10.1016/j.bpj.2009.08.029).

Truei et al., "Large-scale gradient elution chromatography", in Advances in Biochemical Engineering/Biotechnology (2006) 47:1-44, Springer-Verlag, Berlin-New York (1992).

Valliere-Douglass et al., "Separation and characterization of an IgG2 antibody containing a cyclic imide in CDR1 of light chain by hydrophobic interaction chromatography and mass spectrometry", Anal. Chem. (2008) 80(9):3168-3174. (doi: 10.1021/ac702245c).

Valliere-Douglass et al., "Separation of populations of antibody variants by fine tuning of hydrophobic-interaction chromatography operating conditions", J Chromatogr. A (2008) 1214(1-2):81-89. (doi: 10.1016/j.chroma.2008.10.078).

Varsha et al., "Aggregation of Monoclonal Antibody Products: Formation and Removal", BioPharm International vol. 26, Issue 3. https://www.biopharminternational.com/view/aggregation-monoclonal-antibody-products-formation-and-removal , 16 pgs.

Zhang et al., "Mixed-mode chromatography in pharmaceutical and biopharmaceutical applications", J. Pharmaceut. Biomed. (2016) 130:19-34.

Zhu et al., "Protein separation by capillary gel electrophoresis: A review", Analytica Chimica Acta (2011) 709: 21-31.

Notification of Transmittal of the International Search report and the Written Opinion of the International Searching Authority issued in PCT/US2021/026661 dated Sep. 27, 2021, 24 pgs.

International Preliminary Report on Patentability issued in PCT/US2021/026661, dated Oct. 6, 2022, 12 pgs.

Lechner, A. et al., Insights from capillary electrophoresis approaches for characterization of monoclonal antibodies and antibody drug conjugates in the period 2016-2018. Journal of Chromatography B, Aug. 1, 2019, vol. 1122-1123, pp. 1-17. (Abstract only).

International Search Report and Written Opinion for corresponding Singapore Patent Application 11202253234X dated Mar. 19, 2024. (10 pages).

Japanese Notice of Reasons for Rejection for Japanese Application No. 2022-561544 mailed Jul. 1, 2025 (19 pages).

Tang, et al.; Removal of Half Antibody, Hole-hole Homodimer and Aggregates During Bispecific Antibody Purification Using MMC ImpRes Mixed-Mode Chromatography; Protein Expression and Purification, Mar. 2020, vol. 167, No. 105529, pp. 1-11.

L. Zhang, et al.; "Mechanistic Modeling Based Process Development for Monoclonal Antibody Monomer-Aggregate Separations in Multimodal Cation Exchange Chromatography"; Journal of Chromatography A; Jun. 6, 2019, vol. 1602, pp. 317-325.

\* cited by examiner

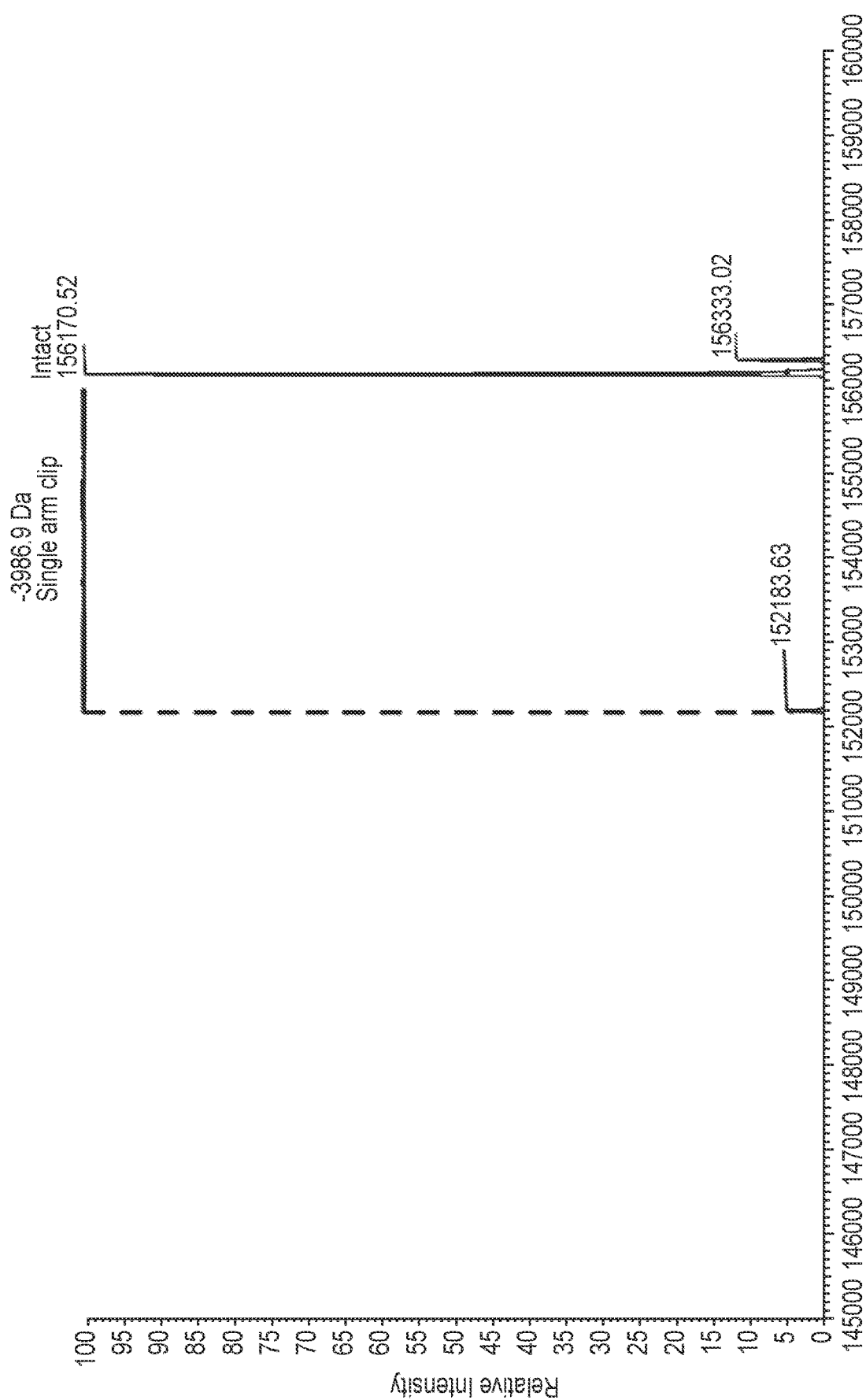

SEQUENCE LISTING

```
<160> NUMBER OF SEQ ID NOS: 315

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1
```

Leu Ser Gly Arg Ser Asp Asn His
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Thr Gly Arg Gly Pro Ser Trp Val
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic

<400> SEQUENCE: 3

Pro Leu Thr Gly Arg Ser Gly Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Thr Ala Arg Gly Pro Ser Phe Lys
1               5

<210> SEQ ID NO 5
<211> LENGTH: 12
<212> TYPE: PRT
<213> ORGANISM: Artificial Sequence
<220> FEATURE:
<223> OTHER INFORMATION: Synthetic

<400> SEQUENCE: 5

Asn Thr Leu Ser Gly Arg Ser Glu Asn His Ser Gly
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic

<400> SEQUENCE: 6

Asn Thr Leu Ser Gly Arg Ser Gly Asn His Gly Ser
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic

<400> SEQUENCE: 7

Thr Ser Thr Ser Gly Arg Ser Ala Asn Pro Arg Gly
1               5                   10

<210> SEQ ID NO 8
<211> LENGTH: 8
<212> TYPE: PRT
<213> ORGANISM: Artificial Sequence
<220> FEATURE:
<223> OTHER INFORMATION: Synthetic

<400> SEQUENCE: 8

Thr Ser Gly Arg Ser Ala Asn Pro
1               5

<210> SEQ ID NO 9
<211> LENGTH: 10
<212> TYPE: PRT
<213> ORGANISM: Artificial Sequence
<220> FEATURE:
<223> OTHER INFORMATION: Synthetic

<400> SEQUENCE: 9

Val His Met Pro Leu Gly Phe Leu Gly Pro
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Ala Val Gly Leu Leu Ala Pro Pro
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic

<400> SEQUENCE: 11

Ala Gln Asn Leu Leu Gly Met Val
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic

<400> SEQUENCE: 12

Gln Asn Gln Ala Leu Arg Met Ala
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic

<400> SEQUENCE: 13

Leu Ala Ala Pro Leu Gly Leu Leu

```
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic

<400> SEQUENCE: 14

Ser Thr Phe Pro Phe Gly Met Phe
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic

<400> SEQUENCE: 15

Ile Ser Ser Gly Leu Leu Ser Ser
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic

<400> SEQUENCE: 16

Pro Ala Gly Leu Trp Leu Asp Pro
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic

<400> SEQUENCE: 17

Val Ala Gly Arg Ser Met Arg Pro
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic

<400> SEQUENCE: 18

Val Val Pro Glu Gly Arg Arg Ser
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic

<400> SEQUENCE: 19

Ile Leu Pro Arg Ser Pro Ala Phe
1               5
```

```
<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Met Val Leu Gly Arg Ser Leu Leu
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic

<400> SEQUENCE: 21

Gln Gly Arg Ala Ile Thr Phe Ile
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Ser Pro Arg Ser Ile Met Leu Ala
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic

<400> SEQUENCE: 23

Ser Met Leu Arg Ser Met Pro Leu
1               5

<210> SEQ ID NO 24
<211> LENGTH: 13
<212> TYPE: PRT
<213> ORGANISM: Artificial Sequence
<220> FEATURE:
<223> OTHER INFORMATION: Synthetic

<400> SEQUENCE: 24

Ile Ser Ser Gly Leu Leu Ser Gly Arg Ser Asp Asn His
1               5                   10

<210> SEQ ID NO 25
<211> LENGTH: 18
<212> TYPE: PRT
<213> ORGANISM: Artificial Sequence
<220> FEATURE:
<223> OTHER INFORMATION: Synthetic

<400> SEQUENCE: 25

Ala Val Gly Leu Leu Ala Pro Pro Gly Gly Leu Ser Gly Arg Ser Asp
1               5                   10                  15
```

Asn His

<210> SEQ ID NO 26
<211> LENGTH: 22
<212> TYPE: PRT
<213> ORGANISM: Artificial Sequence
<220> FEATURE:
<223> OTHER INFORMATION: Synthetic

<400> SEQUENCE: 26

Ile Ser Ser Gly Leu Leu Ser Ser Gly Gly Ser Gly Gly Ser Leu Ser
1               5                   10                  15

Gly Arg Ser Asp Asn His
            20

<210> SEQ ID NO 27
<211> LENGTH: 8
<212> TYPE: PRT
<213> ORGANISM: Artificial Sequence
<220> FEATURE:
<223> OTHER INFORMATION: Synthetic

<400> SEQUENCE: 27

Leu Ser Gly Arg Ser Gly Asn His
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Ser Gly Arg Ser Ala Asn Pro Arg Gly
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic

<400> SEQUENCE: 29

Leu Ser Gly Arg Ser Asp Asp His
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic

<400> SEQUENCE: 30

Leu Ser Gly Arg Ser Asp Ile His
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic

<400> SEQUENCE: 31

```
Leu Ser Gly Arg Ser Asp Gln His
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic

<400> SEQUENCE: 32

Leu Ser Gly Arg Ser Asp Thr His
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic

<400> SEQUENCE: 33

Leu Ser Gly Arg Ser Asp Tyr His
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic

<400> SEQUENCE: 34

Leu Ser Gly Arg Ser Asp Asn Pro
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic

<400> SEQUENCE: 35

Leu Ser Gly Arg Ser Ala Asn Pro
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Leu Ser Gly Arg Ser Ala Asn Ile
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic

<400> SEQUENCE: 37
```

```
Leu Ser Gly Arg Ser Asp Asn Ile
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

Met Ile Ala Pro Val Ala Tyr Arg
1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic

<400> SEQUENCE: 39

Arg Pro Ser Pro Met Trp Ala Tyr
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic

<400> SEQUENCE: 40

Trp Ala Thr Pro Arg Pro Met Arg
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic

<400> SEQUENCE: 41

Phe Arg Leu Leu Asp Trp Gln Trp
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic

<400> SEQUENCE: 42

Ile Ser Ser Gly Leu
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic

<400> SEQUENCE: 43

Ile Ser Ser Gly Leu Leu Ser
```

```
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Ile Ser Ser Gly Leu Leu
1               5

<210> SEQ ID NO 45
<211> LENGTH: 15
<212> TYPE: PRT
<213> ORGANISM: Artificial Sequence
<220> FEATURE:
<223> OTHER INFORMATION: Synthetic

<400> SEQUENCE: 45

Ile Ser Ser Gly Leu Leu Ser Gly Arg Ser Ala Asn Pro Arg Gly
1               5                   10                  15

<210> SEQ ID NO 46
<211> LENGTH: 18
<212> TYPE: PRT
<213> ORGANISM: Artificial Sequence
<220> FEATURE:
<223> OTHER INFORMATION: Synthetic

<400> SEQUENCE: 46

Ala Val Gly Leu Leu Ala Pro Pro Thr Ser Gly Arg Ser Ala Asn Pro
1               5                   10                  15

Arg Gly

<210> SEQ ID NO 47
<211> LENGTH: 17
<212> TYPE: PRT
<213> ORGANISM: Artificial Sequence
<220> FEATURE:
<223> OTHER INFORMATION: Synthetic

<400> SEQUENCE: 47

Ala Val Gly Leu Leu Ala Pro Pro Ser Gly Arg Ser Ala Asn Pro Arg
1               5                   10                  15

Gly

<210> SEQ ID NO 48
<211> LENGTH: 13
<212> TYPE: PRT
<213> ORGANISM: Artificial Sequence
<220> FEATURE:
<223> OTHER INFORMATION: Synthetic

<400> SEQUENCE: 48

Ile Ser Ser Gly Leu Leu Ser Gly Arg Ser Asp Asp His
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic
```

```
<400> SEQUENCE: 49

Ile Ser Ser Gly Leu Leu Ser Gly Arg Ser Asp Ile His
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Synthetic

<400> SEQUENCE: 50

Ile Ser Ser Gly Leu Leu Ser Gly Arg Ser Asp Gln His
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Synthetic

<400> SEQUENCE: 51

Ile Ser Ser Gly Leu Leu Ser Gly Arg Ser Asp Thr His
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Synthetic

<400> SEQUENCE: 52

Ile Ser Ser Gly Leu Leu Ser Gly Arg Ser Asp Tyr His
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Synthetic

<400> SEQUENCE: 53

Ile Ser Ser Gly Leu Leu Ser Gly Arg Ser Asp Asn Pro
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Synthetic

<400> SEQUENCE: 54

Ile Ser Ser Gly Leu Leu Ser Gly Arg Ser Ala Asn Pro
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Synthetic

<400> SEQUENCE: 55
```

```
Ile Ser Ser Gly Leu Leu Ser Gly Arg Ser Ala Asn Ile
1               5                   10
```

<210> SEQ ID NO 56
<211> LENGTH: 18
<212> TYPE: PRT
<213> ORGANISM: Artificial Sequence
<220> FEATURE:
<223> OTHER INFORMATION: Synthetic

<400> SEQUENCE: 56

```
Ala Val Gly Leu Leu Ala Pro Pro Gly Gly Leu Ser Gly Arg Ser Asp
1               5                   10                  15

Asp His
```

<210> SEQ ID NO 57
<211> LENGTH: 18
<212> TYPE: PRT
<213> ORGANISM: Artificial Sequence
<220> FEATURE:
<223> OTHER INFORMATION: Synthetic

<400> SEQUENCE: 57

```
Ala Val Gly Leu Leu Ala Pro Pro Gly Gly Leu Ser Gly Arg Ser Asp
1               5                   10                  15

Ile His
```

<210> SEQ ID NO 58
<211> LENGTH: 18
<212> TYPE: PRT
<213> ORGANISM: Artificial Sequence
<220> FEATURE:
<223> OTHER INFORMATION: Synthetic

<400> SEQUENCE: 58

```
Ala Val Gly Leu Leu Ala Pro Pro Gly Gly Leu Ser Gly Arg Ser Asp
1               5                   10                  15

Gln His
```

<210> SEQ ID NO 59
<211> LENGTH: 18
<212> TYPE: PRT
<213> ORGANISM: Artificial Sequence
<220> FEATURE:
<223> OTHER INFORMATION: Synthetic

<400> SEQUENCE: 59

```
Ala Val Gly Leu Leu Ala Pro Pro Gly Gly Leu Ser Gly Arg Ser Asp
1               5                   10                  15

Thr His
```

<210> SEQ ID NO 60
<211> LENGTH: 18
<212> TYPE: PRT
<213> ORGANISM: Artificial Sequence
<220> FEATURE:
<223> OTHER INFORMATION: Synthetic

<400> SEQUENCE: 60

```
Ala Val Gly Leu Leu Ala Pro Pro Gly Gly Leu Ser Gly Arg Ser Asp
1               5                   10                  15

Tyr His
```

```
<210> SEQ ID NO 61
<211> LENGTH: 18
<212> TYPE: PRT
<213> ORGANISM: Artificial Sequence
<220> FEATURE:
<223> OTHER INFORMATION: Synthetic

<400> SEQUENCE: 61

Ala Val Gly Leu Leu Ala Pro Pro Gly Gly Leu Ser Gly Arg Ser Asp
1               5                   10                  15

Asn Pro

<210> SEQ ID NO 62
<211> LENGTH: 18
<212> TYPE: PRT
<213> ORGANISM: Artificial Sequence
<220> FEATURE:
<223> OTHER INFORMATION: Synthetic

<400> SEQUENCE: 62

Ala Val Gly Leu Leu Ala Pro Pro Gly Gly Leu Ser Gly Arg Ser Ala
1               5                   10                  15

Asn Pro

<210> SEQ ID NO 63
<211> LENGTH: 18
<212> TYPE: PRT
<213> ORGANISM: Artificial Sequence
<220> FEATURE:
<223> OTHER INFORMATION: Synthetic

<400> SEQUENCE: 63

Ala Val Gly Leu Leu Ala Pro Pro Gly Gly Leu Ser Gly Arg Ser Ala
1               5                   10                  15

Asn Ile

<210> SEQ ID NO 64
<211> LENGTH: 13
<212> TYPE: PRT
<213> ORGANISM: Artificial Sequence
<220> FEATURE:
<223> OTHER INFORMATION: Synthetic

<400> SEQUENCE: 64

Ile Ser Ser Gly Leu Leu Ser Gly Arg Ser Asp Asn Ile
1               5                   10

<210> SEQ ID NO 65
<211> LENGTH: 18
<212> TYPE: PRT
<213> ORGANISM: Artificial Sequence
<220> FEATURE:
<223> OTHER INFORMATION: Synthetic

<400> SEQUENCE: 65

Ala Val Gly Leu Leu Ala Pro Pro Gly Gly Leu Ser Gly Arg Ser Asp
1               5                   10                  15

Asn Ile

<210> SEQ ID NO 66
<211> LENGTH: 19
<212> TYPE: PRT
<213> ORGANISM: Artificial Sequence
<220> FEATURE:
```

<223> OTHER INFORMATION: Synthetic

<400> SEQUENCE: 66

Gly Leu Ser Gly Arg Ser Asp Asn His Gly Gly Ala Val Gly Leu Leu
1               5                   10                  15

Ala Pro Pro

<210> SEQ ID NO 67
<211> LENGTH: 21
<212> TYPE: PRT
<213> ORGANISM: Artificial Sequence
<220> FEATURE:
<223> OTHER INFORMATION: Synthetic

<400> SEQUENCE: 67

Gly Leu Ser Gly Arg Ser Asp Asn His Gly Gly Val His Met Pro Leu
1               5                   10                  15

Gly Phe Leu Gly Pro
            20

<210> SEQ ID NO 68
<211> LENGTH: 5
<212> TYPE: PRT
<213> ORGANISM: Artificial Sequence
<220> FEATURE:
<223> OTHER INFORMATION: Synthetic

<400> SEQUENCE: 68

Gly Ser Gly Gly Ser
1               5

<210> SEQ ID NO 69
<211> LENGTH: 4
<212> TYPE: PRT
<213> ORGANISM: Artificial Sequence
<220> FEATURE:
<223> OTHER INFORMATION: Synthetic

<400> SEQUENCE: 69

Gly Gly Gly Ser
1

<210> SEQ ID NO 70
<211> LENGTH: 4
<212> TYPE: PRT
<213> ORGANISM: Artificial Sequence
<220> FEATURE:
<223> OTHER INFORMATION: Synthetic

<400> SEQUENCE: 70

Gly Gly Ser Gly
1

<210> SEQ ID NO 71
<211> LENGTH: 5
<212> TYPE: PRT
<213> ORGANISM: Artificial Sequence
<220> FEATURE:
<223> OTHER INFORMATION: Synthetic

<400> SEQUENCE: 71

Gly Gly Ser Gly Gly
1               5

<210> SEQ ID NO 72

```
<211> LENGTH: 5
<212> TYPE: PRT
<213> ORGANISM: Artificial Sequence
<220> FEATURE:
<223> OTHER INFORMATION: Synthetic

<400> SEQUENCE: 72

Gly Ser Gly Ser Gly
1               5

<210> SEQ ID NO 73
<211> LENGTH: 5
<212> TYPE: PRT
<213> ORGANISM: Artificial Sequence
<220> FEATURE:
<223> OTHER INFORMATION: Synthetic

<400> SEQUENCE: 73

Gly Ser Gly Gly Gly
1               5

<210> SEQ ID NO 74
<211> LENGTH: 11
<212> TYPE: PRT
<213> ORGANISM: Artificial Sequence
<220> FEATURE:
<223> OTHER INFORMATION: Synthetic

<400> SEQUENCE: 74

Gly Ser Ser Gly Gly Ser Gly Gly Ser Gly Gly
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Synthetic

<400> SEQUENCE: 75

Gly Ser Ser Gly Gly Ser Gly Gly Ser Gly Gly Ser
1               5                   10

<210> SEQ ID NO 76
<211> LENGTH: 16
<212> TYPE: PRT
<213> ORGANISM: Artificial Sequence
<220> FEATURE:
<223> OTHER INFORMATION: Synthetic

<400> SEQUENCE: 76

Gly Ser Ser Gly Gly Ser Gly Gly Ser Gly Gly Ser Gly Gly Gly Ser
1               5                   10                  15

<210> SEQ ID NO 77
<211> LENGTH: 10
<212> TYPE: PRT
<213> ORGANISM: Artificial Sequence
<220> FEATURE:
<223> OTHER INFORMATION: Synthetic

<400> SEQUENCE: 77

Gly Ser Ser Gly Gly Ser Gly Gly Ser Gly
1               5                   10

<210> SEQ ID NO 78
<211> LENGTH: 11
```

```
<212> TYPE: PRT
<213> ORGANISM: Artificial Sequence
<220> FEATURE:
<223> OTHER INFORMATION: Synthetic

<400> SEQUENCE: 78

Gly Ser Ser Gly Gly Ser Gly Gly Ser Gly Ser
1               5                   10

<210> SEQ ID NO 79
<211> LENGTH: 4
<212> TYPE: PRT
<213> ORGANISM: Artificial Sequence
<220> FEATURE:
<223> OTHER INFORMATION: Synthetic

<400> SEQUENCE: 79

Gly Gly Gly Ser
1

<210> SEQ ID NO 80
<211> LENGTH: 4
<212> TYPE: PRT
<213> ORGANISM: Artificial Sequence
<220> FEATURE:
<223> OTHER INFORMATION: Synthetic

<400> SEQUENCE: 80

Gly Ser Ser Gly
1

<210> SEQ ID NO 81
<211> LENGTH: 13
<212> TYPE: PRT
<213> ORGANISM: Artificial Sequence
<220> FEATURE:
<223> OTHER INFORMATION: Synthetic

<400> SEQUENCE: 81

Gly Gly Gly Ser Ser Gly Gly Ser Gly Ser Gly Gly
1               5                   10

<210> SEQ ID NO 82
<211> LENGTH: 5
<212> TYPE: PRT
<213> ORGANISM: Artificial Sequence
<220> FEATURE:
<223> OTHER INFORMATION: Synthetic

<400> SEQUENCE: 82

Gly Gly Gly Ser Gly
1               5

<210> SEQ ID NO 83
<211> LENGTH: 5
<212> TYPE: PRT
<213> ORGANISM: Artificial Sequence
<220> FEATURE:
<223> OTHER INFORMATION: Synthetic

<400> SEQUENCE: 83

Gly Ser Ser Gly Thr
1               5

<210> SEQ ID NO 84
<211> LENGTH: 6
<212> TYPE: PRT
```

```
<213> ORGANISM: Artificial Sequence
<220> FEATURE:
<223> OTHER INFORMATION: Synthetic

<400> SEQUENCE: 84

Gln Gly Gln Ser Gly Ser
1               5

<210> SEQ ID NO 85
<211> LENGTH: 5
<212> TYPE: PRT
<213> ORGANISM: Artificial Sequence
<220> FEATURE:
<223> OTHER INFORMATION: Synthetic

<400> SEQUENCE: 85

Gly Gln Ser Gly Ser
1               5

<210> SEQ ID NO 86
<211> LENGTH: 4
<212> TYPE: PRT
<213> ORGANISM: Artificial Sequence
<220> FEATURE:
<223> OTHER INFORMATION: Synthetic

<400> SEQUENCE: 86

Gln Ser Gly Ser
1

<210> SEQ ID NO 87
<211> LENGTH: 7
<212> TYPE: PRT
<213> ORGANISM: Artificial Sequence
<220> FEATURE:
<223> OTHER INFORMATION: Synthetic

<400> SEQUENCE: 87

Gln Gly Gln Ser Gly Gln Gly
1               5

<210> SEQ ID NO 88
<211> LENGTH: 6
<212> TYPE: PRT
<213> ORGANISM: Artificial Sequence
<220> FEATURE:
<223> OTHER INFORMATION: Synthetic

<400> SEQUENCE: 88

Gly Gln Ser Gly Gln Gly
1               5

<210> SEQ ID NO 89
<211> LENGTH: 5
<212> TYPE: PRT
<213> ORGANISM: Artificial Sequence
<220> FEATURE:
<223> OTHER INFORMATION: Synthetic

<400> SEQUENCE: 89

Gln Ser Gly Gln Gly
1               5

<210> SEQ ID NO 90
<211> LENGTH: 4
<212> TYPE: PRT
<213> ORGANISM: Artificial Sequence
```

```
<220> FEATURE:
<223> OTHER INFORMATION: Synthetic

<400> SEQUENCE: 90

Ser Gly Gln Gly
1

<210> SEQ ID NO 91
<211> LENGTH: 6
<212> TYPE: PRT
<213> ORGANISM: Artificial Sequence
<220> FEATURE:
<223> OTHER INFORMATION: Synthetic

<400> SEQUENCE: 91

Gln Gly Gln Ser Gly Gln
1               5

<210> SEQ ID NO 92
<211> LENGTH: 5
<212> TYPE: PRT
<213> ORGANISM: Artificial Sequence
<220> FEATURE:
<223> OTHER INFORMATION: Synthetic

<400> SEQUENCE: 92

Gly Gln Ser Gly Gln
1               5

<210> SEQ ID NO 93
<211> LENGTH: 4
<212> TYPE: PRT
<213> ORGANISM: Artificial Sequence
<220> FEATURE:
<223> OTHER INFORMATION: Synthetic

<400> SEQUENCE: 93

Gln Ser Gly Gln
1

<210> SEQ ID NO 94
<211> LENGTH: 5
<212> TYPE: PRT
<213> ORGANISM: Artificial Sequence
<220> FEATURE:
<223> OTHER INFORMATION: Synthetic

<400> SEQUENCE: 94

Gln Gly Gln Ser Gly
1               5

<210> SEQ ID NO 95
<211> LENGTH: 4
<212> TYPE: PRT
<213> ORGANISM: Artificial Sequence
<220> FEATURE:
<223> OTHER INFORMATION: Synthetic

<400> SEQUENCE: 95

Gln Gly Gln Ser
1

<210> SEQ ID NO 96
<211> LENGTH: 16
<212> TYPE: PRT
<213> ORGANISM: Artificial Sequence
<220> FEATURE:
```

<223> OTHER INFORMATION: Synthetic

<400> SEQUENCE: 96

Arg Ser Ser Lys Ser Leu Leu His Ser Asn Gly Ile Thr Tyr Leu Tyr
1               5                   10                  15

<210> SEQ ID NO 97
<211> LENGTH: 7
<212> TYPE: PRT
<213> ORGANISM: Artificial Sequence
<220> FEATURE:
<223> OTHER INFORMATION: Synthetic

<400> SEQUENCE: 97

Gln Met Ser Asn Leu Ala Ser
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic

<400> SEQUENCE: 98

Ala Gln Asn Leu Glu Leu Pro Tyr Thr
1               5

<210> SEQ ID NO 99
<211> LENGTH: 12
<212> TYPE: PRT
<213> ORGANISM: Artificial Sequence
<220> FEATURE:
<223> OTHER INFORMATION: Synthetic

<400> SEQUENCE: 99

Gly Phe Ser Leu Ser Thr Tyr Gly Met Gly Val Gly
1               5                   10

<210> SEQ ID NO 100
<211> LENGTH: 9
<212> TYPE: PRT
<213> ORGANISM: Artificial Sequence
<220> FEATURE:
<223> OTHER INFORMATION: Synthetic

<400> SEQUENCE: 100

Asn Ile Trp Trp Ser Glu Asp Lys His
1               5

<210> SEQ ID NO 101
<211> LENGTH: 11
<212> TYPE: PRT
<213> ORGANISM: Artificial Sequence
<220> FEATURE:
<223> OTHER INFORMATION: Synthetic

<400> SEQUENCE: 101

Ile Asp Tyr Gly Asn Asp Tyr Ala Phe Thr Tyr
1               5                   10

<210> SEQ ID NO 102
<211> LENGTH: 15
<212> TYPE: PRT
<213> ORGANISM: Artificial Sequence
<220> FEATURE:
<223> OTHER INFORMATION: Synthetic

<400> SEQUENCE: 102

Leu Cys His Pro Leu Val Leu Ser Ala Trp Glu Ser Cys Ser Ser
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Synthetic

<400> SEQUENCE: 103

Leu Cys His Pro Ala Val Leu Ser Ala Trp Glu Ser Cys Ser Ser
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Synthetic

<400> SEQUENCE: 104

Leu Cys His Pro Leu Val Ala Ser Ala Trp Glu Ser Cys Ser Ser
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Synthetic

<400> SEQUENCE: 105

Leu Glu Gly Trp Cys Leu His Pro Leu Cys Leu Trp Gly Ala Gly
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Synthetic

<400> SEQUENCE: 106

Leu Cys Ala Pro Leu Val Leu Ser Ala Trp Glu Ser Cys Ser Ser
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Synthetic

<400> SEQUENCE: 107

Leu Cys His Ala Leu Val Leu Ser Ala Trp Glu Ser Cys Ser Ser
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Synthetic

```
<400> SEQUENCE: 108

Leu Cys His Pro Leu Ala Leu Ser Ala Trp Glu Ser Cys Ser Ser
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Synthetic

<400> SEQUENCE: 109

Leu Cys His Pro Leu Val Leu Ser Ala Ala Glu Ser Cys Ser Ser
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Synthetic

<400> SEQUENCE: 110

Leu Cys His Pro Leu Val Leu Ser Ala Trp Ala Ser Cys Ser Ser
1               5                   10                  15

<210> SEQ ID NO 111
<211> LENGTH: 5
<212> TYPE: PRT
<213> ORGANISM: Artificial Sequence
<220> FEATURE:
<223> OTHER INFORMATION: Synthetic

<400> SEQUENCE: 111

His Pro Leu Val Leu
1               5

<210> SEQ ID NO 112
<211> LENGTH: 15
<212> TYPE: PRT
<213> ORGANISM: Artificial Sequence
<220> FEATURE:
<223> OTHER INFORMATION: Synthetic

<400> SEQUENCE: 112

Leu Glu Gly Ala Cys Leu His Pro Leu Cys Leu Trp Gly Ala Gly
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Synthetic

<400> SEQUENCE: 113

Leu Glu Gly Trp Cys Ala His Pro Leu Cys Leu Trp Gly Ala Gly
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Synthetic

<400> SEQUENCE: 114
```

```
Leu Glu Gly Trp Cys Leu Ala Pro Leu Cys Leu Trp Gly Ala Gly
1               5                   10                  15
```

<210> SEQ ID NO 115
<211> LENGTH: 14
<212> TYPE: PRT
<213> ORGANISM: Artificial Sequence
<220> FEATURE:
<223> OTHER INFORMATION: Synthetic

<400> SEQUENCE: 115

```
Leu Glu Gly Trp Cys Leu His Ala Cys Leu Trp Gly Ala Gly
1               5                   10
```

<210> SEQ ID NO 116
<211> LENGTH: 15
<212> TYPE: PRT
<213> ORGANISM: Artificial Sequence
<220> FEATURE:
<223> OTHER INFORMATION: Synthetic

<400> SEQUENCE: 116

```
Leu Glu Gly Trp Cys Leu His Pro Ala Cys Leu Trp Gly Ala Gly
1               5                   10                  15
```

<210> SEQ ID NO 117
<211> LENGTH: 15
<212> TYPE: PRT
<213> ORGANISM: Artificial Sequence
<220> FEATURE:
<223> OTHER INFORMATION: Synthetic

<400> SEQUENCE: 117

```
Leu Glu Gly Trp Cys Leu His Pro Leu Cys Ala Trp Gly Ala Gly
1               5                   10                  15
```

<210> SEQ ID NO 118
<211> LENGTH: 15
<212> TYPE: PRT
<213> ORGANISM: Artificial Sequence
<220> FEATURE:
<223> OTHER INFORMATION: Synthetic

<400> SEQUENCE: 118

```
Leu Glu Gly Trp Cys Leu His Pro Leu Cys Leu Ala Gly Ala Gly
1               5                   10                  15
```

<210> SEQ ID NO 119
<211> LENGTH: 6
<212> TYPE: PRT
<213> ORGANISM: Artificial Sequence
<220> FEATURE:
<223> OTHER INFORMATION: Synthetic

<400> SEQUENCE: 119

```
Cys Leu His Pro Leu Cys
1               5
```

<210> SEQ ID NO 120
<211> LENGTH: 270
<212> TYPE: PRT
<213> ORGANISM: Artificial Sequence
<220> FEATURE:
<223> OTHER INFORMATION: Synthetic

<400> SEQUENCE: 120

Gln Gly Gln Ser Gly Gln Gly Leu Cys His Pro Ala Val Leu Ser Ala
1               5                   10                  15

Trp Glu Ser Cys Ser Ser Gly Gly Ser Ser Gly Gly Ser Ala Val
            20                  25                  30

Gly Leu Leu Ala Pro Pro Gly Gly Leu Ser Gly Arg Ser Asp Asn His
            35                  40                  45

Gly Gly Ser Asp Ile Val Met Thr Gln Ser Pro Leu Ser Leu Pro Val
50                  55                  60

Thr Pro Gly Glu Pro Ala Ser Ile Ser Cys Arg Ser Ser Lys Ser Leu
65                  70                  75                  80

Leu His Ser Asn Gly Ile Thr Tyr Leu Tyr Trp Tyr Leu Gln Lys Pro
                85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
            115                 120                 125

Leu Lys Ile Ser Arg Val Glu Ala Glu Asp Val Gly Val Tyr Tyr Cys
    130                 135                 140

Ala Gln Asn Leu Glu Leu Pro Tyr Thr Phe Gly Gln Gly Thr Lys Leu
145                 150                 155                 160

Glu Ile Lys Arg Thr Val Ala Ala Pro Ser Val Phe Ile Phe Pro Pro
                165                 170                 175

Ser Asp Glu Gln Leu Lys Ser Gly Thr Ala Ser Val Val Cys Leu Leu
            180                 185                 190

Asn Asn Phe Tyr Pro Arg Glu Ala Lys Val Gln Trp Lys Val Asp Asn
        195                 200                 205

Ala Leu Gln Ser Gly Asn Ser Gln Glu Ser Val Thr Glu Gln Asp Ser
    210                 215                 220

Lys Asp Ser Thr Tyr Ser Leu Ser Ser Thr Leu Thr Leu Ser Lys Ala
225                 230                 235                 240

Asp Tyr Glu Lys His Lys Val Tyr Ala Cys Glu Val Thr His Gln Gly
                245                 250                 255

Leu Ser Ser Pro Val Thr Lys Ser Phe Asn Arg Gly Glu Cys
            260                 265                 270

<210> SEQ ID NO 121
<211> LENGTH: 450
<212> TYPE: PRT
<213> ORGANISM: Artificial Sequence
<220> FEATURE:
<223> OTHER INFORMATION: Synthetic

<400> SEQUENCE: 121

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Gly Trp Ile Arg Gln Pro Pro Gly Lys Ala Leu Glu
            35                  40                  45

Trp Leu Ala Asn Ile Trp Trp Ser Glu Asp Lys His Tyr Ser Pro Ser
50                  55                  60

Leu Lys Ser Arg Leu Thr Ile Thr Lys Asp Thr Ser Lys Asn Gln Val
65                  70                  75                  80

Val Leu Thr Ile Thr Asn Val Asp Pro Val Asp Thr Ala Thr Tyr Tyr
                85                  90                  95

```
Cys Val Gln Ile Asp Tyr Gly Asn Asp Tyr Ala Phe Thr Tyr Trp Gly
                100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 122
<211> LENGTH: 451
<212> TYPE: PRT
<213> ORGANISM: Artificial Sequence
<220> FEATURE:
<223> OTHER INFORMATION: Synthetic

<400> SEQUENCE: 122
```

-continued

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Gly Trp Ile Arg Gln Pro Pro Gly Lys Ala Leu Glu
        35                  40                  45

Trp Leu Ala Asn Ile Trp Trp Ser Glu Asp Lys His Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Ile Thr Asn Val Asp Pro Val Asp Thr Ala Thr Tyr Tyr
                85                  90                  95

Cys Val Gln Ile Asp Tyr Gly Asn Asp Tyr Ala Phe Thr Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
```

```
                420                 425                 430
His Glu Ala Leu His Asn His Tyr Thr Gln Lys Ser Leu Ser Leu Ser
        435                 440                 445

Pro Gly Lys
    450

<210> SEQ ID NO 123
<211> LENGTH: 15
<212> TYPE: PRT
<213> ORGANISM: Artificial Sequence
<220> FEATURE:
<223> OTHER INFORMATION: Synthetic

<400> SEQUENCE: 123

Arg Ala Ser Glu Ser Val Asp Ala Tyr Gly Ile Ser Phe Met Asn
1               5                   10                  15

<210> SEQ ID NO 124
<211> LENGTH: 7
<212> TYPE: PRT
<213> ORGANISM: Artificial Sequence
<220> FEATURE:
<223> OTHER INFORMATION: Synthetic

<400> SEQUENCE: 124

Ala Ala Ser Asn Gln Gly Ser
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic

<400> SEQUENCE: 125

Gln Gln Ser Lys Asp Val Pro Trp Thr
1               5

<210> SEQ ID NO 126
<211> LENGTH: 10
<212> TYPE: PRT
<213> ORGANISM: Artificial Sequence
<220> FEATURE:
<223> OTHER INFORMATION: Synthetic

<400> SEQUENCE: 126

Gly Phe Thr Phe Ser Gly Tyr Ala Met Ser
1               5                   10

<210> SEQ ID NO 127
<211> LENGTH: 10
<212> TYPE: PRT
<213> ORGANISM: Artificial Sequence
<220> FEATURE:
<223> OTHER INFORMATION: Synthetic

<400> SEQUENCE: 127

Tyr Ile Ser Asn Ser Gly Gly Asn Ala His
1               5                   10

<210> SEQ ID NO 128
<211> LENGTH: 10
<212> TYPE: PRT
<213> ORGANISM: Artificial Sequence
<220> FEATURE:
```

-continued

<223> OTHER INFORMATION: Synthetic

<400> SEQUENCE: 128

Glu Asp Tyr Gly Thr Ser Pro Phe Val Tyr
1               5                   10

<210> SEQ ID NO 129
<211> LENGTH: 15
<212> TYPE: PRT
<213> ORGANISM: Artificial Sequence
<220> FEATURE:
<223> OTHER INFORMATION: Synthetic

<400> SEQUENCE: 129

Arg Ala Ser Glu Ser Val Asp Ser Tyr Gly Ile Ser Phe Met Asn
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Synthetic

<400> SEQUENCE: 130

Ala Met Ser Gly Cys Ser Trp Ser Ala Phe Cys Pro Tyr Leu Ala
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Synthetic

<400> SEQUENCE: 131

Asp Val Asn Cys Ala Ile Trp Tyr Ser Val Cys Thr Thr Val Pro
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Synthetic

<400> SEQUENCE: 132

Leu Val Cys Pro Leu Tyr Ala Leu Ser Ser Gly Val Cys Met Gly
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: Synthetic

<400> SEQUENCE: 133

Ser Val Asn Cys Arg Ile Trp Ser Ala Val Cys Ala Gly Tyr Glu
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: Synthetic

<400> SEQUENCE: 134

Met Leu Val Cys Ser Leu Gln Pro Thr Ala Met Cys Glu Arg Val
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: Synthetic

<400> SEQUENCE: 135

Ala Pro Arg Cys Tyr Met Phe Ala Ser Tyr Cys Lys Ser Gln Tyr
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Synthetic

<400> SEQUENCE: 136

Val Gly Pro Cys Glu Leu Thr Pro Lys Pro Val Cys Asn Thr Tyr
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: Synthetic

<400> SEQUENCE: 137

Glu Thr Cys Asn Gln Tyr Glu Arg Ser Ser Gly Leu Cys Phe Ala
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: Synthetic

<400> SEQUENCE: 138

Ala Pro Arg Thr Cys Tyr Thr Tyr Gln Cys Ser Ser Phe Tyr Thr
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: Synthetic

<400> SEQUENCE: 139

Gly Leu Cys Ser Trp Tyr Leu Ser Ser Ser Gly Leu Cys Val Asp
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: Synthetic

<400> SEQUENCE: 140

Val Pro Trp Cys Gln Leu Thr Pro Arg Val Met Cys Met Trp Ala
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: Synthetic

<400> SEQUENCE: 141

Asn Trp Leu Asp Cys Gln Phe Tyr Ser Glu Cys Ser Val Tyr Gly
1               5                   10                  15

<210> SEQ ID NO 142
<211> LENGTH: 15
<212> TYPE: PRT
<213> ORGANISM: Artificial Sequence
<220> FEATURE:
<223> OTHER INFORMATION: Synthetic

<400> SEQUENCE: 142

Ser Cys Pro Leu Tyr Val Met Ser Ser Phe Gly Gly Cys Trp Asp
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: Synthetic

<400> SEQUENCE: 143

Met Ser His Cys Trp Met Phe Ser Ser Cys Asp Gly Val Lys
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: Synthetic

<400> SEQUENCE: 144

Val Ser Tyr Cys Thr Trp Leu Ile Glu Val Thr Cys Leu Arg Gly
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: Synthetic

<400> SEQUENCE: 145

Val Leu Cys Ala Ala Tyr Ala Leu Ser Ser Gly Ile Cys Gly Gly
1               5                   10                  15

<210> SEQ ID NO 146
<211> LENGTH: 15
<212> TYPE: PRT
<213> ORGANISM: Artificial Sequence
<220> FEATURE:
<223> OTHER INFORMATION: Synthetic

<400> SEQUENCE: 146

Thr Thr Cys Asn Leu Tyr Gln Gln Ser Ser Met Phe Cys Asn Ala
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: Synthetic

<400> SEQUENCE: 147

Ala Pro Arg Cys Tyr Met Phe Ala Ser Tyr Cys Lys Ser Gln Tyr
1               5                   10                  15

<210> SEQ ID NO 148
<211> LENGTH: 15
<212> TYPE: PRT
<213> ORGANISM: Artificial Sequence
<220> FEATURE:
<223> OTHER INFORMATION: Synthetic

<400> SEQUENCE: 148

Pro Cys Asp Gln Asn Pro Tyr Phe Tyr Pro Tyr Val Cys His Ala
1               5                   10                  15

<210> SEQ ID NO 149
<211> LENGTH: 15
<212> TYPE: PRT
<213> ORGANISM: Artificial Sequence
<220> FEATURE:
<223> OTHER INFORMATION: Synthetic

<400> SEQUENCE: 149

Ser Val Cys Pro Met Tyr Ala Leu Ser Ser Met Leu Cys Gly Ala
1               5                   10                  15

<210> SEQ ID NO 150
<211> LENGTH: 15
<212> TYPE: PRT
<213> ORGANISM: Artificial Sequence
<220> FEATURE:
<223> OTHER INFORMATION: Synthetic

<400> SEQUENCE: 150

Leu Ser Val Glu Cys Tyr Val Phe Ser Arg Cys Ser Ser Leu Pro
1               5                   10                  15

<210> SEQ ID NO 151
<211> LENGTH: 14
<212> TYPE: PRT
<213> ORGANISM: Artificial Sequence
<220> FEATURE:
<223> OTHER INFORMATION: Synthetic

<400> SEQUENCE: 151

Phe Tyr Cys Thr Tyr Leu Val Ser Leu Thr Cys His Pro Gln
1               5                   10

<210> SEQ ID NO 152
<211> LENGTH: 6
<212> TYPE: PRT
<213> ORGANISM: Artificial Sequence
<220> FEATURE:
<223> OTHER INFORMATION: Synthetic

<400> SEQUENCE: 152

Gly Gly Gly Ser Gly Gly
1               5

<210> SEQ ID NO 153
<211> LENGTH: 6
<212> TYPE: PRT
<213> ORGANISM: Artificial Sequence
<220> FEATURE:
<223> OTHER INFORMATION: Synthetic

<400> SEQUENCE: 153

Gly Ser Gly Gly Gly Ser
1               5

<210> SEQ ID NO 154
<211> LENGTH: 6
<212> TYPE: PRT
<213> ORGANISM: Artificial Sequence
<220> FEATURE:
<223> OTHER INFORMATION: Synthetic

<400> SEQUENCE: 154

Gly Ser Gly Gly Ser Gly
1               5

<210> SEQ ID NO 155
<211> LENGTH: 15
<212> TYPE: PRT
<213> ORGANISM: Artificial Sequence
<220> FEATURE:
<223> OTHER INFORMATION: Synthetic

<400> SEQUENCE: 155

Ser Met Ala Gly Cys Gln Trp Ser Ser Phe Cys Val Gln Arg Asp
1               5                   10                  15

<210> SEQ ID NO 156
<211> LENGTH: 15
<212> TYPE: PRT
<213> ORGANISM: Artificial Sequence
<220> FEATURE:
<223> OTHER INFORMATION: Synthetic

<400> SEQUENCE: 156

Ile Tyr Ser Cys Tyr Met Phe Ala Ser Arg Cys Thr Ser Asp Lys
1               5                   10                  15

<210> SEQ ID NO 157
<211> LENGTH: 15
<212> TYPE: PRT
<213> ORGANISM: Artificial Sequence
<220> FEATURE:
<223> OTHER INFORMATION: Synthetic

<400> SEQUENCE: 157

Ser Arg Cys Ser Val Tyr Glu Val Ser Ser Gly Leu Cys Asp Trp
1               5                   10                  15

<210> SEQ ID NO 158
<211> LENGTH: 15
<212> TYPE: PRT
<213> ORGANISM: Artificial Sequence
<220> FEATURE:
<223> OTHER INFORMATION: Synthetic

<400> SEQUENCE: 158

Gly Met Cys Ser Ala Tyr Ala Tyr Ser Ser Lys Leu Cys Thr Ile

<210> SEQ ID NO 159
<211> LENGTH: 15
<212> TYPE: PRT
<213> ORGANISM: Artificial Sequence
<220> FEATURE:
<223> OTHER INFORMATION: Synthetic

<400> SEQUENCE: 159

Met Thr Thr Asn Thr Cys Asn Leu Leu Cys Gln Gln Phe Leu Thr
1               5                   10                  15

<210> SEQ ID NO 160
<211> LENGTH: 15
<212> TYPE: PRT
<213> ORGANISM: Artificial Sequence
<220> FEATURE:
<223> OTHER INFORMATION: Synthetic

<400> SEQUENCE: 160

Phe Gln Pro Cys Leu Met Phe Ala Ser Ser Cys Phe Thr Ser Lys
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: Synthetic

<400> SEQUENCE: 161

Trp Asn Cys His Pro Ala Gly Val Gly Pro Val Phe Cys Glu Val
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: Synthetic

<400> SEQUENCE: 162

Ala Leu Cys Ser Met Tyr Leu Ala Ser Ser Gly Leu Cys Asn Lys
1               5                   10                  15

<210> SEQ ID NO 163
<211> LENGTH: 15
<212> TYPE: PRT
<213> ORGANISM: Artificial Sequence
<220> FEATURE:
<223> OTHER INFORMATION: Synthetic

<400> SEQUENCE: 163

Asn Tyr Leu Ser Cys Gln Phe Phe Gln Asn Cys Tyr Glu Thr Tyr
1               5                   10                  15

<210> SEQ ID NO 164
<211> LENGTH: 15
<212> TYPE: PRT
<213> ORGANISM: Artificial Sequence
<220> FEATURE:
<223> OTHER INFORMATION: Synthetic

<400> SEQUENCE: 164

Gly Trp Cys Leu Phe Ser Asp Met Trp Leu Gly Leu Cys Ser Ala
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: Synthetic

<400> SEQUENCE: 165

Glu Phe Cys Ala Arg Asp Trp Leu Pro Tyr Gln Cys Ser Ser Phe
1               5                   10                  15

<210> SEQ ID NO 166
<211> LENGTH: 15
<212> TYPE: PRT
<213> ORGANISM: Artificial Sequence
<220> FEATURE:
<223> OTHER INFORMATION: Synthetic

<400> SEQUENCE: 166

Thr Ser Tyr Cys Ser Ile Glu His Tyr Pro Cys Asn Thr His His
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: Synthetic

<400> SEQUENCE: 167

Pro Tyr Ile Cys Ser Ser Phe Pro Leu Asp Cys Gln Ala Gly Gln
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: Synthetic

<400> SEQUENCE: 168

Val Gly Cys Glu Trp Tyr Met Ser Ser Ser Gly Met Cys Ser Arg
1               5                   10                  15

<210> SEQ ID NO 169
<211> LENGTH: 15
<212> TYPE: PRT
<213> ORGANISM: Artificial Sequence
<220> FEATURE:
<223> OTHER INFORMATION: Synthetic

<400> SEQUENCE: 169

Glu Val Cys Gly Gly Cys Ser Met Gln Ser Val Ser Cys Trp Pro
1               5                   10                  15

<210> SEQ ID NO 170
<211> LENGTH: 15
<212> TYPE: PRT
<213> ORGANISM: Artificial Sequence
<220> FEATURE:
<223> OTHER INFORMATION: Synthetic

<400> SEQUENCE: 170

Phe Thr Glu Cys Gln Leu Ser Pro Lys Ala Ile Cys Met Ser Asn
1               5                   10                  15

<210> SEQ ID NO 171
<211> LENGTH: 15
<212> TYPE: PRT
<213> ORGANISM: Artificial Sequence
<220> FEATURE:
<223> OTHER INFORMATION: Synthetic

<400> SEQUENCE: 171

```
Lys Tyr Cys Leu Phe Ser Glu Tyr Val Glu Gly Thr Cys Leu Asn
1               5                   10                  15
```

<210> SEQ ID NO 172
<211> LENGTH: 15
<212> TYPE: PRT
<213> ORGANISM: Artificial Sequence
<220> FEATURE:
<223> OTHER INFORMATION: Synthetic

<400> SEQUENCE: 172

```
Ser Gly Cys Pro Met Tyr Ala Trp Gly Trp Asp Glu Cys Trp Arg
1               5                   10                  15
```

<210> SEQ ID NO 173
<211> LENGTH: 15
<212> TYPE: PRT
<213> ORGANISM: Artificial Sequence
<220> FEATURE:
<223> OTHER INFORMATION: Synthetic

<400> SEQUENCE: 173

```
Val Asp Cys Pro Trp Tyr Ala Ser Ser Ser Ala Ile Cys Ser Arg
1               5                   10                  15
```

<210> SEQ ID NO 174
<211> LENGTH: 15
<212> TYPE: PRT
<213> ORGANISM: Artificial Sequence
<220> FEATURE:
<223> OTHER INFORMATION: Synthetic

<400> SEQUENCE: 174

```
Asp Met Leu Leu Cys Gln Ile Arg Gly Ser Cys Ala Ala Trp Gly
1               5                   10                  15
```

<210> SEQ ID NO 175
<211> LENGTH: 15
<212> TYPE: PRT
<213> ORGANISM: Artificial Sequence
<220> FEATURE:
<223> OTHER INFORMATION: Synthetic

<400> SEQUENCE: 175

```
Glu Cys His Pro Tyr Gln Ala Ser Ala Ser Leu Trp Cys Gly Tyr
1               5                   10                  15
```

<210> SEQ ID NO 176
<211> LENGTH: 15
<212> TYPE: PRT
<213> ORGANISM: Artificial Sequence
<220> FEATURE:
<223> OTHER INFORMATION: Synthetic

<400> SEQUENCE: 176

```
Met Met Met Gly Cys Met Trp Ser Ala Trp Cys Pro Pro Ser Arg
1               5                   10                  15
```

```
<210> SEQ ID NO 177
<211> LENGTH: 15
<212> TYPE: PRT
<213> ORGANISM: Artificial Sequence
<220> FEATURE:
<223> OTHER INFORMATION: Synthetic

<400> SEQUENCE: 177

Asn Ala Tyr Phe Arg Cys Ser Leu Met Cys Asn Met Ile Met Phe
1               5                   10                  15

<210> SEQ ID NO 178
<211> LENGTH: 15
<212> TYPE: PRT
<213> ORGANISM: Artificial Sequence
<220> FEATURE:
<223> OTHER INFORMATION: Synthetic

<400> SEQUENCE: 178

Ala Cys Cys Lys Glu Ser Val His Ser Val His Asp Cys Lys Arg
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: Synthetic

<400> SEQUENCE: 179

Ala Cys Ile Gly Ile Asn Ser Tyr Met Ser Asn Tyr Cys Tyr Leu
1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: Synthetic

<400> SEQUENCE: 180

Ala Asn Cys Ser Phe Leu Glu Leu Thr Asn Lys Phe Cys Thr Ile
1               5                   10                  15

<210> SEQ ID NO 181
<211> LENGTH: 15
<212> TYPE: PRT
<213> ORGANISM: Artificial Sequence
<220> FEATURE:
<223> OTHER INFORMATION: Synthetic

<400> SEQUENCE: 181

Ala Tyr Cys Ser Tyr Leu Met Phe Ala Ser Asn Pro Cys Ile Ile
1               5                   10                  15

<210> SEQ ID NO 182
<211> LENGTH: 15
<212> TYPE: PRT
<213> ORGANISM: Artificial Sequence
<220> FEATURE:
<223> OTHER INFORMATION: Synthetic

<400> SEQUENCE: 182

Cys Phe Thr Ser Lys Cys Pro Cys Leu Cys Tyr Ser Leu Leu Ala
1               5                   10                  15

<210> SEQ ID NO 183
```

```
<211> LENGTH: 15
<212> TYPE: PRT
<213> ORGANISM: Artificial Sequence
<220> FEATURE:
<223> OTHER INFORMATION: Synthetic

<400> SEQUENCE: 183

Cys Leu Cys Arg Asp Ile Asn Cys Trp Leu Gly Cys Ser Lys Thr
1               5                   10                  15

<210> SEQ ID NO 184
<211> LENGTH: 15
<212> TYPE: PRT
<213> ORGANISM: Artificial Sequence
<220> FEATURE:
<223> OTHER INFORMATION: Synthetic

<400> SEQUENCE: 184

Cys Trp Cys Asp Ile Tyr Cys Ser Pro Tyr Gln Cys Ser Ser Phe
1               5                   10                  15

<210> SEQ ID NO 185
<211> LENGTH: 15
<212> TYPE: PRT
<213> ORGANISM: Artificial Sequence
<220> FEATURE:
<223> OTHER INFORMATION: Synthetic

<400> SEQUENCE: 185

Asp Cys Ile Tyr Tyr Tyr Gln Gln Ser Ala Asn Leu Cys Ser Tyr
1               5                   10                  15

<210> SEQ ID NO 186
<211> LENGTH: 15
<212> TYPE: PRT
<213> ORGANISM: Artificial Sequence
<220> FEATURE:
<223> OTHER INFORMATION: Synthetic

<400> SEQUENCE: 186

Asp Cys Thr Gly Val Asn Tyr Tyr Ile Asp Lys His Cys Thr Asn
1               5                   10                  15

<210> SEQ ID NO 187
<211> LENGTH: 15
<212> TYPE: PRT
<213> ORGANISM: Artificial Sequence
<220> FEATURE:
<223> OTHER INFORMATION: Synthetic

<400> SEQUENCE: 187

Asp Glu Cys His Gly Tyr Leu Arg Ser Ser Gly Leu Cys Gly Gly
1               5                   10                  15

<210> SEQ ID NO 188
<211> LENGTH: 15
<212> TYPE: PRT
<213> ORGANISM: Artificial Sequence
<220> FEATURE:
<223> OTHER INFORMATION: Synthetic

<400> SEQUENCE: 188

Asp Ile Cys Ser Ala Tyr Ala Ala Ser Gly Phe Cys Tyr Tyr
1               5                   10                  15

<210> SEQ ID NO 189
<211> LENGTH: 15
```

```
<212> TYPE: PRT
<213> ORGANISM: Artificial Sequence
<220> FEATURE:
<223> OTHER INFORMATION: Synthetic

<400> SEQUENCE: 189

Asp Ile Ile Cys Val Leu Thr Pro Thr Ala Trp Cys Gly Arg Thr
1               5                   10                  15

<210> SEQ ID NO 190
<211> LENGTH: 15
<212> TYPE: PRT
<213> ORGANISM: Artificial Sequence
<220> FEATURE:
<223> OTHER INFORMATION: Synthetic

<400> SEQUENCE: 190

Asp Asn Cys Cys Met Tyr Cys Ser Trp Trp Ile Ala Cys Arg Asp
1               5                   10                  15

<210> SEQ ID NO 191
<211> LENGTH: 15
<212> TYPE: PRT
<213> ORGANISM: Artificial Sequence
<220> FEATURE:
<223> OTHER INFORMATION: Synthetic

<400> SEQUENCE: 191

Asp Ser Cys Gln Trp Tyr Met Leu Ser Ala Asp Leu Cys Gly Thr
1               5                   10                  15

<210> SEQ ID NO 192
<211> LENGTH: 15
<212> TYPE: PRT
<213> ORGANISM: Artificial Sequence
<220> FEATURE:
<223> OTHER INFORMATION: Synthetic

<400> SEQUENCE: 192

Asp Ser Val Cys Phe Ser Ser Ser Phe Leu Cys His Lys Ser
1               5                   10                  15

<210> SEQ ID NO 193
<211> LENGTH: 15
<212> TYPE: PRT
<213> ORGANISM: Artificial Sequence
<220> FEATURE:
<223> OTHER INFORMATION: Synthetic

<400> SEQUENCE: 193

Asp Thr Met Cys Ala Ile Trp Trp Thr Val Cys Ser Gly Gly Arg
1               5                   10                  15

<210> SEQ ID NO 194
<211> LENGTH: 15
<212> TYPE: PRT
<213> ORGANISM: Artificial Sequence
<220> FEATURE:
<223> OTHER INFORMATION: Synthetic

<400> SEQUENCE: 194

Glu Cys Thr Tyr Gln Thr Ser Ser Phe His Glu Ala Cys Met Ser
1               5                   10                  15

<210> SEQ ID NO 195
<211> LENGTH: 15
<212> TYPE: PRT
```

```
<213> ORGANISM: Artificial Sequence
<220> FEATURE:
<223> OTHER INFORMATION: Synthetic

<400> SEQUENCE: 195

Glu Gly Cys Asn Leu Tyr Glu Arg Ser Ser Tyr Gly Cys Asn Asn
1               5                   10                  15

<210> SEQ ID NO 196
<211> LENGTH: 15
<212> TYPE: PRT
<213> ORGANISM: Artificial Sequence
<220> FEATURE:
<223> OTHER INFORMATION: Synthetic

<400> SEQUENCE: 196

Glu Gly Cys Thr Ala Phe Ala Met Ser Ala Gly Ile Cys Gly Gly
1               5                   10                  15

<210> SEQ ID NO 197
<211> LENGTH: 15
<212> TYPE: PRT
<213> ORGANISM: Artificial Sequence
<220> FEATURE:
<223> OTHER INFORMATION: Synthetic

<400> SEQUENCE: 197

Glu Gln Ser Cys Ser Leu Thr Pro Ile Ala Phe Cys Trp Ser Glu
1               5                   10                  15

<210> SEQ ID NO 198
<211> LENGTH: 15
<212> TYPE: PRT
<213> ORGANISM: Artificial Sequence
<220> FEATURE:
<223> OTHER INFORMATION: Synthetic

<400> SEQUENCE: 198

Glu Trp Cys Asn Ala Tyr Ile Ser Ser Ser Lys Leu Cys Ser Thr
1               5                   10                  15

<210> SEQ ID NO 199
<211> LENGTH: 15
<212> TYPE: PRT
<213> ORGANISM: Artificial Sequence
<220> FEATURE:
<223> OTHER INFORMATION: Synthetic

<400> SEQUENCE: 199

Phe Glu Val Cys Tyr Met Phe Ala Ser Ala Cys Arg Asn Gly Met
1               5                   10                  15

<210> SEQ ID NO 200
<211> LENGTH: 15
<212> TYPE: PRT
<213> ORGANISM: Artificial Sequence
<220> FEATURE:
<223> OTHER INFORMATION: Synthetic

<400> SEQUENCE: 200

Phe Ser Cys Ser Trp Tyr Ala Glu Ser Ser Leu Cys Asp Ile
1               5                   10                  15

<210> SEQ ID NO 201
<211> LENGTH: 15
<212> TYPE: PRT
<213> ORGANISM: Artificial Sequence
```

```
<220> FEATURE:
<223> OTHER INFORMATION: Synthetic

<400> SEQUENCE: 201

Phe Val Cys Gln Met Phe Glu Ala Ser Ser Gly Leu Cys Gly Gly
1               5                   10                  15

<210> SEQ ID NO 202
<211> LENGTH: 15
<212> TYPE: PRT
<213> ORGANISM: Artificial Sequence
<220> FEATURE:
<223> OTHER INFORMATION: Synthetic

<400> SEQUENCE: 202

Phe Tyr Cys Pro Cys Cys Met Phe Ala Ser Ser Cys Gly Ser Arg
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: Synthetic

<400> SEQUENCE: 203

Phe Tyr Cys Ser Tyr Leu Pro Gly Ala Ser His Gln Cys Ser His
1               5                   10                  15

<210> SEQ ID NO 204
<211> LENGTH: 15
<212> TYPE: PRT
<213> ORGANISM: Artificial Sequence
<220> FEATURE:
<223> OTHER INFORMATION: Synthetic

<400> SEQUENCE: 204

Phe Tyr Cys Ser Tyr Leu Tyr Met Cys Glu Val Cys Cys Tyr Glu
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: Synthetic

<400> SEQUENCE: 205

Gly Phe Cys Thr Gln His Thr Val Leu Thr Trp Cys Pro Thr Ser
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: Synthetic

<400> SEQUENCE: 206

Gly Ser Cys Pro Ser Tyr Ala Val Ser Ala Gly Leu Cys Tyr Ala
1               5                   10                  15

<210> SEQ ID NO 207
<211> LENGTH: 15
<212> TYPE: PRT
<213> ORGANISM: Artificial Sequence
<220> FEATURE:
```

<223> OTHER INFORMATION: Synthetic

<400> SEQUENCE: 207

Gly Ser Gln Cys Phe Leu Thr Pro Thr Ala Phe Cys Thr His Thr
1               5                   10                  15

<210> SEQ ID NO 208
<211> LENGTH: 15
<212> TYPE: PRT
<213> ORGANISM: Artificial Sequence
<220> FEATURE:
<223> OTHER INFORMATION: Synthetic

<400> SEQUENCE: 208

Gly Thr Cys His Pro Tyr Met Gln Ser Ser Lys Ile Cys Asn Asn
1               5                   10                  15

<210> SEQ ID NO 209
<211> LENGTH: 15
<212> TYPE: PRT
<213> ORGANISM: Artificial Sequence
<220> FEATURE:
<223> OTHER INFORMATION: Synthetic

<400> SEQUENCE: 209

Gly Val Glu Cys Phe Val Phe Thr Gly Gly Cys Gly Gly Tyr Gly
1               5                   10                  15

<210> SEQ ID NO 210
<211> LENGTH: 15
<212> TYPE: PRT
<213> ORGANISM: Artificial Sequence
<220> FEATURE:
<223> OTHER INFORMATION: Synthetic

<400> SEQUENCE: 210

His Glu Leu Cys Asn Gly His Trp Val Pro Cys Cys Trp Ala Tyr
1               5                   10                  15

<210> SEQ ID NO 211
<211> LENGTH: 15
<212> TYPE: PRT
<213> ORGANISM: Artificial Sequence
<220> FEATURE:
<223> OTHER INFORMATION: Synthetic

<400> SEQUENCE: 211

Ile Cys Asp Ser Tyr Tyr Ala Val Ser Ser Gly Leu Cys Leu Leu
1               5                   10                  15

<210> SEQ ID NO 212
<211> LENGTH: 15
<212> TYPE: PRT
<213> ORGANISM: Artificial Sequence
<220> FEATURE:
<223> OTHER INFORMATION: Synthetic

<400> SEQUENCE: 212

Ile Gly Cys Ala Trp Tyr Val Ser Ser Ala Gly Trp Cys Ser Pro
1               5                   10                  15

<210> SEQ ID NO 213
<211> LENGTH: 15
<212> TYPE: PRT
<213> ORGANISM: Artificial Sequence
<220> FEATURE:
<223> OTHER INFORMATION: Synthetic

<400> SEQUENCE: 213

Ile Asn Leu Cys Trp Met Phe Ala Ser Glu Cys Gly Glu His His
1               5                   10                  15

<210> SEQ ID NO 214
<211> LENGTH: 15
<212> TYPE: PRT
<213> ORGANISM: Artificial Sequence
<220> FEATURE:
<223> OTHER INFORMATION: Synthetic

<400> SEQUENCE: 214

Lys Cys Trp Leu Ala Glu Met Thr Asn Leu Glu His Cys Asn Met
1               5                   10                  15

<210> SEQ ID NO 215
<211> LENGTH: 15
<212> TYPE: PRT
<213> ORGANISM: Artificial Sequence
<220> FEATURE:
<223> OTHER INFORMATION: Synthetic

<400> SEQUENCE: 215

Lys His Cys Ser Asp Phe Ala Tyr Ser Ser Arg Leu Cys Asp Arg
1               5                   10                  15

<210> SEQ ID NO 216
<211> LENGTH: 15
<212> TYPE: PRT
<213> ORGANISM: Artificial Sequence
<220> FEATURE:
<223> OTHER INFORMATION: Synthetic

<400> SEQUENCE: 216

Lys Val Cys Ser Ser Tyr Ala Ser Ser Ser Gly Leu Cys Gly Trp
1               5                   10                  15

<210> SEQ ID NO 217
<211> LENGTH: 15
<212> TYPE: PRT
<213> ORGANISM: Artificial Sequence
<220> FEATURE:
<223> OTHER INFORMATION: Synthetic

<400> SEQUENCE: 217

Leu Asp Ser Cys Tyr Met Phe Ala Ser Tyr Cys Val Gln Ala Val
1               5                   10                  15

<210> SEQ ID NO 218
<211> LENGTH: 15
<212> TYPE: PRT
<213> ORGANISM: Artificial Sequence
<220> FEATURE:
<223> OTHER INFORMATION: Synthetic

<400> SEQUENCE: 218

Leu Leu Ala Cys His Pro Ile Phe Val Thr Val Cys Gln Thr Arg
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: Synthetic

```
<400> SEQUENCE: 219

Leu Leu Ser Cys Pro Tyr Asn Pro Glu His Val Cys His Thr Ser
1               5                   10                  15

<210> SEQ ID NO 220
<211> LENGTH: 15
<212> TYPE: PRT
<213> ORGANISM: Artificial Sequence
<220> FEATURE:
<223> OTHER INFORMATION: Synthetic

<400> SEQUENCE: 220

Leu Met Cys Ser Leu Tyr Ala Leu Ser Ser Asn Leu Cys Gly Arg
1               5                   10                  15

<210> SEQ ID NO 221
<211> LENGTH: 15
<212> TYPE: PRT
<213> ORGANISM: Artificial Sequence
<220> FEATURE:
<223> OTHER INFORMATION: Synthetic

<400> SEQUENCE: 221

Leu Met Trp Cys Val Leu Phe Leu Trp Ser Trp Cys Cys Arg Ile
1               5                   10                  15

<210> SEQ ID NO 222
<211> LENGTH: 15
<212> TYPE: PRT
<213> ORGANISM: Artificial Sequence
<220> FEATURE:
<223> OTHER INFORMATION: Synthetic

<400> SEQUENCE: 222

Leu Pro Ile Cys His Leu Thr Pro Thr Ala Val Cys Thr His Ile
1               5                   10                  15

<210> SEQ ID NO 223
<211> LENGTH: 15
<212> TYPE: PRT
<213> ORGANISM: Artificial Sequence
<220> FEATURE:
<223> OTHER INFORMATION: Synthetic

<400> SEQUENCE: 223

Leu Ser Asn Met Cys Leu Ala Phe Gly Ser Cys Leu Tyr Ala Trp
1               5                   10                  15

<210> SEQ ID NO 224
<211> LENGTH: 15
<212> TYPE: PRT
<213> ORGANISM: Artificial Sequence
<220> FEATURE:
<223> OTHER INFORMATION: Synthetic

<400> SEQUENCE: 224

Leu Ser Arg Cys His Pro Ile Trp Tyr Thr Ile Cys Gln Asn Pro
1               5                   10                  15

<210> SEQ ID NO 225
<211> LENGTH: 15
<212> TYPE: PRT
<213> ORGANISM: Artificial Sequence
<220> FEATURE:
<223> OTHER INFORMATION: Synthetic

<400> SEQUENCE: 225
```

```
Leu Thr Gln Cys Met Ser Val His Lys Glu Cys Gly Gly Tyr Glu
1               5                   10                  15

<210> SEQ ID NO 226
<211> LENGTH: 15
<212> TYPE: PRT
<213> ORGANISM: Artificial Sequence
<220> FEATURE:
<223> OTHER INFORMATION: Synthetic

<400> SEQUENCE: 226

Leu Val Asn Cys Arg Ile Trp Ser Trp Val Cys Glu Glu Ala Thr
1               5                   10                  15

<210> SEQ ID NO 227
<211> LENGTH: 15
<212> TYPE: PRT
<213> ORGANISM: Artificial Sequence
<220> FEATURE:
<223> OTHER INFORMATION: Synthetic

<400> SEQUENCE: 227

Leu Tyr Cys Ser Trp Tyr Gln Met Ser Ser Ala Val Cys Lys Glu
1               5                   10                  15

<210> SEQ ID NO 228
<211> LENGTH: 15
<212> TYPE: PRT
<213> ORGANISM: Artificial Sequence
<220> FEATURE:
<223> OTHER INFORMATION: Synthetic

<400> SEQUENCE: 228

Met Glu Cys Gly Trp Tyr Ala Leu Ser Ala Arg Phe Cys Glu Val
1               5                   10                  15

<210> SEQ ID NO 229
<211> LENGTH: 15
<212> TYPE: PRT
<213> ORGANISM: Artificial Sequence
<220> FEATURE:
<223> OTHER INFORMATION: Synthetic

<400> SEQUENCE: 229

Met Thr Cys Ser Pro Tyr Ala Met Ser Ala His Phe Cys Asn Glu
1               5                   10                  15

<210> SEQ ID NO 230
<211> LENGTH: 15
<212> TYPE: PRT
<213> ORGANISM: Artificial Sequence
<220> FEATURE:
<223> OTHER INFORMATION: Synthetic

<400> SEQUENCE: 230

Met Val Cys Ser Leu Tyr Ala Tyr Ser Ala Ser Leu Cys Gly Ala
1               5                   10                  15

<210> SEQ ID NO 231
<211> LENGTH: 15
<212> TYPE: PRT
<213> ORGANISM: Artificial Sequence
<220> FEATURE:
<223> OTHER INFORMATION: Synthetic

<400> SEQUENCE: 231
```

Asn Ala Leu Cys Trp Ser Thr Phe Ser Trp Trp Cys Asp Met Asp
1               5                   10                  15

<210> SEQ ID NO 232
<211> LENGTH: 15
<212> TYPE: PRT
<213> ORGANISM: Artificial Sequence
<220> FEATURE:
<223> OTHER INFORMATION: Synthetic

<400> SEQUENCE: 232

Asn Phe Thr Cys Met Leu Thr Pro Lys Ala Tyr Cys Val Gln Thr
1               5                   10                  15

<210> SEQ ID NO 233
<211> LENGTH: 15
<212> TYPE: PRT
<213> ORGANISM: Artificial Sequence
<220> FEATURE:
<223> OTHER INFORMATION: Synthetic

<400> SEQUENCE: 233

Asn Gly Ala Cys Ile Phe Thr Leu Ser Trp Cys Thr Asn Lys Thr
1               5                   10                  15

<210> SEQ ID NO 234
<211> LENGTH: 15
<212> TYPE: PRT
<213> ORGANISM: Artificial Sequence
<220> FEATURE:
<223> OTHER INFORMATION: Synthetic

<400> SEQUENCE: 234

Asn Gly Cys Glu Leu Tyr Ala Ala Ala Ser Gly Leu Cys Arg Thr
1               5                   10                  15

<210> SEQ ID NO 235
<211> LENGTH: 15
<212> TYPE: PRT
<213> ORGANISM: Artificial Sequence
<220> FEATURE:
<223> OTHER INFORMATION: Synthetic

<400> SEQUENCE: 235

Asn Ile Glu Cys Ser Val Phe Gly Arg Cys Cys Cys Asp Asn Tyr
1               5                   10                  15

<210> SEQ ID NO 236
<211> LENGTH: 15
<212> TYPE: PRT
<213> ORGANISM: Artificial Sequence
<220> FEATURE:
<223> OTHER INFORMATION: Synthetic

<400> SEQUENCE: 236

Pro Ala Cys Arg Pro Met Phe Trp Asn Arg Ser Cys Asp Asn Ile
1               5                   10                  15

<210> SEQ ID NO 237
<211> LENGTH: 15
<212> TYPE: PRT
<213> ORGANISM: Artificial Sequence
<220> FEATURE:
<223> OTHER INFORMATION: Synthetic

<400> SEQUENCE: 237

Pro Cys Arg Val Ser Asn Met Phe Phe Pro Tyr Asn Cys Leu Asp

-continued

```
<210> SEQ ID NO 238
<211> LENGTH: 15
<212> TYPE: PRT
<213> ORGANISM: Artificial Sequence
<220> FEATURE:
<223> OTHER INFORMATION: Synthetic

<400> SEQUENCE: 238

Pro Ile Met Cys Met Leu Leu Pro Glu Ser Tyr Cys Trp Ile Trp
1               5                   10                  15

<210> SEQ ID NO 239
<211> LENGTH: 15
<212> TYPE: PRT
<213> ORGANISM: Artificial Sequence
<220> FEATURE:
<223> OTHER INFORMATION: Synthetic

<400> SEQUENCE: 239

Pro Gln Ser Cys Tyr Met Phe Ala Ser Leu Cys Met Pro Asn Gly
1               5                   10                  15

<210> SEQ ID NO 240
<211> LENGTH: 15
<212> TYPE: PRT
<213> ORGANISM: Artificial Sequence
<220> FEATURE:
<223> OTHER INFORMATION: Synthetic

<400> SEQUENCE: 240

Pro Arg Cys Pro Gln Gly Leu Pro Leu Tyr Gln Cys Ser Ser Phe
1               5                   10                  15

<210> SEQ ID NO 241
<211> LENGTH: 15
<212> TYPE: PRT
<213> ORGANISM: Artificial Sequence
<220> FEATURE:
<223> OTHER INFORMATION: Synthetic

<400> SEQUENCE: 241

Pro Ser Val Glu Cys Leu Val Phe Lys Arg Cys Tyr Ala Leu Pro
1               5                   10                  15

<210> SEQ ID NO 242
<211> LENGTH: 15
<212> TYPE: PRT
<213> ORGANISM: Artificial Sequence
<220> FEATURE:
<223> OTHER INFORMATION: Synthetic

<400> SEQUENCE: 242

Pro Val Cys Gln Arg Ser Ala Thr Ile Tyr Asn Cys Asn Trp Phe
1               5                   10                  15

<210> SEQ ID NO 243
<211> LENGTH: 15
<212> TYPE: PRT
<213> ORGANISM: Artificial Sequence
<220> FEATURE:
<223> OTHER INFORMATION: Synthetic

<400> SEQUENCE: 243

Gln Cys Ala Ala Tyr Tyr Ile Ser Ser Phe Gly Gly Cys Ser Asn
1               5                   10                  15
```

```
<210> SEQ ID NO 244
<211> LENGTH: 15
<212> TYPE: PRT
<213> ORGANISM: Artificial Sequence
<220> FEATURE:
<223> OTHER INFORMATION: Synthetic

<400> SEQUENCE: 244

Gln Phe Gly Cys Phe Met Leu Ala Arg Asp Phe Cys Gly Thr Tyr
1               5                   10                  15

<210> SEQ ID NO 245
<211> LENGTH: 15
<212> TYPE: PRT
<213> ORGANISM: Artificial Sequence
<220> FEATURE:
<223> OTHER INFORMATION: Synthetic

<400> SEQUENCE: 245

Gln Met Met Cys Pro Tyr Asn Pro Glu His Lys Cys His Gln Lys
1               5                   10                  15

<210> SEQ ID NO 246
<211> LENGTH: 15
<212> TYPE: PRT
<213> ORGANISM: Artificial Sequence
<220> FEATURE:
<223> OTHER INFORMATION: Synthetic

<400> SEQUENCE: 246

Gln Arg Glu Cys Trp Met Phe Ala Ser Ser Cys Asn Ser Lys Asn
1               5                   10                  15

<210> SEQ ID NO 247
<211> LENGTH: 15
<212> TYPE: PRT
<213> ORGANISM: Artificial Sequence
<220> FEATURE:
<223> OTHER INFORMATION: Synthetic

<400> SEQUENCE: 247

Gln Ser Asn Met Cys Thr Thr Tyr Ile Cys Ser Ser Phe Asn Tyr
1               5                   10                  15

<210> SEQ ID NO 248
<211> LENGTH: 15
<212> TYPE: PRT
<213> ORGANISM: Artificial Sequence
<220> FEATURE:
<223> OTHER INFORMATION: Synthetic

<400> SEQUENCE: 248

Gln Ser Arg Cys His Ser Leu Ala Pro Tyr Leu Cys Ser Ser Phe
1               5                   10                  15

<210> SEQ ID NO 249
<211> LENGTH: 15
<212> TYPE: PRT
<213> ORGANISM: Artificial Sequence
<220> FEATURE:
<223> OTHER INFORMATION: Synthetic

<400> SEQUENCE: 249

Arg Ala Tyr Cys Ser Leu Leu Phe Ala Asp Ser Cys Asn Asn Asn
1               5                   10                  15
```

```
<210> SEQ ID NO 250
<211> LENGTH: 15
<212> TYPE: PRT
<213> ORGANISM: Artificial Sequence
<220> FEATURE:
<223> OTHER INFORMATION: Synthetic

<400> SEQUENCE: 250

Arg Cys Ile Gly Ile Asn Gln Tyr Ile Asp Ser Asn Cys Tyr Asn
1               5                   10                  15

<210> SEQ ID NO 251
<211> LENGTH: 15
<212> TYPE: PRT
<213> ORGANISM: Artificial Sequence
<220> FEATURE:
<223> OTHER INFORMATION: Synthetic

<400> SEQUENCE: 251

Arg Leu Ser Cys Phe Met Phe Ala Ser Gln Cys Ala Leu Glu Phe
1               5                   10                  15

<210> SEQ ID NO 252
<211> LENGTH: 15
<212> TYPE: PRT
<213> ORGANISM: Artificial Sequence
<220> FEATURE:
<223> OTHER INFORMATION: Synthetic

<400> SEQUENCE: 252

Arg Gln Cys Ile Ile Leu Met Asn His Arg Gln Cys Phe Phe Lys
1               5                   10                  15

<210> SEQ ID NO 253
<211> LENGTH: 15
<212> TYPE: PRT
<213> ORGANISM: Artificial Sequence
<220> FEATURE:
<223> OTHER INFORMATION: Synthetic

<400> SEQUENCE: 253

Arg Ser Cys Thr Pro Tyr Met Met Ser Ser Leu Cys Asn Thr
1               5                   10                  15

<210> SEQ ID NO 254
<211> LENGTH: 15
<212> TYPE: PRT
<213> ORGANISM: Artificial Sequence
<220> FEATURE:
<223> OTHER INFORMATION: Synthetic

<400> SEQUENCE: 254

Arg Tyr Cys His Tyr Trp Lys Met Pro Tyr Glu Cys Ser Ser Phe
1               5                   10                  15

<210> SEQ ID NO 255
<211> LENGTH: 15
<212> TYPE: PRT
<213> ORGANISM: Artificial Sequence
<220> FEATURE:
<223> OTHER INFORMATION: Synthetic

<400> SEQUENCE: 255

Ser Cys Val Ser Leu Ser Trp Phe Asp Met Leu Lys Cys Tyr Glu
1               5                   10                  15
```

```
<210> SEQ ID NO 256
<211> LENGTH: 15
<212> TYPE: PRT
<213> ORGANISM: Artificial Sequence
<220> FEATURE:
<223> OTHER INFORMATION: Synthetic

<400> SEQUENCE: 256

Ser Asp Asn Cys Glu Ile Trp Trp Thr Val Cys Ser Ala Ala Met
1               5                   10                  15

<210> SEQ ID NO 257
<211> LENGTH: 15
<212> TYPE: PRT
<213> ORGANISM: Artificial Sequence
<220> FEATURE:
<223> OTHER INFORMATION: Synthetic

<400> SEQUENCE: 257

Ser Phe Cys Trp Ser Tyr Leu Val Ser Ser Gly Leu Cys Gly Val
1               5                   10                  15

<210> SEQ ID NO 258
<211> LENGTH: 15
<212> TYPE: PRT
<213> ORGANISM: Artificial Sequence
<220> FEATURE:
<223> OTHER INFORMATION: Synthetic

<400> SEQUENCE: 258

Ser Met Cys Met Asn Asn Tyr Gly Thr Thr Ile Met Cys Gly Asn
1               5                   10                  15

<210> SEQ ID NO 259
<211> LENGTH: 15
<212> TYPE: PRT
<213> ORGANISM: Artificial Sequence
<220> FEATURE:
<223> OTHER INFORMATION: Synthetic

<400> SEQUENCE: 259

Ser Met Val Gly Cys Gly Trp Ser Thr Phe Cys Pro Ser Arg Gly
1               5                   10                  15

<210> SEQ ID NO 260
<211> LENGTH: 15
<212> TYPE: PRT
<213> ORGANISM: Artificial Sequence
<220> FEATURE:
<223> OTHER INFORMATION: Synthetic

<400> SEQUENCE: 260

Ser Ser Leu His Cys Ala Asn Gly His Thr Cys Pro Phe Cys Leu
1               5                   10                  15

<210> SEQ ID NO 261
<211> LENGTH: 15
<212> TYPE: PRT
<213> ORGANISM: Artificial Sequence
<220> FEATURE:
<223> OTHER INFORMATION: Synthetic

<400> SEQUENCE: 261

Ser Val Cys Ser Tyr Tyr Glu Glu Ser Ser Gly Ile Cys Ser Pro
1               5                   10                  15

<210> SEQ ID NO 262
```

```
<211> LENGTH: 15
<212> TYPE: PRT
<213> ORGANISM: Artificial Sequence
<220> FEATURE:
<223> OTHER INFORMATION: Synthetic

<400> SEQUENCE: 262

Ser Trp Cys Gly Trp Tyr Ala Ala Ser Ser Gly Val Cys Ala Leu
1               5                   10                  15

<210> SEQ ID NO 263
<211> LENGTH: 15
<212> TYPE: PRT
<213> ORGANISM: Artificial Sequence
<220> FEATURE:
<223> OTHER INFORMATION: Synthetic

<400> SEQUENCE: 263

Thr Cys Ile Ser Gln Thr Ile Asp Ser Tyr Leu Asn Cys Val Asn
1               5                   10                  15

<210> SEQ ID NO 264
<211> LENGTH: 15
<212> TYPE: PRT
<213> ORGANISM: Artificial Sequence
<220> FEATURE:
<223> OTHER INFORMATION: Synthetic

<400> SEQUENCE: 264

Thr Phe Cys Asn Leu Tyr Thr Lys Ser Ser Asn Ile Cys Met Ser
1               5                   10                  15

<210> SEQ ID NO 265
<211> LENGTH: 15
<212> TYPE: PRT
<213> ORGANISM: Artificial Sequence
<220> FEATURE:
<223> OTHER INFORMATION: Synthetic

<400> SEQUENCE: 265

Thr Tyr Cys Val Phe His Glu Tyr Leu Asp Asn Thr Cys Asn Asn
1               5                   10                  15

<210> SEQ ID NO 266
<211> LENGTH: 15
<212> TYPE: PRT
<213> ORGANISM: Artificial Sequence
<220> FEATURE:
<223> OTHER INFORMATION: Synthetic

<400> SEQUENCE: 266

Val Ala Thr Gly Cys Pro Asn Leu Met Leu Cys Gly Ser Trp Pro
1               5                   10                  15

<210> SEQ ID NO 267
<211> LENGTH: 15
<212> TYPE: PRT
<213> ORGANISM: Artificial Sequence
<220> FEATURE:
<223> OTHER INFORMATION: Synthetic

<400> SEQUENCE: 267

Val Glu Tyr Cys Ser Leu Leu Leu Gly Asn Arg Cys Asp Tyr Trp
1               5                   10                  15

<210> SEQ ID NO 268
<211> LENGTH: 15
```

<212> TYPE: PRT
<213> ORGANISM: Artificial Sequence
<220> FEATURE:
<223> OTHER INFORMATION: Synthetic

<400> SEQUENCE: 268

Val Gly Cys Asn Met Tyr Leu Met Ser Ala Gly Leu Cys Val Asp
1               5                   10                  15

<210> SEQ ID NO 269
<211> LENGTH: 15
<212> TYPE: PRT
<213> ORGANISM: Artificial Sequence
<220> FEATURE:
<223> OTHER INFORMATION: Synthetic

<400> SEQUENCE: 269

Val Leu Tyr Cys Ser Trp Asp Ser Gly Thr Cys Val Gly Ser His
1               5                   10                  15

<210> SEQ ID NO 270
<211> LENGTH: 15
<212> TYPE: PRT
<213> ORGANISM: Artificial Sequence
<220> FEATURE:
<223> OTHER INFORMATION: Synthetic

<400> SEQUENCE: 270

Val Met Phe Ser Cys Tyr Tyr Leu Glu Thr Cys Ala Pro Gly Val
1               5                   10                  15

<210> SEQ ID NO 271
<211> LENGTH: 15
<212> TYPE: PRT
<213> ORGANISM: Artificial Sequence
<220> FEATURE:
<223> OTHER INFORMATION: Synthetic

<400> SEQUENCE: 271

Val Arg Ile Gly Leu Cys Pro Glu Ser Cys Leu Val Ser Gly Phe
1               5                   10                  15

<210> SEQ ID NO 272
<211> LENGTH: 15
<212> TYPE: PRT
<213> ORGANISM: Artificial Sequence
<220> FEATURE:
<223> OTHER INFORMATION: Synthetic

<400> SEQUENCE: 272

Val Thr Cys Thr Tyr Tyr Ala Thr Ser Ser Leu Cys Asn Thr
1               5                   10                  15

<210> SEQ ID NO 273
<211> LENGTH: 15
<212> TYPE: PRT
<213> ORGANISM: Artificial Sequence
<220> FEATURE:
<223> OTHER INFORMATION: Synthetic

<400> SEQUENCE: 273

Val Thr Gly Cys Ile Leu Leu Pro Lys Ala Trp Cys Trp Gly Asp
1               5                   10                  15

<210> SEQ ID NO 274
<211> LENGTH: 15
<212> TYPE: PRT

```
<213> ORGANISM: Artificial Sequence
<220> FEATURE:
<223> OTHER INFORMATION: Synthetic

<400> SEQUENCE: 274

Val Trp Cys Ser Ile Tyr Glu Tyr Ser Ser Asn Leu Cys Ser Arg
1               5                   10                  15

<210> SEQ ID NO 275
<211> LENGTH: 15
<212> TYPE: PRT
<213> ORGANISM: Artificial Sequence
<220> FEATURE:
<223> OTHER INFORMATION: Synthetic

<400> SEQUENCE: 275

Trp Met Leu Glu Cys Gln Tyr Asn Asn Thr Cys Asn Asn Met Thr
1               5                   10                  15

<210> SEQ ID NO 276
<211> LENGTH: 15
<212> TYPE: PRT
<213> ORGANISM: Artificial Sequence
<220> FEATURE:
<223> OTHER INFORMATION: Synthetic

<400> SEQUENCE: 276

Trp Pro Cys Ser Pro Leu Glu Tyr Tyr Asn Asn Ile Cys Asn Val
1               5                   10                  15

<210> SEQ ID NO 277
<211> LENGTH: 15
<212> TYPE: PRT
<213> ORGANISM: Artificial Sequence
<220> FEATURE:
<223> OTHER INFORMATION: Synthetic

<400> SEQUENCE: 277

Trp Thr Tyr Asp Cys His Leu Asn Gln Thr Cys Pro Thr Tyr Tyr
1               5                   10                  15

<210> SEQ ID NO 278
<211> LENGTH: 15
<212> TYPE: PRT
<213> ORGANISM: Artificial Sequence
<220> FEATURE:
<223> OTHER INFORMATION: Synthetic

<400> SEQUENCE: 278

Tyr Cys Ser Ile Asn Met Tyr Leu Ile Gly Gly Asn Cys Met Tyr
1               5                   10                  15

<210> SEQ ID NO 279
<211> LENGTH: 15
<212> TYPE: PRT
<213> ORGANISM: Artificial Sequence
<220> FEATURE:
<223> OTHER INFORMATION: Synthetic

<400> SEQUENCE: 279

Tyr Phe Cys Ser Leu Tyr Ala Asn Ser Ala Gly Phe Cys Gly Gly
1               5                   10                  15

<210> SEQ ID NO 280
<211> LENGTH: 15
<212> TYPE: PRT
<213> ORGANISM: Artificial Sequence
```

```
<220> FEATURE:
<223> OTHER INFORMATION: Synthetic

<400> SEQUENCE: 280

Tyr Val Ser Cys Tyr Met Phe Ser Ser Cys Pro Ser Thr Trp
1               5                   10                  15

<210> SEQ ID NO 281
<211> LENGTH: 265
<212> TYPE: PRT
<213> ORGANISM: Artificial Sequence
<220> FEATURE:
<223> OTHER INFORMATION: Synthetic

<400> SEQUENCE: 281

Gln Gly Gln Ser Gly Gln Gly Thr Ser Tyr Cys Ser Ile Glu His Tyr
1               5                   10                  15

Pro Cys Asn Thr His His Gly Gly Ser Ser Gly Gly Ser Ile Ser
            20                  25                  30

Ser Gly Leu Leu Ser Gly Arg Ser Asp Asn Pro Gly Gly Gly Ser Asp
            35                  40                  45

Ile Gln Leu Thr Gln Ser Pro Ser Ser Leu Ser Ala Ser Val Gly Asp
50                  55                  60

Arg Val Thr Ile Thr Cys Arg Ala Ser Glu Ser Val Asp Ala Tyr Gly
65                  70                  75                  80

Ile Ser Phe Met Asn Trp Phe Gln Gln Lys Pro Gly Lys Ala Pro Lys
                85                  90                  95

Leu Leu Ile Tyr Ala Ala Ser Asn Gln Gly Ser Gly Val Pro Ser Arg
            100                 105                 110

Phe Ser Gly Ser Gly Ser Gly Thr Asp Phe Thr Leu Thr Ile Ser Ser
        115                 120                 125

Met Gln Pro Glu Asp Phe Ala Thr Tyr Tyr Cys Gln Gln Ser Lys Asp
130                 135                 140

Val Pro Trp Thr Phe Gly Gln Gly Thr Lys Leu Glu Ile Lys Arg Thr
145                 150                 155                 160

Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
            180                 185                 190

Arg Glu Ala Lys Val Gln Trp Lys Val Asp Asn Ala Leu Gln Ser Gly
        195                 200                 205

Asn Ser Gln Glu Ser Val Thr Glu Gln Asp Ser Lys Asp Ser Thr Tyr
210                 215                 220

Ser Leu Ser Ser Thr Leu Thr Leu Ser Lys Ala Asp Tyr Glu Lys His
225                 230                 235                 240

Lys Val Tyr Ala Cys Glu Val Thr His Gln Gly Leu Ser Ser Pro Val
                245                 250                 255

Thr Lys Ser Phe Asn Arg Gly Glu Cys
            260                 265

<210> SEQ ID NO 282
<211> LENGTH: 445
<212> TYPE: PRT
<213> ORGANISM: Artificial Sequence
<220> FEATURE:
<223> OTHER INFORMATION: Synthetic

<400> SEQUENCE: 282
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Met Ser Trp Val Arg Gln Ala Pro Gly Lys Gly Leu Glu Trp Val
        35                  40                  45

Ala Tyr Ile Ser Asn Ser Gly Gly Asn Ala His Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Glu Asp Tyr Gly Thr Ser Pro Phe Val Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
        210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
```

Asn His Tyr Thr Gln Lys Ser Leu Ser Leu Ser Leu Gly
            435                 440                 445

<210> SEQ ID NO 283
<211> LENGTH: 11
<212> TYPE: PRT
<213> ORGANISM: Artificial Sequence
<220> FEATURE:
<223> OTHER INFORMATION: Synthetic

<400> SEQUENCE: 283

Arg Ala Ser Gln Ser Ile Ser Ser Tyr Leu Asn
1               5                   10

<210> SEQ ID NO 284
<211> LENGTH: 7
<212> TYPE: PRT
<213> ORGANISM: Artificial Sequence
<220> FEATURE:
<223> OTHER INFORMATION: Synthetic

<400> SEQUENCE: 284

Ala Ala Ser Ser Leu Gln Ser
1               5

<210> SEQ ID NO 285
<211> LENGTH: 7
<212> TYPE: PRT
<213> ORGANISM: Artificial Sequence
<220> FEATURE:
<223> OTHER INFORMATION: Synthetic

<400> SEQUENCE: 285

Asp Asn Gly Tyr Pro Ser Thr
1               5

<210> SEQ ID NO 286
<211> LENGTH: 5
<212> TYPE: PRT
<213> ORGANISM: Artificial Sequence
<220> FEATURE:
<223> OTHER INFORMATION: Synthetic

<400> SEQUENCE: 286

Ser Tyr Ala Met Ser
1               5

<210> SEQ ID NO 287
<211> LENGTH: 15
<212> TYPE: PRT
<213> ORGANISM: Artificial Sequence
<220> FEATURE:
<223> OTHER INFORMATION: Synthetic

<400> SEQUENCE: 287

Ser Ser Ile Trp Arg Asn Gly Ile Val Thr Val Tyr Ala Asp Ser
1               5                   10                  15

<210> SEQ ID NO 288
<211> LENGTH: 7
<212> TYPE: PRT
<213> ORGANISM: Artificial Sequence
<220> FEATURE:
<223> OTHER INFORMATION: Synthetic

<400> SEQUENCE: 288

```
Trp Ser Ala Ala Phe Asp Tyr
1               5

<210> SEQ ID NO 289
<211> LENGTH: 15
<212> TYPE: PRT
<213> ORGANISM: Artificial Sequence
<220> FEATURE:
<223> OTHER INFORMATION: Synthetic

<400> SEQUENCE: 289

Tyr Cys Glu Val Ser Glu Leu Phe Val Leu Pro Trp Cys Met Gly
1               5                   10                  15

<210> SEQ ID NO 290
<211> LENGTH: 15
<212> TYPE: PRT
<213> ORGANISM: Artificial Sequence
<220> FEATURE:
<223> OTHER INFORMATION: Synthetic

<400> SEQUENCE: 290

Ser Cys Leu Met His Pro His Tyr Ala His Asp Tyr Cys Tyr Val
1               5                   10                  15

<210> SEQ ID NO 291
<211> LENGTH: 15
<212> TYPE: PRT
<213> ORGANISM: Artificial Sequence
<220> FEATURE:
<223> OTHER INFORMATION: Synthetic

<400> SEQUENCE: 291

Leu Cys Glu Val Leu Met Leu Leu Gln His Pro Trp Cys Met Gly
1               5                   10                  15

<210> SEQ ID NO 292
<211> LENGTH: 15
<212> TYPE: PRT
<213> ORGANISM: Artificial Sequence
<220> FEATURE:
<223> OTHER INFORMATION: Synthetic

<400> SEQUENCE: 292

Ile Ala Cys Arg His Phe Met Glu Gln Leu Pro Phe Cys His His
1               5                   10                  15

<210> SEQ ID NO 293
<211> LENGTH: 15
<212> TYPE: PRT
<213> ORGANISM: Artificial Sequence
<220> FEATURE:
<223> OTHER INFORMATION: Synthetic

<400> SEQUENCE: 293

Phe Gly Pro Arg Cys Gly Glu Ala Ser Thr Cys Val Pro Tyr Glu
1               5                   10                  15

<210> SEQ ID NO 294
<211> LENGTH: 15
<212> TYPE: PRT
<213> ORGANISM: Artificial Sequence
<220> FEATURE:
<223> OTHER INFORMATION: Synthetic

<400> SEQUENCE: 294
```

Ile Leu Tyr Cys Asp Ser Trp Gly Ala Gly Cys Leu Thr Arg Pro
1               5                   10                  15

<210> SEQ ID NO 295
<211> LENGTH: 15
<212> TYPE: PRT
<213> ORGANISM: Artificial Sequence
<220> FEATURE:
<223> OTHER INFORMATION: Synthetic

<400> SEQUENCE: 295

Gly Ile Ala Leu Cys Pro Ser His Phe Cys Gln Leu Pro Gln Thr
1               5                   10                  15

<210> SEQ ID NO 296
<211> LENGTH: 15
<212> TYPE: PRT
<213> ORGANISM: Artificial Sequence
<220> FEATURE:
<223> OTHER INFORMATION: Synthetic

<400> SEQUENCE: 296

Asp Gly Pro Arg Cys Phe Val Ser Gly Glu Cys Ser Pro Ile Gly
1               5                   10                  15

<210> SEQ ID NO 297
<211> LENGTH: 15
<212> TYPE: PRT
<213> ORGANISM: Artificial Sequence
<220> FEATURE:
<223> OTHER INFORMATION: Synthetic

<400> SEQUENCE: 297

Leu Cys Tyr Lys Leu Asp Tyr Asp Asp Arg Ser Tyr Cys His Ile
1               5                   10                  15

<210> SEQ ID NO 298
<211> LENGTH: 15
<212> TYPE: PRT
<213> ORGANISM: Artificial Sequence
<220> FEATURE:
<223> OTHER INFORMATION: Synthetic

<400> SEQUENCE: 298

Pro Cys His Pro His Pro Tyr Asp Ala Arg Pro Tyr Cys Asn Val
1               5                   10                  15

<210> SEQ ID NO 299
<211> LENGTH: 15
<212> TYPE: PRT
<213> ORGANISM: Artificial Sequence
<220> FEATURE:
<223> OTHER INFORMATION: Synthetic

<400> SEQUENCE: 299

Pro Cys Tyr Trp His Pro Phe Phe Ala Tyr Arg Tyr Cys Asn Thr
1               5                   10                  15

<210> SEQ ID NO 300
<211> LENGTH: 15
<212> TYPE: PRT
<213> ORGANISM: Artificial Sequence
<220> FEATURE:
<223> OTHER INFORMATION: Synthetic

<400> SEQUENCE: 300

Val Cys Tyr Tyr Met Asp Trp Leu Gly Arg Asn Trp Cys Ser Ser

<210> SEQ ID NO 301
<211> LENGTH: 15
<212> TYPE: PRT
<213> ORGANISM: Artificial Sequence
<220> FEATURE:
<223> OTHER INFORMATION: Synthetic

<400> SEQUENCE: 301

Leu Cys Asp Leu Phe Lys Leu Arg Glu Phe Pro Tyr Cys Met Gly
1               5                   10                  15

<210> SEQ ID NO 302
<211> LENGTH: 15
<212> TYPE: PRT
<213> ORGANISM: Artificial Sequence
<220> FEATURE:
<223> OTHER INFORMATION: Synthetic

<400> SEQUENCE: 302

Tyr Leu Pro Cys His Phe Val Pro Ile Gly Ala Cys Asn Asn Lys
1               5                   10                  15

<210> SEQ ID NO 303
<211> LENGTH: 15
<212> TYPE: PRT
<213> ORGANISM: Artificial Sequence
<220> FEATURE:
<223> OTHER INFORMATION: Synthetic

<400> SEQUENCE: 303

Ile Phe Cys His Met Gly Val Val Val Pro Gln Cys Ala Asn Tyr
1               5                   10                  15

<210> SEQ ID NO 304
<211> LENGTH: 15
<212> TYPE: PRT
<213> ORGANISM: Artificial Sequence
<220> FEATURE:
<223> OTHER INFORMATION: Synthetic

<400> SEQUENCE: 304

Ala Cys His Pro His Pro Tyr Asp Ala Arg Pro Tyr Cys Asn Val
1               5                   10                  15

<210> SEQ ID NO 305
<211> LENGTH: 15
<212> TYPE: PRT
<213> ORGANISM: Artificial Sequence
<220> FEATURE:
<223> OTHER INFORMATION: Synthetic

<400> SEQUENCE: 305

Pro Cys His Pro Ala Pro Tyr Asp Ala Arg Pro Tyr Cys Asn Val
1               5                   10                  15

<210> SEQ ID NO 306
<211> LENGTH: 15
<212> TYPE: PRT
<213> ORGANISM: Artificial Sequence
<220> FEATURE:
<223> OTHER INFORMATION: Synthetic

<400> SEQUENCE: 306

Pro Cys His Pro His Ala Tyr Asp Ala Arg Pro Tyr Cys Asn Val
1               5                   10                  15

```
<210> SEQ ID NO 307
<211> LENGTH: 15
<212> TYPE: PRT
<213> ORGANISM: Artificial Sequence
<220> FEATURE:
<223> OTHER INFORMATION: Synthetic

<400> SEQUENCE: 307

Pro Cys His Pro His Pro Ala Asp Ala Arg Pro Tyr Cys Asn Val
1               5                   10                  15

<210> SEQ ID NO 308
<211> LENGTH: 15
<212> TYPE: PRT
<213> ORGANISM: Artificial Sequence
<220> FEATURE:
<223> OTHER INFORMATION: Synthetic

<400> SEQUENCE: 308

Pro Cys His Pro His Pro Tyr Ala Ala Arg Pro Tyr Cys Asn Val
1               5                   10                  15

<210> SEQ ID NO 309
<211> LENGTH: 15
<212> TYPE: PRT
<213> ORGANISM: Artificial Sequence
<220> FEATURE:
<223> OTHER INFORMATION: Synthetic

<400> SEQUENCE: 309

Pro Cys His Pro His Pro Tyr Asp Ala Ala Pro Tyr Cys Asn Val
1               5                   10                  15

<210> SEQ ID NO 310
<211> LENGTH: 15
<212> TYPE: PRT
<213> ORGANISM: Artificial Sequence
<220> FEATURE:
<223> OTHER INFORMATION: Synthetic

<400> SEQUENCE: 310

Pro Cys His Pro His Pro Tyr Asp Ala Arg Pro Ala Cys Asn Val
1               5                   10                  15

<210> SEQ ID NO 311
<211> LENGTH: 15
<212> TYPE: PRT
<213> ORGANISM: Artificial Sequence
<220> FEATURE:
<223> OTHER INFORMATION: Synthetic

<400> SEQUENCE: 311

Pro Cys His Pro His Pro Tyr Asp Ala Arg Pro Tyr Cys Ala Val
1               5                   10                  15

<210> SEQ ID NO 312
<211> LENGTH: 15
<212> TYPE: PRT
<213> ORGANISM: Artificial Sequence
<220> FEATURE:
<223> OTHER INFORMATION: Synthetic

<400> SEQUENCE: 312

Pro Cys His Ala His Pro Tyr Asp Ala Arg Pro Tyr Cys Asn Val
1               5                   10                  15
```

```
<210> SEQ ID NO 313
<211> LENGTH: 15
<212> TYPE: PRT
<213> ORGANISM: Artificial Sequence
<220> FEATURE:
<223> OTHER INFORMATION: Synthetic

<400> SEQUENCE: 313

Pro Cys His Pro His Pro Tyr Asp Ala Arg Ala Tyr Cys Asn Val
1               5                   10                  15

<210> SEQ ID NO 314
<211> LENGTH: 264
<212> TYPE: PRT
<213> ORGANISM: Artificial Sequence
<220> FEATURE:
<223> OTHER INFORMATION: Synthetic

<400> SEQUENCE: 314

Gln Gly Gln Ser Gly Ser Gly Ile Ala Leu Cys Pro Ser His Phe Cys
1               5                   10                  15

Gln Leu Pro Gln Thr Gly Gly Ser Ser Gly Gly Ser Gly Gly Ser
                20                  25                  30

Gly Gly Ile Ser Ser Gly Leu Leu Ser Gly Arg Ser Asp Asn His Gly
            35                  40                  45

Gly Ser Asp Ile Gln Met Thr Gln Ser Pro Ser Ser Leu Ser Ala Ser
        50                  55                  60

Val Gly Asp Arg Val Thr Ile Thr Cys Arg Ala Ser Gln Ser Ile Ser
65                  70                  75                  80

Ser Tyr Leu Asn Trp Tyr Gln Gln Lys Pro Gly Lys Ala Pro Lys Leu
                85                  90                  95

Leu Ile Tyr Ala Ala Ser Ser Leu Gln Ser Gly Val Pro Ser Arg Phe
            100                 105                 110

Ser Gly Ser Gly Ser Gly Thr Asp Phe Thr Leu Thr Ile Ser Ser Leu
        115                 120                 125

Gln Pro Glu Asp Phe Ala Thr Tyr Tyr Cys Gln Gln Asp Asn Gly Tyr
    130                 135                 140

Pro Ser Thr Phe Gly Gly Gly Thr Lys Val Glu Ile Lys Arg Thr Val
145                 150                 155                 160

Ala Ala Pro Ser Val Phe Ile Phe Pro Pro Ser Asp Glu Gln Leu Lys
                165                 170                 175

Ser Gly Thr Ala Ser Val Val Cys Leu Leu Asn Asn Phe Tyr Pro Arg
            180                 185                 190

Glu Ala Lys Val Gln Trp Lys Val Asp Asn Ala Leu Gln Ser Gly Asn
        195                 200                 205

Ser Gln Glu Ser Val Thr Glu Gln Asp Ser Lys Asp Ser Thr Tyr Ser
    210                 215                 220

Leu Ser Ser Thr Leu Thr Leu Ser Lys Ala Asp Tyr Glu Lys His Lys
225                 230                 235                 240

Val Tyr Ala Cys Glu Val Thr His Gln Gly Leu Ser Ser Pro Val Thr
                245                 250                 255

Lys Ser Phe Asn Arg Gly Glu Cys
            260

<210> SEQ ID NO 315
<211> LENGTH: 442
<212> TYPE: PRT
<213> ORGANISM: Artificial Sequence
```

<220> FEATURE:
<223> OTHER INFORMATION: Synthetic

<400> SEQUENCE: 315

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Trp Arg Asn Gly Ile Val Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Ser Ala Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

```
Phe Leu Tyr Ser Arg Leu Thr Val Asp Lys Ser Arg Trp Gln Glu Gly
            405                 410                 415

Asn Val Phe Ser Cys Ser Val Met His Glu Ala Leu His Asn His Tyr
            420                 425                 430

Thr Gln Lys Ser Leu Ser Leu Ser Leu Gly
            435                 440
```

COMPOSITIONS CONTAINING ACTIVATABLE ANTIBODIES

CROSS REFERENCE TO RELATED APPLICATIONS

This applications claims priority benefit of U.S. provisional application No. 63/007,776, filed Apr. 9, 2020, the entire contents of which are incorporated herein by reference.

REFERENCE TO SEQUENCE LISTING

The present application includes a Sequence Listing filed in electronic format. The Sequence Listing is entitled "CYTX-056-PCT_ST25.txt" created on Mar. 31, 2021, and is 88,000 bytes in size. The information in the electronic format of the Sequence Listing is part of the present application and is incorporated herein by reference in its entirety.

FIELD OF THE INVENTION

The present disclosure relates to compositions and methods relating to intact activatable antibodies and clipped variants thereof, including compositions and methods for making, purifying, measuring, monitoring, and using the compositions.

BACKGROUND

Monoclonal antibodies are a growing class of therapeutic compounds each designed to bind to a target antigen implicated in any one of a number of clinical indications. To date, there is an expansive list of monoclonal antibody products, either at an investigational stage or approved as a new drug. While the burgeoning growth of this product class has resulted in significant advances in the processes used to manufacture them, product aggregation remains a significant issue that must be addressed during the development of a manufacturing process for each new monoclonal antibody drug. Varsha, et al. *BioPharm International* vol. 26, Issue 3. Product aggregation is undesirable as it results in lower yields of drug product, and potential safety issues if not removed from the drug product composition. Id. For example, aggregation may cause the formation of subvisible particles that may expose normally unexposed epitopes, leading to potentially increased immunogenicity if administered to a patient. Id.

The aggregates are typically large, tangled clusters of denatured antibody molecules that form irreversibly either during product expression in the cell culture, during product purification in downstream processing, or during storage. Id. A variety of factors may contribute to the formation of aggregates. Improvements in the safety and/or efficacy of antibody-based therapeutics have been sought, and in certain cases, achieved, by modifying the structure of the molecule. However, in certain instances, these structural changes introduce additional challenges with regards to the manufacture of purified antibody-based therapeutics.

Accordingly, new processes for manufacturing antibody-based therapeutic compounds would be highly desirable.

SUMMARY OF THE INVENTION

In one aspect, the present disclosure includes a composition including an intact activatable antibody and a clipped variant thereof, wherein the clipped variant is present in a reduced amount. In some aspects, the clipped variant thereof includes an antigen binding domain (AB) and at least a portion of a cleavable moiety (CM). In some aspects, the clipped variant lacks a masking moiety (MM) from at least one prodomain.

In some aspects, the composition comprises at least about 90% intact activatable antibody, as measured by reducing SDS-cGE, less than about 10% clipped variant, as determined by reducing SDS-cGE, less than about 5% high molecular weight species (HMWS), as determined by SE-HPLC, and less than about 150 ppm host cell proteins (HCP), as determined by a corresponding HCP ELISA. In some aspects, the composition includes greater than 95% intact activatable antibody and 0.05 to 5% clipped variant. In some aspects, the composition includes greater than 90% intact activatable antibody, 0.05 to 5% clipped variant, less than 150 ppm host cell proteins (HCP), and/or less than 5% HMWS. In some aspects, the composition includes greater than 96% intact activatable antibody, 0.05 to 4% clipped variant, less than 150 ppm HCP and less than 5% HMWS. In some aspects, the composition includes greater than 97% intact activatable antibody, 0.05 to 3% clipped variant, less than 150 ppm host cell proteins (HCP) and less than 5% HMWS. In some aspects, the composition includes greater than 98% intact activatable antibody, 0.05 to 2% clipped variant, less than 150 ppm host cell proteins (HCP) and less than 5% HMWS. In some aspects, the composition includes greater than 99% intact activatable antibody, 0.05 to 1% clipped variant, less than 150 ppm host cell proteins (HCP) and less than 5% HMWS. In some aspects, the present disclosure includes a container, vial, syringe, or injector device containing the composition.

In one aspect, the present disclosure includes a process for producing a composition including: (A) greater than 95% intact activatable antibody comprising a MM, a CM, and a AB; and (B) 0.05 to 5% clipped variant thereof, the process including loading an aqueous feedstock comprising water, (A), (B), and a first salt onto a chromatography column, wherein the chromatography column comprises a stationary phase that comprises a support matrix and hydrophobic ligands bound thereto, and eluting the chromatography column with an eluent comprising water and a second salt to obtain the composition. In one aspect, the process includes reducing the amount of clipped variant in the process stream by 75 to 90%. In one aspect, the process includes reducing the amount of HCP in the process stream by 75 to 90%. In one aspect, the process includes reducing the amount of HMWS in the process stream by 75 to 90%. In one aspect, the process includes reducing the amount of clipped variant, HCP, and HMWS in the process stream by 70 to 95%.

In one aspect, the present disclosure includes a method of separating an intact activatable antibody from a clipped variant thereof that has an amino acid sequence that is at least 90%, 91%, 92%, 93%, 94%, 95%, 96%, 97%, 98%, or 99% identical to the amino acid sequence of the intact activatable antibody, including (i) loading an aqueous feedstock comprising water, the intact activatable antibody, the clipped variant thereof, and a first salt onto a chromatography column, wherein the chromatography column comprises a stationary phase that comprises a support matrix and hydrophobic ligands bound thereto, and (ii) eluting the chromatography column with an eluent comprising water and a second salt to obtain a composition wherein the amount of the clipped variant in the process stream is reduced by at least 70%. In some embodiments, the amount of the clipped variant in the process stream is reduced by at least 75%, 80%, 85%, or 90%.

In one aspect, the present disclosure includes a composition and process for making a composition having at least 90%, 91%, 92%, 93%, 94%, 95%, 96%, 97%, 98%, or 99% of the total protein by weight in the composition in the form of intact activatable antibody, and 0.1 to 10% of the total protein by weight in the form of aggregated and clipped variants thereof.

In one aspect, the present disclosure includes a method for producing a pharmaceutical composition including an intact activatable antibody and less than 5% clipped variant thereof, less than 5% aggregates thereof, less than 150 ppm HCP, or a combination thereof, the method including loading an aqueous feedstock comprising water, (A), (B), and a first salt onto a chromatography column, wherein the chromatography column comprises a stationary phase that comprises a support matrix and hydrophobic ligands bound thereto, and eluting the chromatography column with an eluent comprising water and a second salt to obtain the composition.

In some aspects, the present disclosure includes administering the composition disclosed herein to a subject in need thereof, e.g., a patient suffering from a cancer, an inflammatory disease, an autoimmune disease, or a combination thereof. In some aspects, the present disclosure includes administering a composition disclosed herein with a subtoxic dose of a clipped variant of an activatable antibody and a dose of an activatable antibody that is activated in a disease microenvironment. In some aspects, the present disclosure includes expanding a therapeutic window of treating a subject by administering a composition of the present disclosure.

In one aspect, the present invention provides a process for producing a purified composition of intact activatable antibody, the process comprising:
(a) loading an aqueous feedstock comprising water, an intact activatable antibody, a clipped impurity, and a first salt onto a chromatography column,
   wherein the chromatography column comprises a stationary phase that comprises a support matrix and ligands bound thereto,
      wherein the ligands comprise a hydrophobic substituent, and
   wherein the intact activatable antibody comprises (i) at least a first antigen binding domain (AB) that has a specific binding affinity for a first biological target, and (ii) a first prodomain,
      wherein the at least first AB comprises a first antibody light variable domain (VL) and a first antibody heavy variable domain (VH),
      wherein the first prodomain comprises a first masking moiety (MM) and a first cleavable moiety (CM), and
      wherein the first AB is coupled to the first prodomain; and
(b) eluting the chromatography column with an eluent comprising water and a second salt to generate an eluate that comprises a purified composition comprising intact activatable antibody,
   wherein the eluate is substantially depleted of the clipped impurity.

In another aspect, the aqueous feedstock further comprises other impurities, such as, for example, host cell proteins (HCP) and/or high molecular weight species (HMWS), wherein quantities of these impurities are substantially reduced in the eluate.

In a further aspect, the present invention provides purified intact activatable antibody compositions having either no or very low residual quantities of clipped impurity.

In a still further aspect, the present invention provides purified intact activatable antibody compositions having either no or very low residual quantities of clipped impurity, host cell protein (HCP), and high molecular weight species (HMWS).

In another aspect, the present disclosure includes a method for determining or monitoring a relative quantity of an activatable antibody and a clipped variant thereof during a composition production process, by subjecting a sample composition comprising a population of activatable antibody and a population of clipped variants thereof to a gel capillary electrophoresis procedure; separating the population of activatable antibody from the population of clipped variants thereof in the gel capillary electrophoresis procedure; and quantifying the relative amounts of the population of activatable antibody and the population of clipped variants thereof by determining the peak area corresponding to intact prodomain-encoding polypeptide and the peak area corresponding to clipped prodomain-encoding polypeptide(s) thereof.

BRIEF DESCRIPTION OF THE DRAWINGS

FIG. 1C depicts the results of a mass spectrophotometry analysis of a sample obtained from a bioharvest of activatable anti-CD166 antibody. The results show a single peak corresponding to the expected molecular weight for the corresponding single-arm clipped impurity. No peaks were observed at the expected molecular weights for fully clipped impurity.

DETAILED DESCRIPTION OF THE INVENTION

Figure 1A:
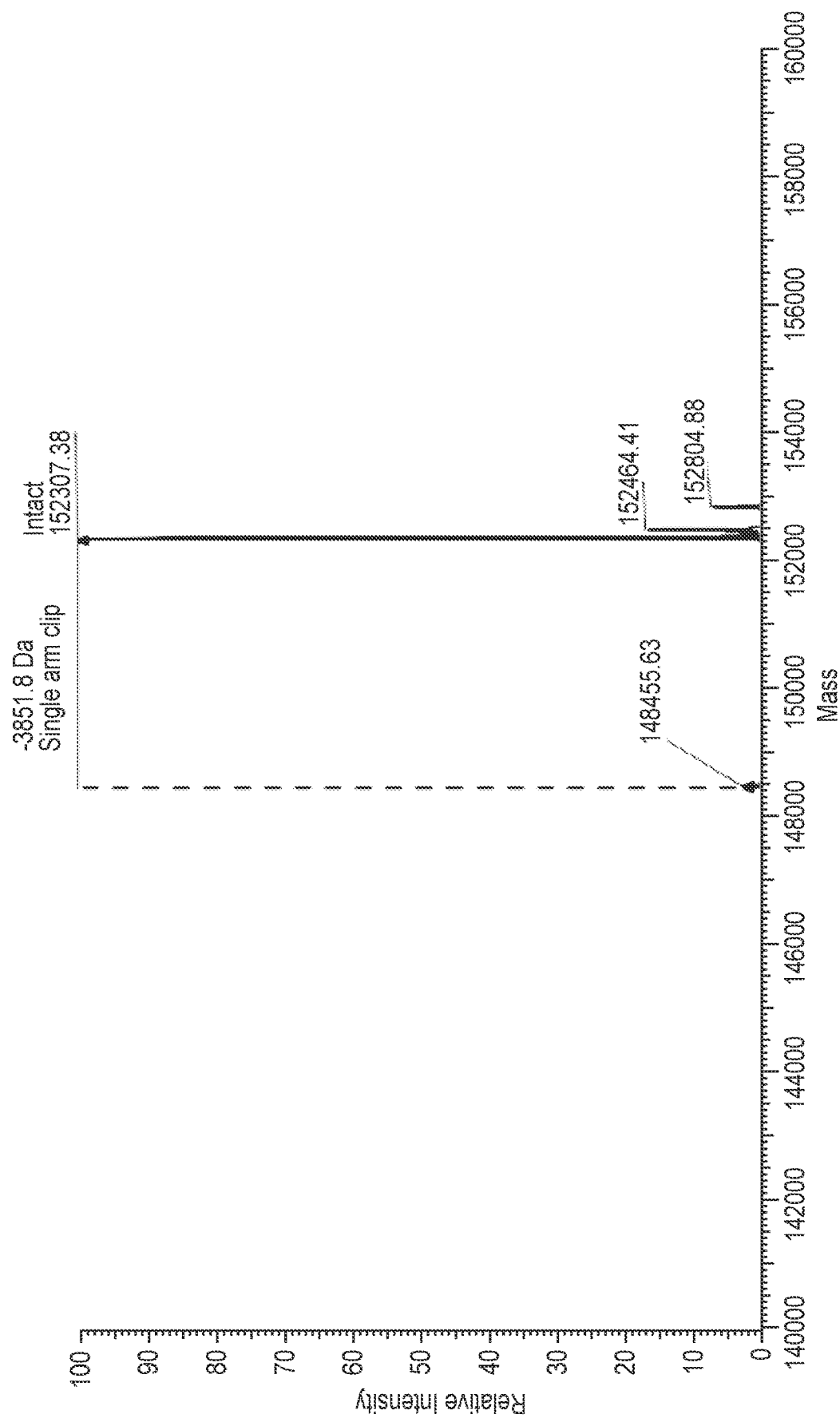
FIG. 1A depicts the results of a mass spectrophotometry analysis of a sample obtained from a bioharvest of activatable anti-PDL1 antibody. The results show a single peak corresponding to the expected molecular weight for the corresponding single-arm clipped impurity. No peaks were observed at the expected molecular weights for fully clipped impurity.

Toxicities due to broad target expression have limited the therapeutic effectiveness of monoclonal antibody therapies. To address this, recombinantly produced activatable antibodies that include an antigen binding domain (AB), a cleavable moiety (CM), and a masking moiety (MM) that is capable of inhibiting the specific binding of the AB to its target have been produced. Such activatable antibodies behave like an antibody with respect to binding specificity to a biological target only after activation by exposure to certain proteases, particularly proteases that are upregulated in a localized disease environment (e.g., a tumor microenvironment).

The present inventors have now found that, due to proteases present in host cells during the manufacturing process and the relative lability of protease substrates, compositions containing activatable antibodies are often found to contain a significant proportion of clipped variants that lack the MM and therefore are free to indiscriminately bind to targets on healthy cells, thereby potentially causing the dose-dependent toxicities and side effects associated with monoclonal antibodies. The presence of clipped variants in a therapeutic dose may have the effect of reducing the dose of intact activatable antibody in systemic circulation that is available to reach the target tissues (e.g., cancerous tissue) due to sequestration of the clipped variants in normal tissue. In addition to the presence of clipped variants, the present inventors have also observed that certain compositions containing activatable antibodies also contain significant portions of high molecular weight species due to aggregation, which may reduce efficacy and increase immunogenicity. Particularly, the present inventors have now found that clipped variants are similar in size and identical in amino acid sequence to the activatable antibody parent except for the truncation caused by cleavage. Because of the similarities in size and structure and physicochemical properties of the clipped variant and the intact activatable antibody, it is challenging to separate the clipped variants from the intact activatable antibody parent to obtain a composition having high purity (e.g., a high percentage of intact, non-aggregated activatable antibody), in high yield. As described below, the present inventors have discovered methods for purifying activatable antibody compositions to selectively remove clipped variants, resulting in compositions comprising high levels of intact activatable antibody with low or no detectable levels of clipped variants.

Definitions

The terms "activatable antibody", "protease-activatable antibody", and "intact activatable antibody" are used interchangeably herein to refer to a recombinantly produced "masked" binding compound that is designed to behave like an antibody with respect to binding specificity to a biological target only after its activation by exposure to certain proteases. Structurally, activatable antibodies comprise: (1) an antigen binding domain (AB) that, when not masked, specifically binds a biological target; and (2) a prodomain coupled (via peptide bonding) to the AB that comprises or consists of a masking moiety (MM) and a cleavable moiety (CM).

The term "amino acid anion" refers herein to an anionic form of an amino acid. The anionic moiety may, for example, be a deprotonated alpha-carboxyl or R-group carboxyl (e.g., the R-group carboxyl moiety in aspartic acid, glutamic acid, and the like), and the like.

The term "amino acid cation" refers herein to a cationic form of an amino acid. The cationic moiety may, for example, be a protonated alpha-amine or R-group amine (e.g., the R group amine moiety in arginine (i.e., the guanidino moiety), tryptophan, asparagine, glutamine, lysine, histidine, and the like), and the like.

The term "amino acid salt" refers herein to a salt of an amino acid. Illustrative amino acid salts include, for example, an arginine hydrochloride, a lysine hydrochloride, and the like.

The terms "antigen binding domain" and "AB" are used interchangeably herein to refer to a binding domain having a specific binding affinity for a biological target, that is formed from one or more polypeptides encoding an antibody light variable domain (VL) and an antibody heavy variable domain (VH).

As used herein, the term "biological target" refers to a protein that is native to a mammalian species.

As used herein, the term "prodomain" refers herein to a peptide having an amino acid sequence that encodes at a minimum, a masking moiety (MM) and a cleavable moiety (CM). The prodomain may include other sequence elements, such as, for example, a spacer, one or more linkers (e.g., positioned between an MM and a CM and/or between an MM and a VL and/or between an MM and a VH, and/or between a CM and a VL, and/or between a CM and a VH, and the like), and the like.

The terms "masking moiety" and "MM", are used interchangeably herein to refer to a peptide that, when positioned proximal to the AB, interferes with binding of the AB to the biological target.

The terms "cleavable moiety" and "CM" are used interchangeably herein to refer to a peptide that comprises a substrate for at least one protease.

The terms "clipped impurity," and "clipped variant" are used interchangeably herein to the molecule that results after protease-mediated cleavage of an intact activatable antibody. A clipped impurity comprises the AB of the corresponding activatable antibody, but lacks all or a portion of the MM (and thus lacks all, or a portion of the prodomain, e.g., lacks all or a portion of at least one CM and lacks all of the corresponding MM). The terms "clipped impurity" and "clipped variant" may include both "single-arm clipped" and "fully clipped" species.

As used herein, the term "specific binding affinity" refers to a preferential binding of an AB to a particular biological target.

The term "single-arm clipped impurity" or "single-arm clipped species" are used interchangeably herein to refer to a clipped impurity in which all or a portion of only one prodomain of the corresponding intact activatable antibody is missing. The term "single-arm clipped" is used in connection with variants of activatable antibodies, wherein the intact activatable antibody comprises two or more antigen binding domains (AB) and two or more prodomains.

The term "fully clipped impurity" or "fully clipped species" are used interchangeably herein to refer to a clipped impurity in which all or a portion of each prodomain of the corresponding intact activatable antibody is missing.

As used herein, the terms "peptide", "polypeptide", and "protein" are used interchangeably to refer to a polymer or oligomer comprising naturally occurring or non-naturally occurring amino acid residues or amino acid analogues.

The terms "percent clipped impurity," "% clipped impurity," "percent clipped prodomain-encoding polypeptide," and "% clipped prodomain-encoding polypeptide" are used interchangeably herein to refer to the relative quantity of clipped prodomain-encoding polypeptide present in a composition as a percentage of the total of clipped and intact prodomain-encoding polypeptide, where quantities are determined by reducing SDS-capillary gel electrophoresis ("reducing SDS-cGE"). A reducing SDS-cGE assay is illustrated in Example 1. Percent clipped impurity is computed on a relative percent peak area basis for clipped prodomain-encoding polypeptide and intact prodomain-encoding polypeptide as follows:

$$\% \text{ clipped impurity} = \frac{\% \text{ Peak Area},_{clipped}}{(\% \text{ Peak Area},_{clipped} + \% \text{ Peak Area},_{intact})} \times 100$$

where:

$$\% \text{ Peak Area},_{clipped} = \frac{\text{(Peak Area of clipped prodomain-encoding polypeptide)}}{\text{(Total Peak Area corresponding to all species detected)}} \times 100$$

$$\% \text{ Peak Area},_{intact} = \frac{\text{(Peak Area of intact prodomain-encoding polypeptide)}}{\text{(Total Peak Area corresponding to all species detected)}} \times 100$$

The Total Peak Area corresponding to all species detected refers to the sum of all peak areas in the SDS-cGE chromatograph.

The terms "percent intact activatable antibody," "% intact activatable antibody," "percent intact prodomain-encoding polypeptide," and "% intact prodomain-encoding polypeptide" are used interchangeably herein to refer to the relative quantity of intact prodomain-encoding polypeptide present in a composition as a percentage of the total of clipped and intact prodomain-encoding polypeptide, where quantities are determined by reducing SDS-cGE, such as, for example the reducing SDS-cGE assay illustrated in Example 1. Percent intact activatable antibody is computed on the basis of relative percent peak area for clipped prodomain-encoding polypeptide and intact prodomain-encoding polypeptide as follows:

$$\% \text{ intact activatable antibody} = \frac{\% \text{ Peak Area},_{intact}}{(\% \text{ Peak Area},_{clipped} + \% \text{ Peak Area},_{intact})} \times 100$$

where:

$$\% \text{ Peak Area},_{clipped} = \frac{\begin{pmatrix} \text{Peak Area of clipped} \\ \text{prodomain-encoding polypeptide} \end{pmatrix}}{\begin{pmatrix} \text{Total Peak Area corresponding} \\ \text{to all species detected} \end{pmatrix}} \times 100$$

$$\% \text{ Peak Area},_{intact} = \frac{\begin{pmatrix} \text{Peak Area of intact} \\ \text{prodomain-encoding polypeptide} \end{pmatrix}}{\begin{pmatrix} \text{Total Peak Area corresponding} \\ \text{to all species detected} \end{pmatrix}} \times 100$$

The term "prodomain-encoding polypeptide" refers to a polypeptide in an activatable antibody that contains the amino acid sequence which encodes a prodomain. Prodomain-encoding polypeptides may contain amino acid sequence(s) that encode other elements of an activatable antibody in addition to a prodomain. For example, if the prodomain resides within a polypeptide encoding an antibody light chain, the prodomain-encoding polypeptide also encodes at least a VL. Likewise, in other embodiments, if the prodomain resides within a polypeptide encoding an antibody heavy chain, the prodomain-encoding polypeptide also encodes at least a VH. Similarly, if the prodomain resides within a polypeptide encoding an scFv chain, the prodomain-encoding polypeptide further encodes at least a VL and a VH, as well.

The term "clipped prodomain-encoding polypeptide" refers herein to the truncated prodomain-encoding polypeptide that results after the prodomain has been clipped.

The term "intact prodomain-encoding polypeptide" refers herein to a prodomain-encoding polypeptide that has not been clipped, and which contains an intact prodomain.

The term "substantially depleted" is used herein to refer to an eluate composition having either no detectable clipped impurity present, or a relative level of clipped impurity that has been reduced by at least 20%, as compared to the level of clipped impurity present in the aqueous feedstock, where percent reduction is computed as follows:

$$\frac{(\text{"\% clipped impurity"})_{aqueous\ feedstock} - (\text{"\% clipped impurity"})_{eluate}}{(\text{"\% clipped impurity"})_{aqueous\ feedstock}} \times 100,$$

where "% clipped impurity" is the same as defined above.

The term "substantially free" is used herein in connection with clipped variant and clipped impurity to refer to a composition having either no detectable clipped impurity present, or having clipped impurity present wherein the % clipped impurity is less than 5% as determined by SDS-cGE, e.g., 4%, 3%, 2%, 1%, 0.5%, 0.1%, 0.05% or any numeric value or range between zero and 5%.

The term "bound corresponding clipped impurity" and "bound clipped impurity" is used interchangeably herein to refer to clipped impurity that is retained in a chromatography column.

The term "spacer" refers herein to an amino acid residue or a peptide incorporated at a free terminus of the prodomain. In some aspects, a spacer (or "header") may contain glutamine (Q) residues. In some aspects, residues in the spacer minimize aminopeptidase and/or exopeptidase action to prevent cleavage of N-terminal amino acids.

The term "linker" refers herein to an amino acid residue or a peptide that functions to provide further physical separation between the MM, CM, and/or AB elements of the activatable antibody.

As used herein, the terms "high molecular weight species" and "HMWS" are used interchangeably herein to refer to composition impurities (e.g., aggregates) having an effective molecular weight that is greater than that of monomeric intact activatable antibody, as determined by a size exclusion high performance liquid chromatography (SE-HPLC, such as the assay described in Example 1).

The term "effective molecular weight" refers to the molecular weight as determined by an SE-HPLC assay, such as the assay described in Example 1.

As used herein, the term "isocratic" refers to the use of an eluent having a substantially constant, or fixed composition, for the duration of the elution step.

As used herein, the term "hydrophobic interaction chromatography stationary phase" or "HIC stationary phase" refers interchangeably to a type of stationary phase that has ligands which are designed to interact with compounds by exclusively hydrophobic interactions.

The term "multimodal chromatography stationary phase" or "MMC stationary phase" refers interchangeably herein to a type of stationary phase that has ligands which interact with compounds via hydrophobic interactions, as well as one or more additional type of interaction that is not a hydrophobic interaction (such as, for example, electrostatic (via charged ligand substituents), hydrogen bonding, thiophilicity and the like).

As used herein, the term "host cell proteins" and "HCP" are used interchangeably herein to refer to proteins that are native to the host cell from which intact activatable antibody is expressed.

As used herein, the term "total protein yield" refers to the percentage of total protein recovered in a chromatography eluate on the basis of total protein in the aqueous feedstock, and as measured by absorbance at a wavelength of 280 nm in a UV spectrometry assay.

As used herein, the term "intervening unit operation" refers to a process step that occurs between the cell culturing process step and the hydrophobic chromatography process step.

The term "bulk intermediate product composition" refers to the composition of the product of an intervening unit operation.

As used herein, the term "bioharvest composition" refers to a composition derived from a cell culturing step that produces a composition comprising an activatable antibody of interest.

The term "serial", when used in connection with describing the relationship between unit operations, is used herein to refer to two or more unit operations being performed in sequence with respect to time and order, either batch-wise, semi-continuously, or continuously, as a first, then a second, and so on.

As used herein, the term "conjugation reagent" refers to a reactive form of a conjugation moiety that comprises a conjugation moiety covalently bound to a reactive linker.

As used herein, the term "corresponds substantially" when used in connection with two amino acid sequences refers to a level of identity of at least about 90% when optimally aligned.

Two polypeptide sequences are "optimally aligned" when they are aligned using defined parameters, i.e., a defined amino acid substitution matrix, gap existence penalty (also termed gap open penalty), and a gap extension penalty, so as to arrive at the highest similarity score possible for that pair of sequences. The BLOSUM62 matrix (Henikoff and Henikoff (1992) *Proc. Natl. Acad. Sci. USA* 89(22):10915-10919) is often used as a default scoring substitution matrix in polypeptide sequence alignment algorithms (such as BLASTP). The gap existence penalty is imposed for the introduction of a single amino acid gap in one of the aligned sequences, and the gap extension penalty is imposed for each residue position in the gap. Unless otherwise stated, alignment parameters employed herein are: BLOSSUM62 scoring matrix, gap existence penalty-11, and a gap extension penalty-1. The alignment score is defined by the amino acid positions of each sequence at which the alignment begins and ends (e.g., the alignment window), and optionally by the insertion of a gap or multiple gaps into one or both sequences, so as to arrive at the highest possible similarity score.

With respect to any and all numerical ranges provided herein, the ranges are intended to be inclusive of the numerical limits that define the range.

Processes and Compositions of the Present Invention

The present invention relates to the production of purified compositions of intact protease-activatable antibody that are substantially free of clipped impurity and processes for producing such compositions. The process for making the purified compositions is also effective at removing other impurities. Structurally, activatable antibodies comprise: (1) an antigen binding domain (AB) that, when not masked, specifically binds a biological target; and (2) a prodomain coupled to the AB that comprises a masking moiety (MM) and a cleavable moiety (CM). The CM is positioned relative to the MM and AB components such that cleavage of the CM results in the untethering of the MM from its position proximal to the AB. Cleavage thus typically results in generation of an activated antibody that is capable of specifically binding the biological target. Often, the activatable antibody is a homodimer that comprises two identical AB, two identical CM, and two identical MM. In such instances, a clipped variant of the activatable antibody may be a single-arm clipped variant in which only one of the two CM is cleaved, so that the clipped variant comprises one complete CM and one complete MM, but is missing a portion of one CM and all of one MM.

Activatable antibodies may be designed to selectively activate in diseased tissue by incorporating within the CM, a substrate for a protease more prevalently found in an active state in the diseased tissue. Activatable antibodies thus have the potential to mitigate target-mediated toxicity that may arise when monoclonal antibodies bind a biological target that is widely distributed beyond the site of disease. See Desnoyers, et al., *Science Translational Medicine* (16 Oct. 2013) 5(207): 207ra144. Activatable antibodies are described in a number of publications, including, for example, WO 2009/025846, WO 2010/096838, WO 2010/081173, WO 2013/163631, WO 2013/192546, WO 2013/192550, WO 2014/026136, WO 2014/052462, WO 2014/107599, WO 2014/197612, WO 2015/013671, WO 2015/048329, WO 2015/066279, WO 2015/116933, WO 2016/014974, WO 2016/118629, WO 2016/149201, WO 2016/179285, WO 2016/179257, WO 2016/179335, WO 2017/011580, PCT/US2017/059740, U.S. Provisional Application Ser. Nos. 62/469,429, 62/572,467, and 62/613,358, WO 2012/025525, WO 2017/025698, WO 2016/046778, WO 2016/179003, WO 2016/182064, WO 2017/156178, WO 2017/143094, WO 2017/162587, WO 2013/128194, each of which is incorporated herein by reference in their entireties. Further illustrative examples of activatable antibodies suitable for use in the processes and compositions of the present invention are described in more detail hereinbelow.

Though a highly desired product, the manufacture of purified compositions of activatable antibodies is made more challenging due to their activatable nature. Analysis of activatable antibody bioharvest revealed the presence of clipped impurity—a compound that is uniquely associated with activatable antibodies. Due to the potential effects of off-target toxicity and decreased efficacy, it is undesirable to have significant amounts of the clipped impurity, i.e., "activated" activatable antibody that can freely bind its biological target, in a composition or pharmaceutical product. The presence of clipped variants in drug product is undesired because of the potential to impact the safety profile of the product.

Removal of clipped impurity from intact activatable antibody compositions is made challenging due to the relatively small differences between desired product and clipped impurity with respect to properties such as molecular size, structure, amino acid composition, and the fact that their amino acid sequences may be 100% identical over a majority of their respective structures. Structurally, the difference between an intact activatable antibody and the corresponding clipped impurity is the absence of all or a portion of at least one prodomain in the clipped impurity. In some embodiments, the masking moiety is a relatively short peptide sequence, for example less than 50 amino acids, less than 40, 30, 20, 15, 14, 13, 12, 11, or 10 amino acids long, and the clipped species and the intact activatable antibody may differ by approximately the number of amino acids in the masking moiety. Further, the inventors have discovered that single-arm clipped variants are the predominant clipped variant, such that the entire difference between an intact activatable antibody and a clipped variant is the absence of a portion of a single prodomain, for example the clipped variant differs from the intact activatable antibody only in that lacks a MM and a portion of a CM. Thus, the size and physicochemical properties of the intact activatable antibody and a clipped variant thereof are similar, making separation of the molecules difficult.

Figure 1B:
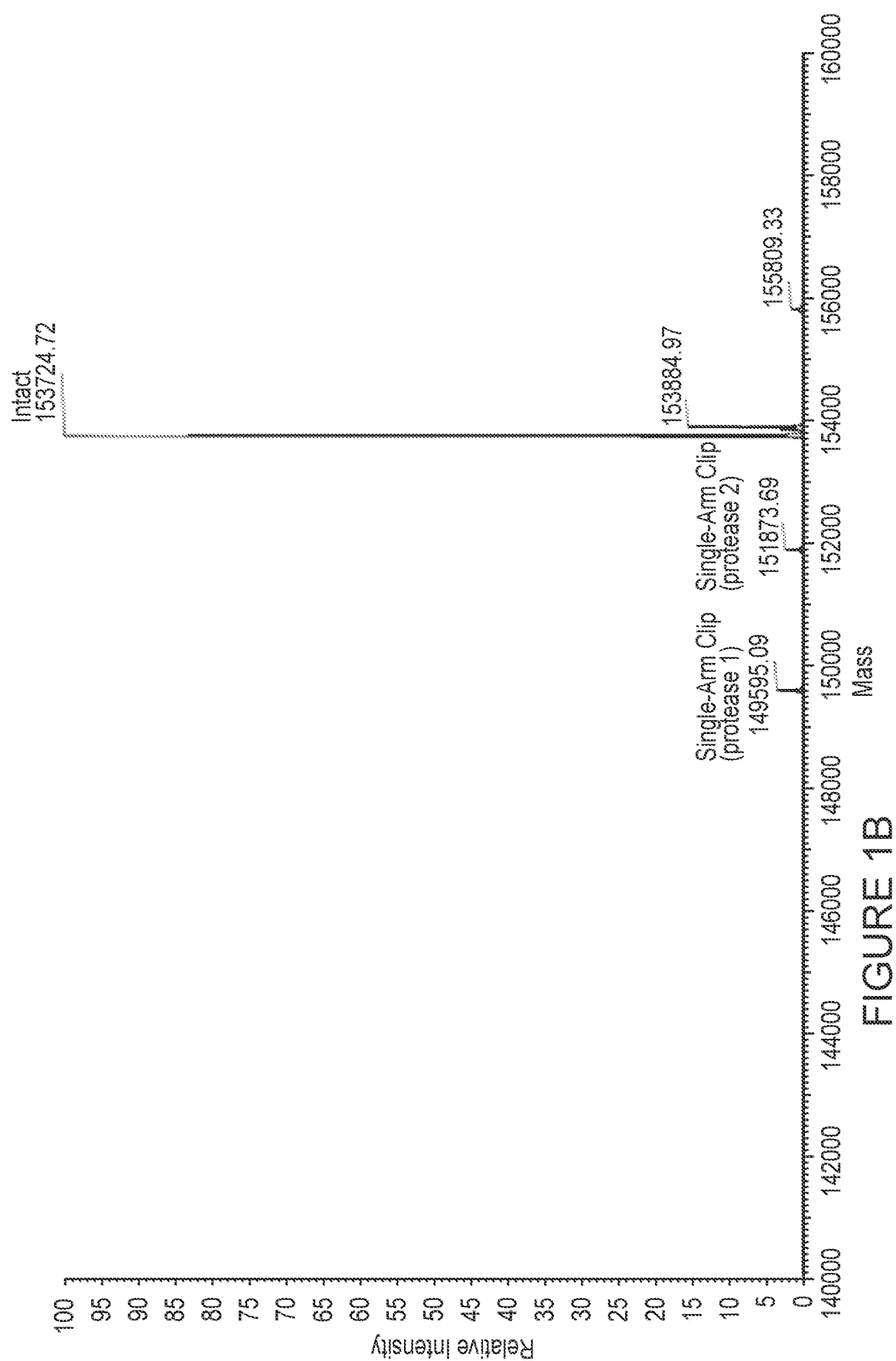
FIG. 1B depicts the results of a mass spectrophotometry analysis of a sample obtained from a bioharvest of activatable anti-PD1 antibody. The results show a single peak corresponding to the expected molecular weight for the corresponding single-arm clipped impurity. No peaks were observed at the expected molecular weights for fully clipped impurity.
Figure 2A:
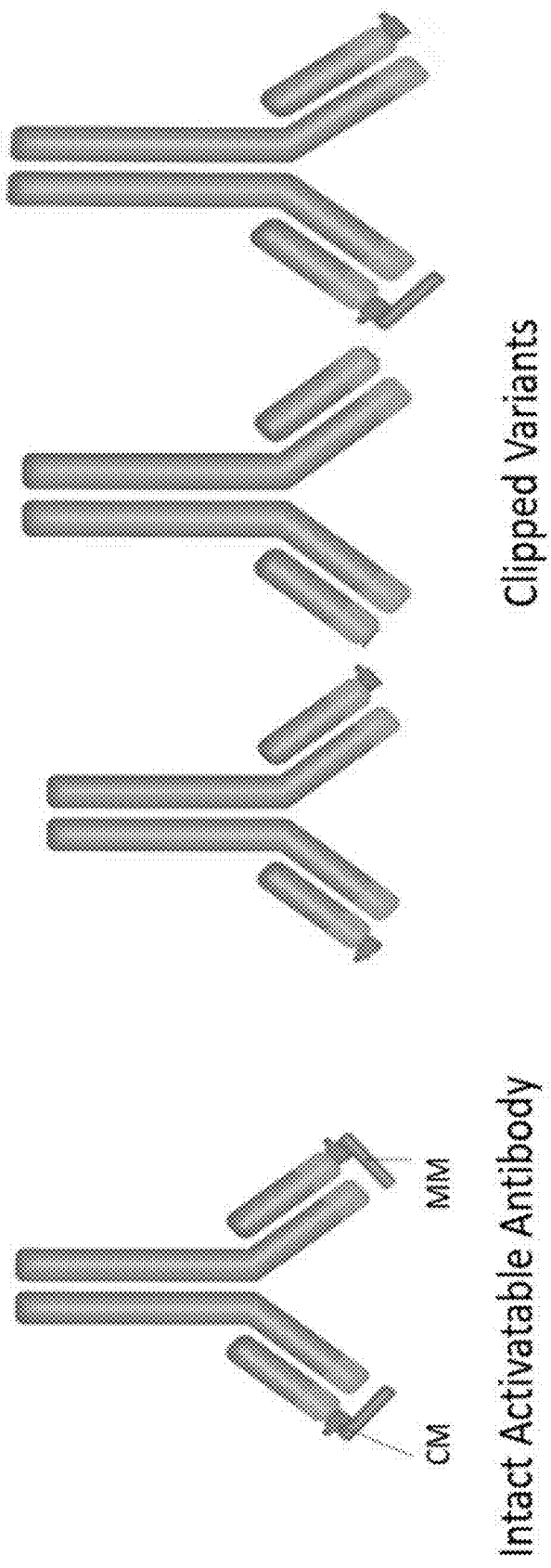
FIG. 2A schematically depicts the structures of an intact activatable antibody and clipped variants thereof.
Figure 2B:
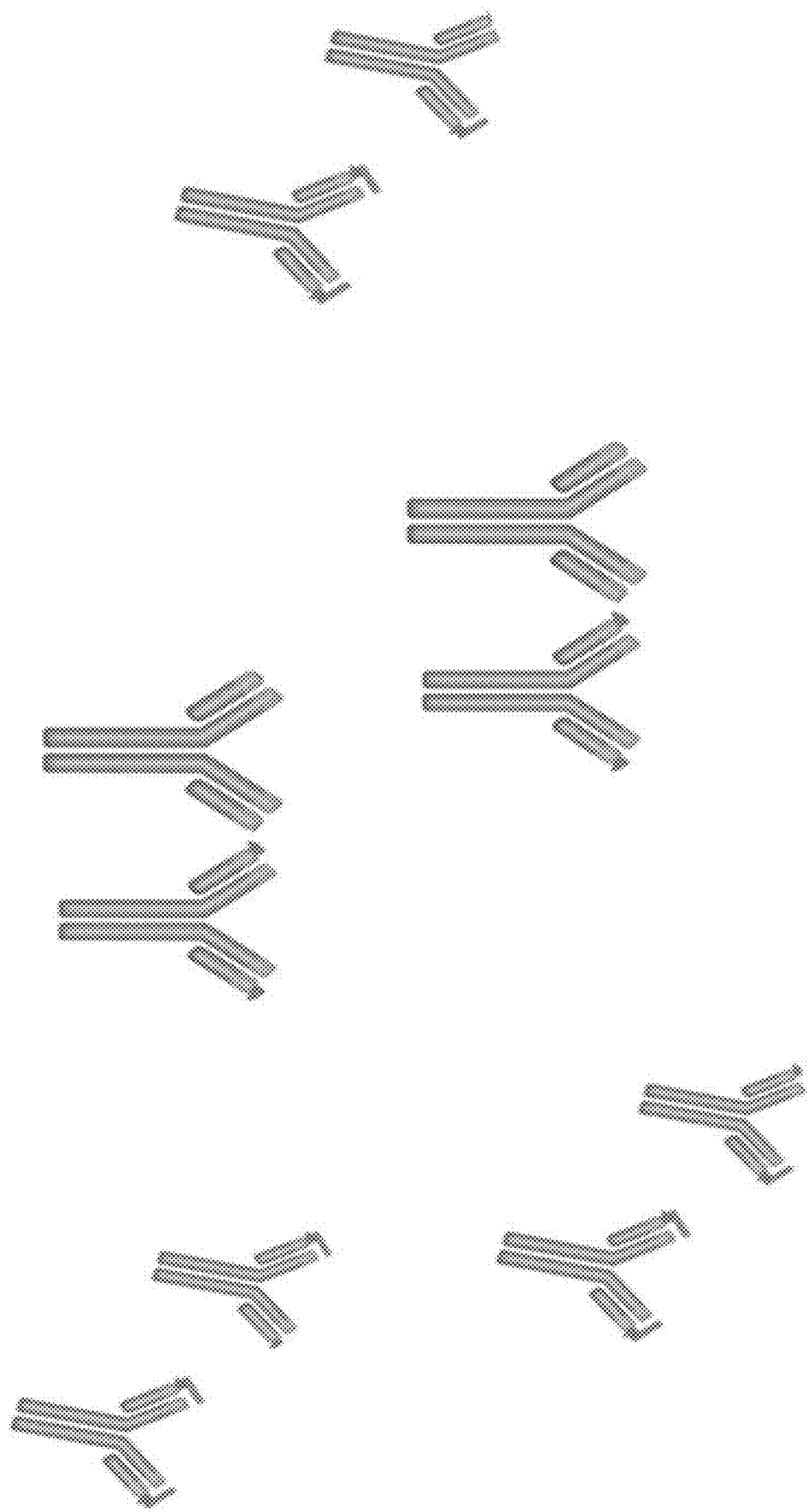
FIG. 2B schematically depicts a mixture of intact activatable antibody and clipped variants thereof as may be present in a composition prior to treatment with the method of the present disclosure.

Characterization of bioharvest compositions comprising activatable antibody having two light chains, each encoding a prodomain, and two heavy chains, revealed that all, or nearly all of the clipped impurity appears to be single-arm clipped impurity (i.e., not fully clipped impurity), as shown by the mass spectrums of three different activatable antibody compositions in FIGS. 1A-C. Thus, when an activatable antibody has more than one prodomain-encoding polypeptide, separation of intact activatable antibody and clipped impurity is exacerbated by the fact that the predominant clipped species, single-arm clipped impurity, is structurally very similar to that of the corresponding intact activatable antibody. In some aspects, the molecular weight of the clipped impurity is about 93, 94, 95, 96, 97, 98, or 99% of the molecular weight the intact activatable antibody. In some aspects, the molecular weight of the clipped prodomain-encoding polypeptide is about 93, 94, 95, 96, 97, 98, or 99% of the molecular weight of the intact prodomain-encoding polypeptide. In some aspects, the clipped impurity is about 93, 94, 95, 96, 97, 98, or 99% identical to the amino acid sequence of the intact activatable antibody.

In some aspects, a clipped variant may include 1, 2, 3, 4, or more amino acid residues of the prodomain. In some aspects, a clipped variant may include 1, 2, 3, 4, or more amino acid residues of the CM. In some aspects, a clipped variant may include 1, 2, 3, 4, or more amino acid residues of a linker. In some aspects, a clipped variant may include 1, 2, 3, 4, or more amino acid residues of a linker and the CM.

Despite this challenge, a process has been discovered that is remarkably effective at separating intact activatable antibody from corresponding clipped impurity at relatively high yield. The process for producing purified compositions of intact activatable antibody comprises:

(a) loading an aqueous feedstock comprising water, an intact activatable antibody, a clipped impurity, and a first salt onto a chromatography column,
 wherein the chromatography column comprises a stationary phase that comprises a support matrix and ligands bound thereto,
  wherein the ligands comprise a hydrophobic substituent, and
 wherein the intact activatable antibody comprises (i) at least a first antigen binding domain (AB) that has a specific binding affinity for a first biological target, and (ii) a first prodomain,
  wherein the at least first AB comprises a first antibody light variable domain (VL) and a first antibody heavy variable domain (VH),
  wherein the first prodomain comprises a first masking moiety (MM) and a first cleavable moiety (CM), and
  wherein the first AB is coupled to the first prodomain; and
(b) eluting the chromatography column with an eluent comprising water and a second salt to generate an eluate that comprises a purified composition comprising intact activatable antibody,
 wherein the eluate is substantially depleted of the clipped impurity.

Steps (a) and (b) are collectively referred to herein as the "hydrophobic chromatography process". The eluate, and thus the purified composition, are both substantially depleted of the clipped impurity. Distinct and separate peaks of intact activatable antibody and corresponding clipped impurity were observed in elution product from the chromatography column. Despite the similarity in structure between intact and clipped impurity, the compounds were readily separable on chromatography columns that relied, at least in part, on hydrophobic interactions. The intact activatable antibody-rich eluate that was generated was substantially depleted of the corresponding clipped impurity. The process is a readily scalable and highly productive process for generating highly pure compositions of intact activatable antibody at high total protein yields.

It was discovered that intact activatable antibody elutes in a distinct peak prior to the corresponding clipped impurity, and also, prior to other impurities, such as, for example, high molecular weight species ("HMWS") and host cell protein (HCP). This phenomenon was observed across a variety of aqueous feedstock compositions comprising intact activatable antibody and corresponding clipped impurity having different amino acid sequences and specificities to different biological targets, as demonstrated in the Examples. In view of the resolution and peak profiles that were achieved, in some embodiments, elution step (b) is carried out under isocratic conditions.

In many embodiments, after performing step (b), the process further comprises a column cleaning step that comprises washing the chromatography column with a cleaning agent. Often in these embodiments, the process of the present invention does not comprise a step of eluting bound corresponding clipped impurity and/or other impurities if present in the aqueous feedstock (such as, for example, HMWS, HCP, and the like) from the chromatography column with a second eluent prior to the column cleaning step. Because the impurities are substantially retained on the column after elution of the intact activatable antibody, it may be desired to carry out the cleaning step without separately eluting the impurities, thus further enhancing the highly productive nature of the process of the present invention. Suitable cleaning agents include any of a wide variety known in the art, including for example, an aqueous acid solution; an aqueous base solution, an organic solvent, a mixed organic solvent (e.g., comprising two or more different organic solvents), an aqueous mixture of one or more organic solvents, a mixture of any of the foregoing, and the like. Illustrative cleaning agents include an aqueous sodium hydroxide solution, ethanol, isopropanol, ethylene glycol, a guanidine hydrochloride solution, an acidic pepsin solution, a sodium lauroyl sarcosinate solution, and the like, as well as any combination of two or more thereof.

With regards to the stationary phase employed in the process of the present invention, any of a wide variety of known support matrix materials may be used. Illustrative support matrix materials that are suitable include a hydrophilic polymer, such as, for example, a carbohydrate (such as, for example, agarose (e.g., SEPHAROSE brand (GE Healthcare Lifesciences), Capto™ ImpRes (GE Healthcare Lifesciences), a cross-linked cellulose (e.g., Cellufine™ HIC media (Amsbio), and the like), a polymethacrylate-based resin (e.g., Macro-Prep® HIC resin (Bio-Rad, Inc.), and the like), a polystyrene-based resin (e.g., Bio-Beads™ SM-2 Resin (Bio-Rad, Inc.), and the like), silica, a synthetic co-polymer, as well as any other chromatography support matrix materials that are known in the art. The support matrix may be in any of a variety of forms, including, for example, particulate form, bead form, membrane form, and the like.

Any of a variety of known ligand species having a hydrophobic substituent may be employed in the processes of the present invention. Exemplary hydrophobic substituents include, for example, a straight chain alkyl substituent (including, for example, methyl, ethyl, n-propyl, n-butyl, n-pentyl, n-hexyl, n-heptyl, n-octyl, and the like), a branched alkyl substituent (such as, for example, i-propyl, t-butyl, and the like), an aryl substituent (such as, for example, phenyl, an alkyl-substituted phenyl, and the like), and the like, as well as any combination of two or more types of hydrophobic substituents. In some embodiments, the hydrophobic substituent comprises a $C_4$ to $C_{10}$ alkyl substituent (i.e., a $C_4$, $C_5$, $C_6$, $C_7$, $C_8$, $C_9$, or a $C_{10}$ substituent) and/or a phenyl substituent. Often, the $C_4$ to $C_{10}$ alkyl substituent is selected from the group consisting of a butyl substituent (i.e., $C_4$) or an octyl substituent (i.e., $C_8$). The hydrophobic substituents may be coupled to the support matrix via any of a variety of linkages, including, for example, O-ether, S-ether, and the like. Exemplary ligands (including —O— linker) that are suitable for use in the practice of the present invention include —O-Ph, —S—$(CH_2)_3$—$CH_3$ (—S-butyl), —O—$(CH_2)_3$—$CH_3$ (O-butyl), —O—$(CH_2)_7$—$CH_3$ (O-octyl), —O—$CH_2$—CHOH—$CH_2$—OH, —O—CH—$(CH_3)_2$, and the like. In certain embodiments, as described in more detail hereinbelow, the ligands may further comprise additional substituents that facilitate separation by interactions other than hydrophobic, such as, for example, electrostatic, hydrogen bonding, thiophilic, and the like.

In some embodiments, the stationary phase is a hydrophobic interaction chromatography (HIC) stationary phase that facilitates separation by hydrophobic interactions only. Exemplary HIC stationary phase ligands may comprise any of the hydrophobic substituents described hereinabove. In certain embodiments, the ligands comprise a substituent selected from the group consisting of phenyl, butyl, octyl, and isopropyl. HIC stationary phases are readily available commercially. In specific embodiments, the stationary phase comprises a ligand selected from the group consisting of —O-phenyl, —S—$(CH_2)_3$—$CH_3$ (i.e., —S-butyl), —O—$(CH_2)_3$—$CH_3$ (i.e., O-butyl), —O—$(CH_2)_7$—$CH_3$ (i.e., O-octyl), —O—$CH_2$—CHOH—$CH_2$—OH, —O—CH—$(CH_3)_2$, and the like, as well as any combination of two or more different ligands.

In other embodiments, the stationary phase is a multimodal chromatography (MMC) stationary phase. In these embodiments, the ligands comprise one or more hydrophobic substituents, and at least one further substituent that facilitates separation on the basis of an interaction other than hydrophobicity, such as, for example, electrostatic, hydrogen bonding, thiophilicity, and the like. Illustrative MMC stationary phases that are suitable for use in the practice of the present invention comprise ligands that have, for example, a hydrophobic substituent and one or more substituents selected from the group consisting of a sulfide substituent, a carboxyl substituent, and an amine substituent. Often, the carboxyl substituent and/or amine substituent are charged under the process conditions employed. MMC stationary phases that are suitable for use in the practice of the present invention include those having a ligand selected from the group consisting of N-benzyl methyl ethanolamine, N-benzyl methyl ethanolamine, N-benzoyl-homocysteine, N-benzoyl-homocysteine, octylamine, and the like.

The presence of a hydrophobic substituent in the immobilized ligand appeared to have a substantial impact on facilitating the separation of intact activatable antibody from clipped impurity. Separation of intact activatable antibody from clipped impurity was achieved to a high degree, using the hydrophobic chromatography process as illustrated in Examples 3 (using a HIC stationary phase), 4 (using a HIC stationary phase), and 5 (using an MMC stationary phase). In contrast, separation of intact activatable antibody from clipped impurity was not achieved using cation exchange chromatography, as described in Example 2. Likewise, the use of anion chromatography similarly did not appear to have an impact on separating intact activatable antibody from clipped impurity, as described in Examples 3-5.

The hydrophobic chromatography process is initiated by loading onto the chromatography column an aqueous feedstock comprising water, intact activatable antibody, clipped impurity, and a first salt. In some embodiments, the aqueous feedstock may comprise additional components, including additional impurities, such as, for example, one or more products of a cell culturing process step (e.g., host cell proteins, DNA, and the like), one or more residual compounds from an upstream purification unit operation (e.g., Protein A, Protein G, and the like), HMWS (e.g., aggregates of monomeric activatable antibody species present in the aqueous feedstock, and the like), low molecular weight species (LMWS), and the like.

Salts suitable for use as a first salt in the aqueous feedstock may be any salt that promotes binding of intact activatable antibody and clipped impurity to the stationary phase of the column. Suitable first salts and first salt concentrations for the aqueous feedstock and second salts and second salt concentrations for the eluent can be readily determined by performing a series of test runs using a gradient of salt concentration and identifying the salt and salt concentration that effects binding of intact activatable antibody to the stationary phase while allowing impurities to either wash through the stationary phase or remain bound to the stationary phase, and identifying a second salt and salt concentration that effects selective elution of the desired intact activatable antibody from the stationary phase. In some embodiments, the first salt and the second salt are the same salt. In other embodiments, the first salt and the second salt are different salts. The first and/or second salt may each independently also comprise a mixture of salt species.

Illustrative first salts and second salts each independently comprise an anion selected from the group consisting of $PO_4^{3-}$, $SO_4^{2-}$, $OH^-$, $HPO_4^{2-}$, $CH_3COO^-$ (acetate ion), citrate ion, $F^-$, $Cl^-$, $Br^-$, $H_2PO_4^-$, $I^-$, $NO_3^-$, $ClO_4^-$, $SCN^-$, an amino acid anion, and the like. In some embodiments, the first salt and the second salt may each independently comprise a cation selected from the group consisting of $N(CH_3)_4^+$, $NH_4^+$, $Cs^+$, $Rb^+$, $K^+$, $Na^+$, $H^+$, $Ca^+$, $Mg^{2+}$, $Al^{3+}$, an amino acid cation, and the like. The first salt may be introduced into an aqueous composition comprising the intact activatable antibody and the corresponding clipped impurity just prior to the hydrophobic chromatography process step, or it may be introduced in connection with a process step upstream of the hydrophobic chromatography process step (e.g., in an intervening unit operation as described hereinbelow). In this latter situation, additional first salt may be optionally added to the composition and/or the composition may be diluted to accommodate desired load conditions for the column.

When the chromatography column comprises a HIC stationary phase, the first salt typically exhibits kosmotropic (salting out) behavior. Such salts can be readily identified, for example, from the Hofmeister series of ions. See, e.g., Tadeo, et al., *Biophysical Journal* (2009) 97:2595 and Hyde, et al., *Org. Process Res. Dev.* (2017) 21:1355, both of which are incorporated herein by reference in their entireties. In some embodiments, the first salt and the second salt each independently comprise an anion and/or cation that is more strongly kosmotropic than chaotropic. In certain of these embodiments, the first salt and the second salt each independently comprise an anion selected from the group consisting of $PO_4^{3-}$, $SO_4^{2-}$, $OH^-$, $HPO_4^{2-}$, $F^-$, $CH_3COO^-$ (acetate ion), citrate ion, an amino acid anion, and $Cl^-$. In other embodiments, the first salt and the second salt each independently comprise an anion selected from the group consisting of $PO_4^{3-}$, $SO_4^{2-}$ and $HPO_4^{2-}$.

In certain of these embodiments, the first salt and the second salt each independently comprise a cation selected from the group consisting of $N(CH_3)_4^+$, $NH_4^+$, $Cs^+$, $Rb^+$, $K^+$, $Na^+$, $H^+$, $Ca^+$, $Mg^{2+}$, $Al^{3+}$, and an amino acid cation. In some embodiments, the first salt and the second salt each independently comprise a cation selected from the group consisting of $NH_4^+$, $K^+$, $Na^+$, $Li^+$, and $Mg^{2+}$. In certain embodiments, the first salt and the second salt each independently comprise a cation selected from the group consisting of $NH_4^+$, $K^+$, and $Na^+$. In some embodiments, the first salt and the second salt each independently comprise a cation selected from the group consisting of $NH_4^+$, $K^+$, and $Na^+$, and an anion selected from the group consisting of $PO_4^{3-}$, $SO_4^{2-}$, $OH^-$, $HPO_4^{2-}$, $CH_3COO^-$ (acetate ion), citrate ion, $F^-$, $Cl^-$, $Br^-$, $H_2PO_4^-$, $I^-$, $NO_3^-$, $ClO_4^-$, and $SCN^-$.

In some embodiments, the first salt and the second salt are each independently selected from the group consisting of $(NH_4)_2SO_4$, $Na_2SO_4$, $Na_3PO_4$, $K_3PO_4$, NaCl, KCl, and $CH_3COONH_4$. In certain embodiments, the first salt and the second salt are each independently selected from the group consisting of $(NH_4)_2SO_4$, $Na_2SO_4$, $Na_3PO_4$, and $K_3PO_4$. In other embodiments, the first salt and the second salt are each independently selected from the group consisting of $(NH_4)_2SO_4$ and $Na_2SO_4$. In certain embodiments, at least one of the first salt and the second salt comprises $(NH_4)_2SO_4$. In some of these embodiments, both the first salt and the second salt comprise $(NH_4)_2SO_4$. In other embodiments, at least one of the first salt and the second salt comprises $Na_2SO_4$. In some of these embodiments, both the first salt and the second salt comprise $Na_2SO_4$.

When the chromatography column comprises a HIC stationary phase, the eluent is generally less polar than the aqueous feedstock. In some embodiments, the first salt concentration (i.e., in the aqueous feedstock) is greater than the second salt concentration (i.e., in the eluent). For example, the first salt concentration may be about 1.5× greater, about 2× greater, about 3× greater, about 4× greater, about 5× greater, about 6× greater, about 7× greater, about 8× greater, about 9× greater, or about 10× greater than the second salt concentration. For example, the first salt may comprise about 1.5 M ammonium sulfate and the second salt may comprise about 0.25 M ammonium sulfate (about 6× greater concentration of the first salt than the second salt). When it is desired to use a second salt that is different from the first salt, the second salt is typically lower in kosmotropic strength as compared to the first salt. Cations and anions having greater or lesser kosmotropic strength can be readily identified in accordance with the Hofmeister series of ionic strength. See, e.g., Tadeo, et al., *Biophysical Journal* (2009) 97:2595 and Hyde, et al., *Org. Process Res. Dev.* (2017) 21:1355, both of which are incorporated herein by reference in their entireties. In some embodiments, the eluent further comprises a water miscible organic solvent, such as, for example, an alcohol, a diol, a polyol, and the like.

When the chromatography column comprises an MMC stationary phase, the first salt typically exhibits chaotropic (salting in) behavior. As with the salts employed in connection with a HIC stationary phase, salts suitable for use in connection with an MMC-based process can also be readily identified from the Hofmeister series of ions. In some embodiments, the first and second salt each independently comprise an anion and/or cation that is more strongly chaotropic than kosmotropic. See, e.g., Tadeo, et al., *Biophysical Journal* (2009) 97:2595 and Hyde, et al., *Org. Process Res. Dev.* (2017) 21:1355, both of which are incorporated herein by reference in their entireties. In certain of these embodiments, the first salt and the second salt each independently comprise an anion selected from the group consisting of $Cl^-$, $Br^-$, $H_2PO_4^-$, $I^-$, $NO_3^-$, $ClO_4^-$, an amino acid anion, and $SCN^-$. In some of these embodiments, the first salt and the second salt each independently comprise an anion selected from the group consisting of $Cl^-$, $Br^-$, $H_2PO_4^-$, $I^-$, $NO_3^-$, an amino acid anion, and $ClO_4^-$, and $SCN^-$.

In certain embodiments, the first salt and the second salt each independently comprise a cation selected from the group consisting of $N(CH_3)_4^+$, $NH_4^+$, $Ba^+$, $Ca^{2+}$, $Mg^{2+}$, $Cs^+$, $Rb^+$, $K^+$, $Na^+$, and an amino acid cation. In some embodiments, the cation is selected from the group consisting of $N(CH_3)_4^+$, $NH_4^+$, $Ca^{2+}$, $Mg^{2+}$, $K^+$, $Na^+$, and an amino acid cation. When an amino acid cation is employed, it is often an arginine cation (e.g., with a positively charged guanidino moiety).

Illustrative first salts include, for example, arginine chloride or arginine hydrochloride, NaCl, and the like. When the chromatography column comprises an MMC stationary phase, the first salt and the second salt are often the same salt. In these embodiments, the eluent typically comprises a concentration of the salt that is greater than the concentration of the salt in the aqueous feedstock. For example, the eluent (second salt) salt concentration may be about 1.5× greater, about 2× greater, about 3× greater, about 4× greater, about 5× greater, about 6× greater, about 7× greater, about 8× greater, about 9× greater, or about 10× greater than the feedstock (first salt) salt concentration. When the first salt and the second salt are different, a second salt is often selected that is higher in chaotropic strength as compared to the first salt. Cations and anions have greater or lesser chaotropic strength can be readily identified in accordance with the Hofmeister series of ionic strength. See, e.g., Tadeo, et al., *Biophysical Journal* (2009) 97:2595 and Hyde, et al., *Org. Process Res. Dev.* (2017) 21:1355, both of which are incorporated herein by reference in their entireties. In certain embodiments where the first salt and the second salt are different, the eluent comprises both the first salt and the second salt. In some aspects, the first salt may comprise about 30 mM sodium chloride as the only salt, and the second salt may comprise about 30 mM sodium chloride and about 90 mM arginine hydrochloride.

The aqueous feedstock and eluent may each independently also comprise one or more buffering agents. Suitable buffering agents include one or more salts, such as, for example, any of those listed hereinabove as a suitable first salt; an acid, such as, for example, 2-(N-morpholino)ethanesulfonic acid (MES), (3-(N-morpholino)propanesulfonic acid) (MOPS), (4-(2-hydroxyethyl)-1-piperazineethanesulfonic acid) (HEPES), hydrogen chloride, and the like; and/or a base, such as, for example, sodium hydroxide, potassium hydroxide, and the like.

In certain embodiments, the clipped impurity consists of single-arm clipped impurity. In some embodiments in which the intact activatable antibody comprises multiple AB s and correspondingly, multiple prodomains, the clipped impurity may comprise a mixture of clipped impurity species. In some of these embodiments, the mixture of clipped impurity species comprises single-arm clipped impurity and fully clipped impurity. In still other embodiments in which the intact activatable antibody comprises multiple ABs and correspondingly, multiple prodomains, the clipped impurity consists essentially of single-arm clipped impurity. In some of these embodiments, the clipped species consists of single-arm clipped impurity. Single-arm clipped impurity and fully clipped impurity can be readily determined by mass spectrometry.

In some embodiments, the aqueous feedstock comprises a pH in the range of from about 5.0 to about 8.0, or from about 5.0 to about 7.5, or from about 5.0 to about 7.0, or from about 5.5 to about 6.5, or from about 5.7 to 6.3, or from about 5.8 to 6.2, or from about 5.6 to about 6.0. The temperature at which the loading and eluting steps are carried out may be the same or different. In some embodiments, the loading and eluting steps are each independently carried out at a temperature in the range of from about 10° C. to about 30° C., or in the range of from about 15° C. to about 30° C., or in the range of from about 15° C. to about 29° C., or in the range of from about 15° C. to about 28° C., or in the range of from about 15° C. to about 27° C., or in the range of from about 15° C. to about 26° C., or in the range of from about 15° C. to about 25° C., or in the range of from about 16° C. to about 25° C., or in the range of from about 17° C. to about 25° C., or in the range of from about 18° C. to about 25° C. Typically, the loading and eluting steps are carried out at a temperature in the same temperature range. Often the target temperature is about the same for both the loading and eluting steps. In some embodiments, it may be desired to carry out the eluting step at a temperature that is different from the temperature at which the loading step is carried out. In certain embodiments, it may be desired to carry out the process steps at a temperature that is higher or lower than the endpoints of the ranges described hereinabove. For example, when a HIC stationary phase is employed, a higher temperature employed during the loading step may increase hydrophobic interactions with the column and a lower temperature during the eluting step may encourage release of components from the column by decreasing hydrophobic interactions with the column.

The chromatography column may be pre-conditioned to have a pH, first salt concentration, and temperature that is about the same as that of the aqueous feedstock. This may be accomplished by loading sufficient quantities (e.g., one or more column volumes) of buffer having the same pH, first salt concentration, and/or temperature as the aqueous feedstock into the chromatography column until target conditions are achieved in the column.

After the loading step, the column may be washed with a washing buffer to remove non-binding components from the column before the elution step. In some embodiments, the washing buffer comprises a salt at about the same concentration or a concentration that is higher than the concentration of first salt in the aqueous feedstock and is often at about the same pH as the aqueous feedstock.

It has been discovered that aqueous feedstocks comprising intact activatable antibody and impurities can be purified at high total protein yields using the processes described herein. In some embodiments, the yield of total protein in the eluate is at least about 60%, at least about 65%, at least about 70%, or at least about 71%, or at least about 72%, or at least about 73%, or at least about 74%, or at least about 75%, or at least about 76%, or at last about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, as determined by absorbance at a wavelength of 280 nm. An illustrative absorbance assay for determining total protein is described in Example 1, herein below.

The hydrophobic chromatography process is highly effective at removing clipped impurity from the process stream (i.e., collectively, the stream of aqueous feedstock into the hydrophobic process and the stream of eluant out of the hydrophobic process). In some embodiments, the level of reduction in relative quantity of clipped impurity in the aqueous feedstock compared to the relative quantity of clipped impurity in the eluate is at least about 2-fold, at least about 3-fold, at least about 4-fold, at least about 5-fold, at least about 6-fold, at least about 7-fold, or at least about 8-fold, or at least about 9-fold, or at least 10-fold, or at least about 15-fold, or at least about 20-fold, as measured by reducing SDS-capillary gel electrophoresis (SDS-cGE). In some embodiments, no clipped impurity is detected in the eluate. The term "relative quantity of clipped impurity" refers herein to "% clipped impurity" is as defined hereinbelow.

As used herein, the phrase "level of reduction" or "reducing" (and grammatical variants thereof), when used in connection with an impurity, such as clipped impurity, HCP, HWMS, and the like, refers to the extent of reduction in quantity of the impurity, as determined by comparing the quantity of impurity in the aqueous feedstock to the quantity of impurity in the eluate. The level of reduction in impurity can be represented in terms of a ratio (or equivalently, as a fold reduction) or in terms of a percent reduction.

When clipped impurity is present in the eluate, the fold reduction in level of clipped impurity is determined by the following formula:

$$\text{Fold Reduction of clipped impurity} = \frac{(\% \text{ clipped impurity})_{aqueous\ feedstock}}{(\% \text{ clipped impurity})_{eluate}}$$

where "% clipped impurity" in each of the aqueous feed and eluate is determined according to the following formula:

$$(\% \text{ clipped impurity})_{aqueous\ feedstock} = \frac{(\% \text{ Peak Area}_{clipped})_{aqueous\ feedstock}}{(\% \text{ Peak Area}_{clipped} + \% \text{ Peak Area}_{intact})_{aqueous\ feedstock}} \times 100$$

where:

$$(\% \text{ Peak Area}_{clipped})_{aqueous\ feedstock} = \frac{\left(\begin{array}{c}\text{Peak Area of clipped}\\ \text{prodomain-encoding polypeptide}\end{array}\right)_{aqueous\ feedstock}}{\left(\begin{array}{c}\text{Total Peak Area corresponding}\\ \text{to all species detected}\end{array}\right)_{aqueous\ feedstock}} \times 100, \text{ and}$$

$$(\% \text{ Peak Area}_{intact})_{aqueous\ feedstock} = \frac{\left(\begin{array}{c}\text{Peak Area of intact}\\ \text{prodomain-encoding polypeptide}\end{array}\right)_{aqueous\ feedstock}}{\left(\begin{array}{c}\text{Total Peak Area corresponding}\\ \text{to all species detected}\end{array}\right)_{aqueous\ feedstock}} \times 100; \text{ and}$$

$$(\% \text{ clipped impurity})_{eluate} = \frac{(\% \text{ Peak Area}_{clipped})_{eluate}}{(\% \text{ Peak Area}_{clipped} + \% \text{ Peak Area}_{intact})_{eluate}} \times 100 \text{ where:}$$

$$(\% \text{ Peak Area}_{clipped})_{eluate} = \frac{\left(\begin{array}{c}\text{Peak Area of clipped}\\ \text{prodomain-encoding polypeptide}\end{array}\right)_{eluate}}{\left(\begin{array}{c}\text{Total Peak Area corresponding}\\ \text{to all species detected}\end{array}\right)_{eluate}} \times 100, \text{ and}$$

$$(\% \text{ Peak Area}_{intact})_{eluate} = \frac{\left(\begin{array}{c}\text{Peak Area of intact}\\ \text{prodomain-encoding polypeptide}\end{array}\right)_{eluate}}{\left(\begin{array}{c}\text{Total Peak Area corresponding}\\ \text{to all species detected}\end{array}\right)_{eluate}} \times 100.$$

In the above formulae, the clipped impurity is quantified in terms of the polypeptide that is impacted by clipping, i.e., the prodomain-encoding polypeptide. The prodomain-encoding polypeptide may be an antibody light chain, an antibody heavy chain, an scFv, and the like, depending on whether those polypeptides also encode the prodomain. For example, where the prodomain is coupled to an antibody light chain, the relative quantity of clipped impurity (i.e., % clipped impurity) is calculated by dividing the % Peak Area of the light chain clipped impurity in the eluate by the sum of: a) the % Peak Area of the light chain clipped impurity in the eluate and b) the % PeakArea of the intact light chain in the eluate. Peak areas for clipped prodomain-encoding polypeptide and intact prodomain-encoding polypeptide are readily determined by a reducing SDS-cGE assay, such as the assay described in Example 1.

Thus, in these embodiments, the ratio of % clipped impurity in the aqueous feedstock to % clipped impurity in the eluate is, correspondingly, at least about 2, or at least about 3, or at least about 4, or at least about 5, or at least about 6, or at least about 7, or at least about 8, or at least about 9, or at least about 10, or at least about 15, or at least about 20, as measured by reducing SDS-capillary gel electrophoresis (SDS-cGE) assay, such as the assay described in Example 1.

In some embodiments, the relative quantity of clipped impurity in the aqueous feed compared to the relative quantity of clipped impurity in the eluate corresponds to a level of reduction that is at least about 50%, or at least about 55%, or at least about 60%, or at least about 65%, or at least about 70%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%, as determined by reducing SDS-cGE, such as the assay described in Example 1. Percent (%) reduction of clipped impurity is determined by the following formula:

% reduction of clipped impurity =

$$\frac{(\% \text{ clipped impurity})_{aqueous\ feedstock} - (\% \text{ clipped impurity})_{eluate}}{(\% \text{ clipped impurity})_{Aqueous\ Feedstock}} \times 100,$$

where % clipped impurity for each of the aqueous feedstock and eluate are as defined above.

In some embodiments, the eluate comprises less than about 50%, or less than about 45%, or less than about 40%, or less than about 35%, or less than about 30%, or less than about 25%, or less than about 24%, or less than about 23%, or less than about 22%, or less than about 21%, or less than about 20%, or less than about 19%, or less than about 18%, or less than about 17%, or less than about 16%, or less than about 15%, or less than about 14%, or less than about 13%, or less than about 12%, or less than about 11%, or less than about 10% of the relative quantity of clipped impurity present in the aqueous feedstock. Relative quantity of clipped impurity in the eluate as a percent of clipped impurity in the aqueous feedstock is determined as follows:

$$\frac{(\% \text{ clipped impurity})_{eluate}}{(\% \text{ clipped impurity})_{Aqueous\ Feedstock}} \times 100,$$

where % clipped impurity for each of the aqueous feedstock and eluate are as defined above.

In some embodiments, the eluate comprises less than about 15%, or less than about 14%, or less than about 13%, or less than about 12%, or less than about 11%, or less than about 10%, or less than about 10%, or less than about 9%, or less than about 8%, or less than about 7%, or less than about 6% of the relative quantity of quantity of clipped impurity present in the aqueous feedstock, as measured by reducing SDS-cGE. In some embodiments, the eluate comprises a range of about 2% to 15%, or about 3% to about 15%, or about 4% to about 15%, or about 5% to about 15%, or about 2% to about 10%, or about 3% to about 10% of the relative quantity of quantity of clipped impurity present in the aqueous feedstock, as measured by reducing SDS-cGE.

The hydrophobic process is thus effective at generating an eluate (and corresponding purified composition of intact activatable antibody) having relatively low levels of clipped impurity. In certain embodiments, the eluate (and corresponding purified composition of intact activatable antibody) comprises a relative quantity of clipped impurity in the range of from about 0.1% to about 15% clipped impurity, or from about 0.1% to about 10% clipped impurity, or from about 0.1% to about 10% clipped impurity, or from about 0.1% to about 5% clipped impurity, or from about 0.1% to about 4% clipped impurity, or from about 0.1% to about 3% clipped impurity, or from about 0.1% to about 2% clipped impurity, or from about 0.1% to about 1% clipped impurity, as determined by reducing SDS-cGE. Percent clipped impurity is calculated as defined above. Percent clipped impurity may be measured in a sample taken from the eluate immediately after a separation procedure is completed, and may be either analyzed by SDS-cGE immediately or frozen until analyzed by SDS-cGE.

In some embodiments, the eluate (and corresponding purified composition of intact activatable antibody) comprises less than about 5%, or less than about 4%, or less than about 3%, or less than about 2%, or less than about 1%, or less than about 0.9%, or less than about 0.8%, or less than about 0.7%, or less than about 0.6%, or less than about 0.5% clipped impurity, as measured by reducing SDS-cGE. In other embodiments, the eluate comprises less than about 2%, or less than about 1%, or less than about 0.9%, or less than about 0.8%, or less than about 0.7%, or less than about 0.6%, or less than about 0.5% clipped impurity, as measured by reducing SDS-cGE. In certain embodiments, the eluate (and corresponding purified composition of intact activatable antibody) comprises no detectable clipped impurity.

In some embodiments, the aqueous feedstock comprises one or more further impurity selected from the group consisting of host cell protein (HCP), high molecular weight species (HMWS), and a combination thereof. The processes of the present invention are effective at substantially reducing the quantities of these impurities as well. HCP and HMWS both appear to be largely retained in the column along with clipped impurity during the elution step.

In certain embodiments, the further impurity is HCP. In these embodiments, the process is highly effective at removing HCP from the process stream. In some embodiments, the level of reduction effected by the hydrophobic chromatography process is at least about 3-fold, or at least about 4-fold-, or at least about 5-fold, or at least about 6-fold, or at least about 7-fold, or at least about 8-fold, or at least about 9-fold, or at least about 10-fold, on a parts per million (ppm) basis, as determined by a corresponding HCP ELISA assay. Fold-reduction in HCP is determined by dividing the quantity of HCP in the aqueous feed by the quantity of HCP in the eluate on a ppm basis, as determined by a corresponding HCP ELISA assay, i.e., $$\frac{(HCP \text{ in ppm})_{Aqueous\ Feedstock}}{(HCP \text{ in ppm})_{Eluate}}.$$

The quantity of HCP can be readily determined using Host Cell Protein ELISA kits that are commercially available for a number of different host cells, including, for example, mammalian, yeast, bacterial, and transgenic host species. The term "corresponding HCP ELISA assay" is used herein to refer to a host cell protein ELISA assay that employs antibodies to proteins associated with the host cell used to produce the activatable antibody. Correspondingly, in some embodiments, the ratio of quantity of HCP in the aqueous feedstock to the quantity of HCP in the eluate is at least about 4, or at least about 5, or at least about 6, or at least about 7, or at least about 8, or at least about 9, or at least about 10, on a parts per million (ppm) basis, as determined by a corresponding HCP ELISA assay.

In terms of percent (%) reduction in HCP, in certain embodiments, the level of reduction is at least about 50%, or is at least about 55%, or is at least about 60%, or is at least about 65%, or is at least about 70%, or is at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, on a ppm basis, as determined by a corresponding HCP ELISA assay. Percent reduction of HCP is determined by the formula:

$$\frac{[(\text{ppm } HCP)_{aqueous\ feedstock} - (\text{ppm } HCP)_{eluate}]}{(\text{ppm } HCP)_{aqueous\ feedstock}} \times 100.$$

Correspondingly, in some embodiments, the eluate comprises less than about 50%, or less than about 45%, or less than about 40%, or less than about 35%, or less than about 25%, or less than about 24%, or less than about 23%, or less than about 22%, or less than about 21%, or less than about 20%, or less than about 19%, or less than about 18%, or less than about 17%, or less than about 16%, or less than about 15%, or less than about 14%, or less than about 13%, or less than about 12%, or less than about 11%, or less than about 10% of the HCP present in the aqueous feedstock. The relative quantity of HCP in the eluate as a percent of HCP present in the aqueous feedstock is determined by the formula:

$$\frac{(\text{ppm } HCP)_{eluate}}{(\text{ppm } HCP)_{aqueous\ feedstock}} \times 100.$$

In some embodiments, the eluate (and corresponding purified composition of intact activatable antibody) comprises less than about 150 ppm, or less than about 140 ppm, or less than about 130 ppm, or less than about 120 ppm, or less than about 110 ppm, or less than about 100 ppm, or less than about 90 ppm, or less than about 80 ppm, or less than about 70 ppm, or less than about 60 ppm, or less than about 50 ppm, or less than about 45 ppm, or less than about 40 ppm, or less than about 35 ppm, or less than about 30 ppm, or less than about 25 ppm, or less than about 20 ppm, or less than about 15 ppm, or less than about 10 ppm HCP, as measured by a corresponding HCP ELISA. In certain embodiments, the eluate (and corresponding purified composition of intact activatable antibody) comprises no detectable HCP.

In other embodiments, the eluate (and corresponding composition of purified activatable antibody) comprises a quantity of HCP in the range of from about 0.5 ppm HCP to about 150 ppm HCP, or from about 0.5 ppm HCP to about 140 ppm HCP, or 0.5 ppm HCP to about 130 ppm HCP, or from about 0.5 ppm HCP to about 120 ppm, or from about 0.5 ppm HCP to about 110 ppm, or from about 0.5 ppm HCP to about 100 ppm HCP, or from about 0.5 ppm HCP to about 90 ppm HCP, or from about 0.5 ppm HCP to about 90 ppm HCP, or from about 0.5 ppm HCP to about 80 ppm HCP, or from about 0.5 ppm HCP to about 70 ppm HCP, or from about 0.5 ppm HCP to about 60 ppm HCP, or from about 0.5 ppm to about 50 ppm HCP, or from about 0.5 ppm HCP to about 45 ppm HCP, or from about 0.5 ppm HCP to about 40 ppm HCP, or from about 0.5 ppm HCP to about 40 ppm HCP, or from about 0.5 ppm HCP to about 35 ppm HCP, or from about 0.5 ppm HCP to about 30 ppm HCP, or from about 1 ppm HCP to about 25 ppm HCP, or from about 1 ppm HCP to about 20 ppm HCP, or from about 0.5 ppm HCP to about 15 ppm HCP, or from about 0.5 ppm HCP to about 10 ppm HCP.

In certain embodiments, the eluate (and corresponding purified composition of activatable antibody) comprises a quantity of HCP in the range of from about 1 ppm HCP to about 150 ppm HCP, or from about 1 ppm HCP to about 140 ppm HCP, or 1 ppm HCP to about 130 ppm HCP, or from about 1 ppm HCP to about 120 ppm, or from about 1 ppm HCP to about 110 ppm, or from about 1 ppm HCP to about 100 ppm HCP, or from about 1 ppm HCP to about 90 ppm HCP, or from about 1 ppm HCP to about 90 ppm HCP, or from about 1 ppm HCP to about 80 ppm HCP, or from about 1 ppm HCP to about 70 ppm HCP, or from about 1 ppm HCP to about 60 ppm HCP, or from about 1 ppm to about 50 ppm HCP, or from about 1 ppm HCP to about 45 ppm HCP, or from about 1 ppm HCP to about 40 ppm HCP, or from about 1 ppm HCP to about 40 ppm HCP, or from about 1 ppm HCP to about 35 ppm HCP, or from about 1 ppm HCP to about 30 ppm HCP, or from about 1 ppm HCP to about 25 ppm HCP, or from about 1 ppm HCP to about 20 ppm HCP, or from about 1 ppm HCP to about 15 ppm HCP, or from about 1 ppm HCP to about 10 ppm HCP.

In other embodiments, the further impurity is HMWS, either alone or in combination with HCP. HMWS can be detected and quantified by size exclusion (SE)-HPLC. An illustrative SE-HPLC assay is described in Example 1. High molecular weight species (HMWS) is detected to the left side of the main peak on the chromatogram. In these embodiments, the hydrophobic chromatography process is highly effective at removing HMWS from the process stream. In some embodiments, the level of reduction in quantity of HMWS effected by the hydrophobic chromatography process is at least about 2-fold, or at least about 3-fold, or at least about 4-fold, or at least about 5-fold, where HMWS is quantified by size exclusion (SE)-HPLC. An exemplary SE-HPLC assay is described in Example 1. Fold reduction of HMWS, and correspondingly, ratio of quantity of HMWS in the aqueous feedstock to quantity of HMWS in the eluate, are both determined by the formula:

$$\frac{(\%\ \text{Peak area } HMWS)_{aqueous\ feedstock}}{(\%\ \text{Peak area } HMWS)_{eluate}}$$

where:
(% Peak area HMWS)$_{aqueous\ feedstock}$ is the sum of all peaks corresponding to HMWS in the aqueous feedstock divided by the total of all peak area (i.e., total peak area), as determined by SE-HPLC assay; and
(% Peak area HMWS)$_{eluate}$ is the sum of all peaks corresponding to HMWS in the eluate divided by the total of all peak area (total peak area), as determined by SE-HPLC.

Thus, in these embodiments, the ratio of quantity of HMWS in the aqueous feedstock to the quantity of HMWS in the eluate is, correspondingly, at least about 2, or at least about 3, or at least about 4, or at least about 5, where quantity of HMWS is determined by SE-HPLC.

In some embodiments, the level of reduction of HMWS effected by the hydrophobic chromatography process in terms of percent (%) reduction of HMWS is at least about 50%, or is at least about 55%, or is at least about 60%, or is at least about 65%, or is at least about 70%, or is at least about 75%, or at least about 76%, or is at least about 77%, or is at least about 78%, or is at least about 79%, or is at least about 80%, or is at least about 81%, or is at least about 82%, or is at least about 83%, or is at least about 84%, or is at least about 85%, or is at least about 86%, or is at least about 87%, or is at least about 88%, or is at least about 89%, or is at least about 90%, or is at least about 91%, or is at least about 92%, or is at least about 93%, or is at least about 94%, or is at least about 95%, or is at least about 96%, or is at least about 98%, or is at least about 99%, as determined by SE-HPLC. Percent reduction of HMWS is determined according to the following formula:

$$\frac{\left[\begin{array}{c}(\%\ \text{Peak Area } HMWS)_{aqueous\ feedstock} - \\ (\%\ \text{Peak Area } HMWS)_{eluate}\end{array}\right]}{(\%\ \text{Peak Area } HMWS)_{aqueous\ feedstock}} \times 100$$

where % Peak Area HMWS for the aqueous feedstock and eluate are defined hereinabove.

In some embodiments, the relative quantity of HMWS in the eluate as a percent of HMWS present in the aqueous feedstock is less than about 50%, or less than about 45%, or less than about 40%, or less than about 35%, or less than about 25%, or less than about 30%, or less than about 25%, or less than about 20%, or less than about 15%, or less than about 15% of the HMWS present in the aqueous feedstock, as determined by SE-HPLC. The relative quantity of HMWS in the eluate as a percent of HMWS present in the aqueous feedstock is computed as:

$$\frac{(\% \text{ Peak Area } HMWS)_{eluate}}{(\% \text{ Peak Area } HMWS)_{aqueous\ feedstock}} \times 100$$

where % Peak Area HMWS for the aqueous feedstock and eluate are defined hereinabove.

In some embodiments, the eluate (and corresponding purified composition of intact activatable antibody) comprises less than about 5%, or less than about 4%, or less than about 3%, or less than about 2%, or less than about 1% HMWS, as determined by SE-HPLC, where % HMWS corresponds to (% Peak Area HMWS)$_{eluate}$ and is determined as described above.

In other embodiments, the eluate (and corresponding purified composition of intact activatable antibody) comprises less than about 3%, or less than about 2%, or less than about 1% HMWS. In some embodiments, the eluate comprises less than about 2%, or less than about 1% HMWS.

In some embodiments, the eluate (and corresponding purified composition of intact activatable antibody) comprises a quantity of HMWS in the range of from about 0.1%, 0.2%, or 0.3% HMWS to about 5% HMWS, or from about 0.2% HMWS to about 4% HMWS, or from about 0.2% HMWS to about 3% HMWS, or from about 0.2% HMWS to about 2% HMWS, or from about 0.2% HMWS to about 1% HMWS, as determined by SE-HPLC, where % is determined on the basis of total peak area. In certain embodiments, the eluate (and corresponding purified composition of intact activatable antibody) comprises no detectable HMWS.

In some embodiments of the processes described herein, the aqueous feedstock comprises greater than about 0.5% clipped impurity, or greater than about 0.6%, or greater than about 0.7%, or greater than about 0.8%, or greater than about 0.9%, or greater than about 1%, or greater than about 1.5%, or greater than about 2%, or greater than about 2.5%, or greater than about 3%, or greater than about 3.5%, or greater than about 4%, or greater than about 4.5%, or greater than about 5%, or greater than about 5.5%, or greater than about 6%, or greater than about 6.5%, or greater than about 7%, or greater than about 7.5%, or greater than about 8%, or greater than about 8.5%, or greater than about 9%, or greater than about 9.5%, or greater than about 10%, or greater than about 10.5%, or greater than about 11%, or greater than about 11.5%, or greater than about 12%, or greater than about 12.5%, or greater than about 13%, or greater than about 13.5% clipped impurity, as measured by reducing SDS-cGE. Percent clipped impurity is defined hereinabove.

The processes of the present invention generate an eluate that is a highly pure composition of intact activatable antibody. The resulting eluate (and corresponding purified composition of intact activatable antibody) often comprises at least about 90%, or at least about 91%, or at least about 92%, or at least about 93%, or at least about 94%, or at least about 95%, or at least about 96%, or at least about 97%, or at least about 98%, or at least about 98.5%, or at least about 99% intact activatable antibody, as measured by reducing SDS-cGE. An illustrative SDS-cGE assay is described in Example 1. Percent intact impurity is calculated as described hereinabove (i.e., (% intact activatable antibody)$_{eluate}$).

In one aspect, the present disclosure includes a process for producing a composition including: (A) greater than 95% intact activatable antibody comprising a MM, a CM, and a AB; and (B) 0.05 to 5% clipped variant thereof, the process including loading an aqueous feedstock comprising water, (A), (B), and a first salt onto a chromatography column, wherein the chromatography column comprises a stationary phase that comprises a support matrix and hydrophobic ligands bound thereto, and eluting the chromatography column with an eluent comprising water and a second salt to obtain the composition. In one aspect, the process includes reducing the amount of clipped variant in the process stream by 75 to 90%. In one aspect, the process includes reducing the amount of HCP in the process stream by 75 to 90%. In one aspect, the process includes reducing the amount of HMWS in the process stream by 75 to 90%. In one aspect, the process includes reducing the amount of clipped variant, HCP, and HMWS in the process stream by 70 to 95%.

Activatable antibody is typically produced biologically by culturing cells engineered to express the desired intact activatable antibody. For example, the cells may be mammalian host cells. In some aspects, the cells may be human embryonic kidney (HEK) cells, e.g., HEK293 cells, or Chinese hamster ovary (CHO) cells. In these processes, activatable antibody is harvested from the cell culture as a cell culture supernatant, cellular lysate, or other like composition derived from the cell culture that contains the activatable antibody. A bioharvest composition is obtained by separating the cells and cellular debris from the supernatant or lysate, using, for example, centrifugation, filtration, or other solid-liquid separation process.

The hydrophobic chromatography process is often deployed downstream of the cell culturing step, with, optionally, one or more intervening unit operations for removing at least a portion of non-immunoglobulin proteins, host cell proteins, and other impurities that may be present in the bioharvest composition, and if applicable, any bulk intermediate product composition.

Each cell culturing step, the optional one or more intervening unit operations, and hydrophobic chromatography process may be conducted as a batch-wise process, or optionally, any two or more of the foregoing unit operations may be conducted as a continuous or semi-continuous process in an optionally integrated system. In some embodiments, the cell culturing step is performed as a fed-batch operation. In some embodiments, the cell culturing step is performed as a continuous feed or perfusion operation.

In some embodiments, the bioharvest composition and/or one or more bulk intermediate product compositions is/are staged over a period of time prior to being fed to the next unit operation. Bulk intermediate product compositions may be optionally conditioned with the addition of one or more conditioning agents to render it suitable as feed for the next, subsequent unit operation. Exemplary conditioning agents include for example, a buffer (i.e., one or more buffering agents), a salt (e.g., the first salt), a base, an acid, and the like.

Thus, aqueous feedstocks employed in the practice of the present invention may comprise a bioharvest composition or a bulk intermediate product composition. In some embodiments, prior to step (a), the process comprises:

(a⁰) subjecting a bioharvest composition comprising the intact activatable antibody activatable antibody and the corresponding clipped impurity to one or more intervening unit operations selected from the group consisting of a centrifugation step, a filtration step, an affinity chromatography step, a virus inactivation step, a size exclusion chromatography step, a virus filtration step, and an ion exchange (IEX) chromatography step to produce one or more bulk intermediate product compositions, wherein the aqueous feedstock comprises at least one bulk intermediate product composition. In some embodiments, the process comprises a combination of at least two or more intervening unit operations.

In some embodiments, the bioharvest composition is subjected to at least two or more, or in certain embodiments, at least three or more serial intervening unit operations selected from the group consisting of a centrifugation step, a filtration step, an affinity chromatography step, a virus inactivation step, a size exclusion chromatography step, a virus filtration step, and an ion exchange chromatography step. In some embodiments, the bioharvest composition is subjected to an affinity chromatography step, and often, additionally a virus inactivation step, and an optional ion exchange chromatography step. For example, affinity chromatography may be employed to separate immunoglobulin (Ig)-containing components from other components in the bioharvest composition by using an immobilized ligand such as, for example, Protein A (i.e., a "Protein A chromatography" step), Protein G (i.e., a "Protein G chromatography" step), and the like. In certain embodiments, the one or more intervening unit operations of step ($a^0$) comprises an affinity chromatography step and an ion exchange chromatography step. In some embodiments, the one or more intervening unit operations of step ($a^0$) comprises an affinity chromatography step, a virus inactivation step, a filtration step (e.g., a tangential flow filtration step, an ultrafiltration step, a diafiltration step, and the like), and an ion exchange chromatography step. In certain embodiments, the ion exchange chromatography step is an anion exchange chromatography step. In some aspects, the method of the present disclosure includes methods that exclude any one or combination of the operations described in this disclosure. For example, a method of the present disclosure may exclude an anion exchange step. As another example, a method of the present disclosure may exclude a cation exchange step. As another example, a method of the present disclosure may exclude a size exclusion chromatography step.

When the process employs one or more intervening unit operations, the bulk intermediate product composition produced by the intervening unit operation immediately upstream of the hydrophobic chromatography process is referred to herein as the "pre-feed". In some embodiments, the pre-feed may be used directly as the aqueous feedstock. In certain embodiments, the pre-feed may be conditioned by adding one or more components, such as, for example, the first salt, one or more buffering agents (such as, for example, a salt, an acid, and/or a base), and the like.

The eluate (and corresponding purified composition of intact activatable antibody), enriched with intact activatable antibody relative to clipped impurity, may be optionally subjected to one or more downstream unit operations to generate a downstream product composition. Illustrative downstream unit operations include, for example, a (further) purification process, a chemical synthesis process, a dilution process, a solvent exchange process, a formulating process, a lyophilization process, or any combination of two or more thereof. For example, in one embodiment, the process further comprises subjecting the eluate to one or more downstream unit operations selected from the group consisting of a centrifugation step, a filtration step (e.g., tangential flow filtration, ultrafiltration, diafiltration, and the like), an affinity chromatography step, a virus inactivation step, a size exclusion chromatography step, a virus filtration step, an ion exchange chromatography step, and any combination of two or more thereof. The eluate and downstream product compositions often have either no detectable quantities, or very low quantities of clipped impurity, and/or HCP, and/or HMWS. The eluate and downstream product compositions may be substantially free of clipped impurity.

In some embodiments, the purified intact activatable antibody composition generated by the processes of the present invention (e.g., the eluate or a downstream product composition) is subjected to a chemical conjugation reaction by contacting the eluate or downstream product composition with a conjugation reagent under conditions sufficient to generate a conjugated activatable antibody. Conjugation moieties function to impart an additional property to the activatable antibody, such as, for example, extended half-life (e.g., where the conjugation moiety is a half-life extender, such as, for example, a polyethylene glycol (PEG) moiety, a human serum albumin (HSA moiety), and the like); cytotoxicity (where the conjugation moiety is all or part of a toxin, such as, for example, a dolastin or derivative thereof (e.g., auristatin E, AFP, MMAF, MMAE, MMAD, DMAF, DMAE, and the like, and derivatives thereof), a maytansinoid or derivative thereof, DM1, DM4, a duomycin or derivative thereof, a calicheamicin or derivative thereof, a pyrrolobenzodiazepine or derivative or dimer thereof, a heavy metal (e.g., barium, gold, platinum, and the like), a *Pseudomonas* toxin A variant (e.g., PE38, ZZ-PE38, and the like), ZJ-101, OSW-1, a 4-nitrobenzyloxycarbonyl derivative of O6-benzylguanine, a toposiomerase inhibitor, hemiasterlin, cephalotaxine, homoharringonine, a pyrrolobenzodiazepine dimer, a pyrrolobenzodiazepene, a functionalized pyrrolobenzodiazepene, a functionalized pyrrolbenzodiazepene dimer, a calicheamicin, a podophyllotoxin, a taxane, a vinca alkaloid, and the like, as well as any of a variety of other known cytotoxic agents); anti-viral activity (e.g., where the conjugation moiety is all or a portion of Acyclovir, Vira A, Symetrel, Turbostatin, a Phenstatin, Hydroxyphenstatin, Spongistatin 5, Spongistatin 7, Halistatin 1, Halistatin 2, Halistatin 3, a modified bryostatin, a halocomstatin, pyrrolobenzimadazole, cibrostatin6, doxaliform, an anthracycline analogue, a cemadotin analogue (e.g., CemCH2-SH), and the like); antifungal activity (e.g., wherein the conjugation moiety is all or a portion of Nystatin, and the like); anti-neoplastic activity (e.g., wherein the conjugation moiety is all or a portion of Adriamycin, cerubidine, bleomycin, alkeran, velban, oncovin, fluorouracil, methotrexate, thiotepa, bisantrene, novantrone, thioguanine, procarabizine, cytarabine, and the like); anti-bacterial activity (e.g., wherein the conjugation moiety is all or a portion of an aminoglycoside, streptomycin, neomycin, kanamycin, amikacin, gentamicin, tobramycin, Streptomycin B, spectinomycin, ampicillin, sulfanilamide, polymyxin, chloramphenicol, and the like); anti-mycoplasmal activity (e.g., where the conjugation moiety is all or a portion of tylosine, spectinomycin, and the like); as well as any of a variety of other desirable additional properties.

Conjugation moieties that impart such desired properties and functions can be readily conjugated to the activatable antibody using methods and reactive linkers that are known in the art. In some embodiments, compositions of conjugated activatable antibody prepared from purified activatable antibody compositions as described herein, are also substantially free of clipped impurity and/or HCP and/or HMWS. With respect to clipped impurity, HCP, and HMWS, these conjugated activatable antibody compositions often have the same purity and impurity profiles as the eluate and purified intact activatable antibody compositions described herein.

In a further embodiment, the present invention provides purified intact activatable antibody compositions that can be produced by the processes of the present invention. In some embodiments, the purified intact activatable antibody composition comprises at least about 90% intact activatable antibody, as measured by reducing SDS-cGE, wherein % intact activatable antibody is defined hereinabove; less than about 15% clipped impurity, as measured by reducing SDS-cGE, wherein % clipped impurity is defined hereinabove; less than about 5% HMWS, as measured by SE-HPLC, wherein % HMWS is defined hereinabove; and less than about 150 ppm HCP, as measured by a corresponding HCP ELISA assay. In certain of these embodiments, the purified intact activatable antibody composition comprise at least about 91%, or at least about 92%, or at least about 93%, or at least about 94%, or at least about 95%, or at least about 96%, or at least about 97%, or at least about 98%, or at least about 99% intact activatable antibody.

In some of these purified intact activatable antibody compositions, the composition comprises less than about 14%, or less than about 13%, or less than about 12%, or less than about 11%, or less than about 10%, or less than about 9%, or less than about 8%, or less than about 7%, or less than about 6% clipped impurity, as measured by SDS-cGE. In certain embodiments, the purified intact activatable antibody composition comprises less than about 5%, or less than about 4%, or less than about 3%, or less than about 2%, or less than about 1%, or less than about 0.9%, or less than about 0.8%, or less than about 0.7%, or less than about 0.6%, or less than about 0.5% clipped impurity, as measured by a reducing SDS-cGE assay. In other embodiments, the purified intact activatable antibody composition comprises less than about 2%, or less than about 1%, or less than about 0.8%, or less than about 0.8%, or less than about 0.7%, or less than about 0.6%, or less than about 0.5% clipped impurity, as measured by SDS-cGE. An illustrative SDS-cGE assay is described in Example 1. In certain embodiments, the purified intact activatable antibody composition comprises no detectable clipped impurity, as measured by reducing SDS-cGE.

In certain embodiments, the purified intact activatable antibody composition comprises a relative quantity of clipped impurity in the range of from about 0.1% to about 15% clipped impurity, or from about 0.1% to about 10% clipped impurity, or from about 0.1% to about 10% clipped impurity, or from about 0.1% to about 5% clipped impurity, or from about 0.1% to about 4% clipped impurity, or from about 0.1% to about 3% clipped impurity, or from about 0.1% to about 2% clipped impurity, or from about 0.1% to about 1% clipped impurity, as determined by reducing SDS-cGE. In certain embodiments, the purified intact activatable antibody composition comprises no detectable clipped impurity, as determined by reducing SDS-cGE.

In some embodiments, the purified intact activatable antibody composition comprises less than about 140 ppm HCP, or less than about 130 ppm HCP, or less than about 120 ppm HCP, or less than about 110 ppm HCP, or less than about 100 ppm HCP, or less than about 90 ppm HCP, or less than about 80 ppm HCP, or less than about 70 ppm HCP, or less than about 60 ppm HCP, or less than about 50 ppm HCP, or less than about 45 ppm HCP, or less than about 40 ppm HCP, or less than about 35 ppm HCP, or less than about 30 ppm HCP, or less than about 25 ppm HCP, or less than about 20 ppm HCP, or less than about 15 ppm HCP, or less than about 10 ppm HCP, as measured by a corresponding HCP ELISA. In some of these embodiments, the purified activatable antibody composition comprises less than about 50 ppm, or less than about 45 ppm, or less than about 40 ppm, or less than about 35 ppm, or less than about 30 ppm, or less than about 25 ppm, or less than about 20 ppm, or less than about 15 ppm, or less than about 10 ppm HCP, as measured by a corresponding HCP ELISA assay. In certain embodiments, the purified intact activatable antibody composition comprises no detectable HCP, as measured by a corresponding host cell ELISA.

In other embodiments, the purified intact activatable antibody composition comprises a quantity of HCP in the range of from about 0.5 ppm HCP to about 150 ppm HCP, or from about 0.5 ppm HCP to about 140 ppm HCP, or 0.5 ppm HCP to about 130 ppm HCP, or from about 0.5 ppm HCP to about 120 ppm, or from about 0.5 ppm HCP to about 110 ppm, or from about 0.5 ppm HCP to about 100 ppm HCP, or from about 0.5 ppm HCP to about 90 ppm HCP, or from about 0.5 ppm HCP to about 90 ppm HCP, or from about 0.5 ppm HCP to about 80 ppm HCP, or from about 0.5 ppm HCP to about 70 ppm HCP, or from about 0.5 ppm HCP to about 60 ppm HCP, or from about 0.5 ppm HCP to about 50 ppm HCP, or from about 0.5 ppm HCP to about 45 ppm HCP, or from about 0.5 ppm HCP to about 40 ppm HCP, or from about 0.5 ppm HCP to about 40 ppm HCP, or from about 0.5 ppm HCP to about 35 ppm HCP, or from about 0.5 ppm HCP to about 30 ppm HCP, or from about 1 ppm HCP to about 25 ppm HCP, or from about 1 ppm HCP to about 20 ppm HCP, or from about 0.5 ppm HCP to about 15 ppm HCP, or from about 0.5 ppm HCP to about 10 ppm HCP.

In certain embodiments, the purified intact activatable antibody composition comprises a quantity of HCP in the range of from about 1 ppm HCP to about 150 ppm HCP, or from about 1 ppm HCP to about 140 ppm HCP, or 1 ppm HCP to about 130 ppm HCP, or from about 1 ppm HCP to about 120 ppm, or from about 1 ppm HCP to about 110 ppm, or from about 1 ppm HCP to about 100 ppm HCP, or from about 1 ppm HCP to about 90 ppm HCP, or from about 1 ppm HCP to about 90 ppm HCP, or from about 1 ppm HCP to about 80 ppm HCP, or from about 1 ppm HCP to about 70 ppm HCP, or from about 1 ppm HCP to about 60 ppm HCP, or from about 1 ppm to about 50 ppm HCP, or from about 1 ppm HCP to about 45 ppm HCP, or from about 1 ppm HCP to about 40 ppm HCP, or from about 1 ppm HCP to about 40 ppm HCP, or from about 1 ppm HCP to about 35 ppm HCP, or from about 1 ppm HCP to about 30 ppm HCP, or from about 1 ppm HCP to about 25 ppm HCP, or from about 1 ppm HCP to about 20 ppm HCP, or from about 1 ppm HCP to about 15 ppm HCP, or from about 1 ppm HCP to about 10 ppm HCP.

In some embodiments, the purified intact activatable antibody composition comprises less than about 4%, or less than about 3%, or less than about 2%, or less than about 1% HMWS, as determined by SE-HPLC, where % HMWS is defined hereinabove.

In certain embodiments, the purified intact activatable antibody composition comprises a quantity of HMWS in the range of from about 0.2% HMWS to about 5% HMWS, or from about 0.2% HMWS to about 4% HMWS, or from about 0.2% HMWS to about 3% HMWS, or from about 0.2% HMWS to about 2% HMWS, or from about 0.2% HMWS to about 1% HMWS, as determined by SE-HPLC. In some embodiments, the purified intact activatable antibody composition comprises no detectable HMWS.

In some aspects, the purified intact activatable antibody composition includes greater than 90% intact activatable antibody and 0.05 to 5% clipped variant, as measured by SDS-cGE. In some aspects, the composition includes greater than 90% intact activatable antibody and 0.05 to 5% clipped variant (as determined by SDS-cGE), less than 150 ppm host cell proteins (HCP) (as determined by host cell ELISA), and less than 5% high molecular weight species (HMWS) (as determined by SE-HPLC). In some aspects, the composition includes greater than 96% intact activatable antibody, 0.05 to 4% clipped variant, less than 150 ppm host cell proteins (HCP) and less than 5% HMWS. In some aspects, the composition includes greater than 97% intact activatable antibody, 0.05 to 3% clipped variant, less than 150 ppm host cell proteins (HCP) and less than 5% HMWS. In some aspects, the composition includes greater than 98% intact activatable antibody, 0.05 to 2% clipped variant, less than 150 ppm host cell proteins (HCP) and less than 5% HMWS. In some aspects, the composition includes greater than 95% intact activatable antibody, 0.05 to 5% clipped variant, less than 100 ppm host cell proteins (HCP) and less than 3% HMWS. In some aspects, the composition includes greater than 95% intact activatable antibody, 0.05 to 3% clipped variant, less than 100 ppm host cell proteins (HCP) and less than 3% HMWS. In some aspects, the composition includes greater than 95% intact activatable antibody, 0.05 to 2% clipped variant, less than 100 ppm host cell proteins (HCP) and less than 3% HMWS. In some aspects, the composition includes greater than 95% intact activatable antibody, 0.05 to 5% clipped variant, less than 100 ppm host cell proteins (HCP) and less than 2% HMWS. In some aspects, the composition includes greater than 95% intact activatable antibody, 0.05 to 5% clipped variant, less than 100 ppm host cell proteins (HCP) and less than 1.5% HMWS. In some aspects, the composition includes greater than 95% intact activatable antibody, 0.05 to 3% clipped variant, less than 100 ppm host cell proteins (HCP) and less than 1.5% HMWS. In some aspects, the composition includes greater than 95% intact activatable antibody, 0.05 to 2% clipped variant, less than 100 ppm host cell proteins (HCP) and less than 1.5% HMWS. In some aspects, the composition includes greater than 95% intact activatable antibody, 0.05 to 5% clipped variant, less than 25 ppm host cell proteins (HCP) and less than 1.5% HMWS. In some aspects, the composition includes greater than 95% intact activatable antibody, 0.05 to 3% clipped variant, less than 25 ppm host cell proteins (HCP) and less than 1.5% HMWS. In some aspects, the composition includes greater than 95% intact activatable antibody, 0.05 to 2% clipped variant, less than 25 ppm host cell proteins (HCP) and less than 1.5% HMWS. In some aspects, the composition includes greater than 95% intact activatable antibody, 0.05 to 2% clipped variant, less than 10 ppm host cell proteins (HCP) and less than 1.5% HMWS. In some aspects, the composition includes greater than 95% intact activatable antibody, 0.05 to 5% clipped variant, less than 25 ppm host cell proteins (HCP) and less than 1.0% HMWS. In some aspects, the composition includes greater than 95% intact activatable antibody, 0.05 to 3% clipped variant, less than 25 ppm host cell proteins (HCP) and less than 1.0% HMWS. In some aspects, the composition includes greater than 95% intact activatable antibody, 0.05 to 2% clipped variant, less than 25 ppm host cell proteins (HCP) and less than 1.0% HMWS. In some aspects, the composition includes greater than 95% intact activatable antibody, 0.05 to 2% clipped variant, less than 10 ppm host cell proteins (HCP) and less than 1.0% HMWS. In some aspects, the clipped variant is a single-arm clipped species.

The present invention also provides a pharmaceutical composition comprising the purified composition of intact activatable antibody of the present invention and one or more pharmaceutically acceptable components. In some embodiments, the pharmaceutically acceptable component is a pharmaceutically acceptable excipient. Such compositions may be prepared by adding the pharmaceutically acceptable excipient to a purified composition produced by the process of the present invention, such as, for example, the purified composition of intact activatable antibody of the present invention, or further composition derived therefrom. Pharmaceutically acceptable excipients that are suitable for use in compositions of the present invention are well known in the art, and include, for example, sterile water, a surfactant (e.g., a nonionic surfactant, a cationic surfactant, and/or an anionic surfactant), a buffering agent (an acid, a base, and/or a salt), an alcohol, a diol, a polyol, a sugar (e.g., a monosaccharide, a disaccharide, and/or a polysaccharide), a hydrophilic polymer (e.g., a polyethylene glycol (PEG), a polyvinyl alcohol, a solubilizing agent (e.g., a cyclodextrin, and the like), and the like. The composition may be in either liquid form or it may be a solid form, e.g., particulate form. For example, the solid form may be prepared by lyophilizing a corresponding liquid composition to form a lyophilized pharmaceutical composition.

When the pharmaceutical composition is in liquid form, it typically further comprises water (e.g., sterile water). In some embodiments, the composition further comprises water and one or more components selected from the group consisting of a surfactant, a buffering agent, a sugar, and any combination of two or more thereof. When the pharmaceutical composition is in solid (e.g., lyophilized) form, it typically comprises one or more components selected from the group consisting of a sugar and a buffering agent. In some embodiments, the composition comprises a sugar.

The processes and compositions of the present invention may employ any of a wide variety of activatable antibodies. As illustrated in the examples hereinbelow, the process is shown to be capable of producing purified compositions of intact activatable antibody with significant reduction in clipped impurity, as well as HCP and HMWS. In each instance where aqueous feedstock comprising these activatable antibodies was purified using the processes of the present invention, an eluate that was enriched in intact activatable antibody and substantially depleted of impurities that included clipped impurity, HMWS, eluted first. This observation was consistent across a variety of activatable antibody amino acid sequences. Thus, it is believed that the processes of the present invention are applicable to any of a variety of crude activatable antibody compositions regardless of the specific amino acid sequences (e.g., MM, CM, AB) of the activatable antibody. Accordingly, compositions that may be purified using the processes of the present invention may comprise an activatable antibody having an AB component capable of specifically binding to any one of a number of biological targets known in the art (when not masked) by, for example, incorporating VL and VH CDR amino acid sequences from antibodies known to bind to the desired biological target, or alternatively, or identified by using any of a variety of known antibody discovery screening platforms known in the art.

Illustrative classes of biological targets include cell surface receptors and secreted binding proteins (e.g., growth factors, and the like), soluble enzymes, structural proteins (e.g., collagen, fibronectin, and the like), and the like. Suitable biological targets include, for example, 1-02-LFA-3, α4-integrin, α-V-integrin, α4β1-integrin, AGR2, Anti- Lewis-Y, Apelin J receptor, APRIL, B7-H4, BAFF, BTLA, C5 complement, C-242, CA9, CA19-9 (Lewis a), carbonic anhydrase 9, CD2, CD3, CD6, CD9, CD11a, CD19, CD20, CD22, CD25, CD28, CD30, CD33, CD40, CD40L, CD41, CD44, CD44v6, CD47, CD51, CD52, CD56, CD64, CD70, CD71, CD74, CD80, CD81, CD86, CD95, CD117, CD125, CD132 (IL-2RG), CD133, CD137, CD137, CD138, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL4, DPP-4, DSG1, EGFR, EGFRviii, Endothelin B receptor (ETBR), ENPP3, EpCAM, EPHA2, ERBB3, F protein of RSV, FAP, FGF-2, FGF-8, FGFR1, FGFR2, FGFR3, FGFR4, Folate receptor, GAL3ST1, G-CSF, G-CSFR, GD2, GITR, GLUT1, GLUT4, GM-CSF, GM-CSFR, GP IIb/IIIa receptors, GP130, GPIIB/IIIA, GPNMB, GRP78, Her2/neu, HVEM, Hyaluronidase, ICOS, IFNα, IFNβHGF, hGH, hyaluronidase, ICOS, IFNα, IFNβ, IFNγ, IgE, IgE receptor (FceRI), IGF, IGF1R, IL1B, IL1R, IL2, IL11, IL12p40, IL-12R, IL-12Rβ1, IL13, IL13R, IL15, IL17, IL18, IL21, IL23, IL23R, IL27/IL27R (wsx1), IL29, IL-31R, IL31/IL31R, IL-2R, IL4, IL4-R, IL6, IL-6R, Insulin Receptor, Jagged Ligands, Jagged 1, Jagged 2, LAG-3, LIF-R, Lewis X, LIGHT, LRP4, LRRC26, MCSP, Mesothelin, MRP4, MUC1, Mucin-16 (MUC16, CA-125), Na/K ATPase, Neutrophil elastase, NGF, Nicastrin, Notch Receptors, Notch 1, Notch 2, Notch 3, Notch 4, NOV, OSM-R, OX-40, PAR2, PDGF-AA, PDGF-BB, PDGFRα, PDGFRβ, PD-1, PD-L1, PD-L2, Phosphatidylserine, P1GF, PSCA, PSMA, RAAG12, RAGE, SLC44A4, Sphingosine 1 Phosphate, STEAP1, STEAP2, TAG-72, TAPA1, TGFβ, TIGIT, TIM-3, TLR2, TLR6, TLR7, TLR8, TLR9, TMEM31, TNFα, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, WISP-3, and the like.

The AB is formed from (and thus the activatable antibody comprises) a VL and a VH, which are linked together either directly or indirectly, for example, via a covalent or non-covalent bond. In some embodiments, the VL and VH are linked together by one or more disulfide bonds (e.g., via one or more Cys-Cys disulfide bridges), by a peptide linker, by a synthetic linker, by a naturally occurring linker, and the like. Structurally, each AB may be independently in any of a wide variety of formats, such as, for example, a Fab, a F(ab')$_2$, a monospecific Fab$_2$, a bispecific Fab$_2$, a trispecific Fab$_3$, an scFv, a bispecific diabody, a trispecific triabody, an scFv-Fc, a minibody, a bispecific T cell engager (e.g., a BiTE™), a dual-affinity re-targeting antibody (DART antibody), and the like. Suitable bispecific formats include any one of a number of bispecific antibody formats known in the art, including those described in Kontermann, et al., "Bispecific Antibodies", *Drug Discovery Today* (2015) 20(7): 838-847, which is incorporated herein by reference in its entirety.

In some embodiments, the activatable antibodies comprise a first VL having a set of first VL CDRs (i.e., a first VL CDR1, a first VL CDR2, and a first VL CDR3) and a first VH having a set of first VH CDRs (i.e., a first VH CDR1, a first VH CDR2, and a first VH CDR3), where the VL and VH together form the corresponding AB. In some embodiments, the activatable antibody also has a second AB that has a specific binding affinity for a second biological target, where the second AB comprises a second VL, a second VH, and a second prodomain that comprises a second MM and a second CM, wherein the second AB is coupled to the second prodomain. In these embodiments, the second VL comprises a set of second VL CDRs (i.e., a second VL CDR1, a second VL CDR2, and a second VL CDR3) and a second VH having a set of second VH CDRs (i.e., a second VH CDR1, a second VH CDR2, and a second VH CDR3), where the VL and VH together form the corresponding second AB. Purified compositions of activatable antibodies having additional ABs (from third VL and third VH amino acid sequences, and so on) may be prepared using the process of the present invention, where each additional AB has a corresponding MM and CM coupled to it. Each set of VL and VH corresponding to an AB may be encoded by a single polypeptide (such as, for example, an scFv, and the like), or two polypeptides (such as an antibody light chain and an antibody heavy chain). VH and VL CDR sequences having binding specificity for a wide variety of biological targets are known in the art and may be incorporated into the activatable antibodies employed in the processes and compositions of the present invention.

In some embodiments when the activatable antibody comprises a second VL and a second VH, the amino acid sequence of each CDR in the set of first VL CDRs is identical to the amino acid sequence of the corresponding CDR in the set of second VL CDRs. In certain embodiments, the amino acid sequence of each CDR in the set of first VH CDRs is identical to the amino acid sequence of the corresponding CDR in the set of second VH CDRs. In these embodiments, the first AB and the second AB (i.e., when not masked) typically have binding specificity for the same biological target species.

In some embodiments, the amino acid sequence of at least one CDR in the set of first VL CDRs is not identical to the amino acid sequence of the corresponding CDR in the set of second VL CDRs and/or the amino acid sequence of at least one CDR in the set of first VH CDRs is not identical to the amino acid sequence of the corresponding CDR in the set of second VH CDRs. In these embodiments, the first biological target and the second biological target may be the same or different. For example, the first AB and the second AB may bind to different epitopes or bind to overlapping epitopes on the same biological target. In some of these embodiments, the first biological target and the second biological target are not the same (i.e., the activatable antibody is a "multispecific" activatable antibody, such as a bispecific activatable antibody, and the like). Often, in these embodiments, at least one of the first and second biological targets is a cell surface receptor or ligand associated, for example, with cancer, cell proliferation, or an inflammatory process. In some of the bispecific embodiments, the first biological target is a cluster of differentiation 3 (CD3) T cell co-receptor. Usually, at least one of the other of the first and second biological targets is an extracellular membrane-bound protein in which expression from the cell or presence of the cell is associated with a diseased state.

In some embodiments, the VL and VH domains of the activatable antibody reside within an antibody light and an antibody heavy chain, respectively, each having incorporated with them, at least one additional component. For example, the light chain may comprise an amino acid sequence that encodes a VL and at least one additional component selected from the group consisting of a prodomain, a linker, a light constant domain (λ or κ), and a combination of any two or more thereof and the heavy chain may comprise an amino acid sequence that encodes a VH, and at least one additional component selected from the group consisting of a prodomain, a linker, one or more heavy constant domains (i.e., a CH1, a CH2, and/or a CH3 domain) and/or a hinge region, and a combination of any two or more thereof, provided that at least one of the light chain and heavy chain comprises an amino acid sequence that encodes a prodomain. In some embodiments, the heavy chain comprises an amino acid sequence that encodes an Fc region that corresponds substantially to a human immunoglobulin (Ig) class selected from the group consisting of an IgA, an IgD, an IgG, an IgE, and an IgM.

Often, the Fc domain comprises a native human Fc domain. In some embodiments, the Fc domain is an engineered human Fc domain that has an amino acid sequence that differs from a native human Fc domain. Engineered Fc domains often exhibit altered effector function relative to the corresponding native Fc domain. Such functions include, for example, enhanced antibody-dependent cell-mediated cytotoxicity (ADCC), enhanced antibody-dependent cellular phagocytosis (ADCP), enhanced complement-dependent cytotoxicity (CDC), reduced effector function, increased half-life, increased FcγRIIb binding, increased FcγRIIa binding, and the like.

Additional examples of engineered human Fc domains are known to those skilled in the art. Examples of Ig heavy chain constant region amino acids in which mutations in at least one amino acid leads to reduced Fc function include, but are not limited to, mutations in amino acid 228, 233, 234, 235, 236, 237, 239, 252, 254, 256, 265, 270, 297, 318, 320, 322, 327, 329, 330, and 331 of the heavy constant region. Examples of combinations of mutated amino acids are also known in the art, such as, but not limited to a combination of mutations in amino acids 234, 235, and 331, such as L234F, L235E, and P331S or a combination of amino acids 318, 320, and 322, such as E318A, K320A, and K322A.

Further examples of engineered Fc domains include, F243L/R292P/Y300L/V305I/P396 IgG1; S239D/I332E IgG1; S239D/I332E/A330L IgG1; S298A/E333A/K334A; in one heavy chain, L234Y/L235Q/G236W/S239M/H268D/D270E/S298A IgG1, and in the opposing heavy chain, D270E/K326D, A330M/K334E IgG; G236A/S239D/I332E IgG1; K326W/E333S IgG1; S267E/H268F/S324T IgG1; E345R/E430G/S440Y IgG1; N297A or N297Q or N297G IgG1; L235E IgG1; L234A/L235A IgG1; F234A/L235A IgG4; H268Q/V309L/A330S/P331S IgG2; V234A/G237A/P238S/H268A/V309L/A330S/P331S IgG2; M252Y/S254T/T256E IgG1; M428L/N434S IgG1; S267E/L328F IgG1; N325S/L328F IgG1, and the like. In some embodiments, the engineered Fc domain comprises one or more substitutions selected from the group consisting of N297A IgG1, N297Q IgG1, and S228P IgG4. Amino acid residue numbering is based on the EU numbering system.

Activatable antibodies employed in the practice of the present invention may exist in a variety of structural configurations. Illustrative structural formulae for activatable antibodies are provided below. It should be noted that although MM and CM are indicated as distinct components in the formulae below, in all exemplary embodiments (including formulae) disclosed herein it is contemplated that the amino acid sequences of the MM and the CM could overlap, e.g., such that the CM is completely or partially contained within the MM.

Within an activatable antibody, the CM may be positioned between the MM and AB, either directly or indirectly via one or more linkers. Often, each of the MM, CM, and AB components of the activatable antibody are arranged in a structure selected from the group consisting of, from N-terminal to C-terminal:

(MM)-(CM)-(AB); or (AB)-(CM)-(MM)

where MM, CM, and AB are as previously defined, and where each "-" refers independently to a direct or indirect (i.e., via a linker as described hereinbelow) linkage.

In many embodiments, the activatable antibody may comprise one or more linkers to impart flexibility at one or more of the MM-CM junction, the CM-AB junction, or both. For example, in certain embodiments, the activatable antibody may comprise MM, CM, and AB components arranged in a structure selected from the group consisting of, from either N- to C-terminal or C-terminal to N-terminal:

(MM)-L1-(CM)-(AB);

(MM)-(CM)-L2-(AB); or (MM)-L1-(CM)-L2-(AB)

wherein MM, CM, and AB are as defined hereinabove; wherein each linker, L1 and L2, may be the same or different, and each independently may be optionally present or absent.

In some embodiments, the intact activatable antibody comprises a first AB, wherein the first VL is encoded by a first light chain and wherein the first VH is encoded by a first heavy chain, and wherein the first light chain further encodes one or more components selected from the group consisting of a prodomain, a linker, a light constant domain, and a combination of any two or more thereof, and wherein the first heavy chain further encodes one or more components selected from the group consisting of a prodomain, a linker, one or more heavy constant domains, a hinge region, and a combination of any two or more thereof, provided that only one of the light chain and the heavy chain encodes the prodomain. In certain embodiments, the intact activatable antibody further comprises an Fc domain, as described in more detail hereinabove. In some of these embodiments, the activatable antibody comprises a first AB (comprising a first VL and a first VH) and a second AB (comprising a second VL and a second VH). In a specific embodiment, the first VL and the second VH are linked together by a linker, and the second VL and the first VH are linked together by a linker. In a further specific embodiment, the activatable antibody comprises a first single chain antibody comprising the first VL a first linker, and the first VH, and a second single chain antibody comprising the second VL, a second linker, and the second VH, wherein the first single chain antibody and the second single chain antibody are linked together by a third linker.

Activatable antibodies employed in the compositions and processes of the present invention may comprise any of a wide variety of CMs having an amino acid sequence that functions as a substrate for a protease. Suitable substrate amino acid sequences may be identified using any of a variety of known techniques including those described in U.S. Pat. Nos. 7,666,817, 8,563,269, PCT Publication No. WO 2014/026136, and Boulware et al. "Evolutionary optimization of peptide substrates for proteases that exhibit rapid hydrolysis kinetics," *Biotechnol Bioeng*. 106.3 (2010): 339-46, each of which is incorporated by reference in their entireties.

In some embodiments, the CM comprises a substrate for a protease that is active, e.g., up-regulated or otherwise unregulated, in a disease condition or diseased tissue, such that the protease cleaves the CM in the activatable antibody when the activatable antibody is exposed to the protease.

Figure 3A:
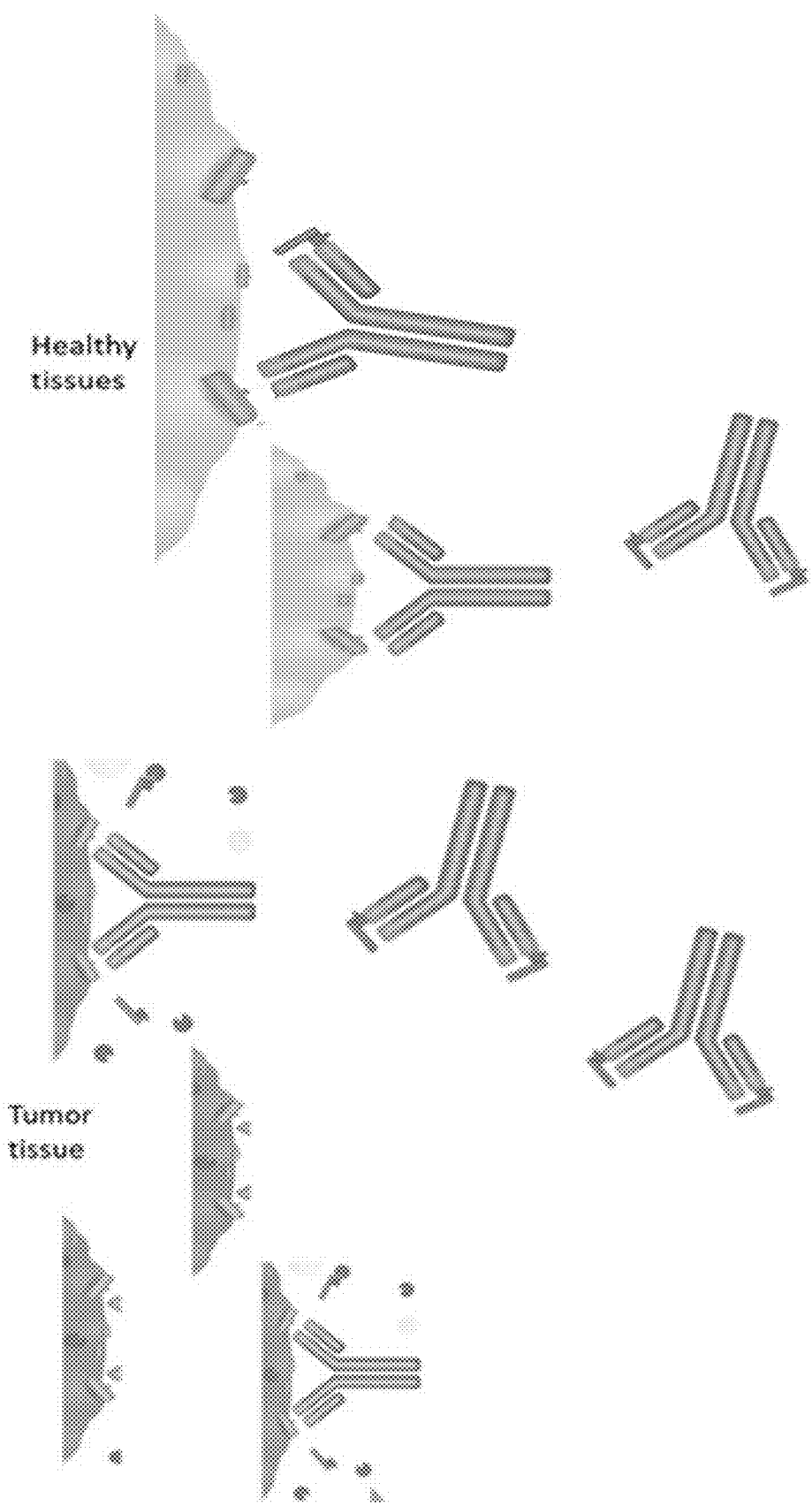
FIG. 3A schematically depicts: (1) administration of the mixture of FIG. 2B to cells in a subject; (2) binding of intact activatable antibody and clipped variants thereof to the subject's cells after administration; (3) binding of clipped variants from the composition to healthy tissues; and (4) activation of intact activatable antibody in the environment of diseased (e.g., tumor) tissues and binding of the activated antibodies thereto.
Figure 3B:
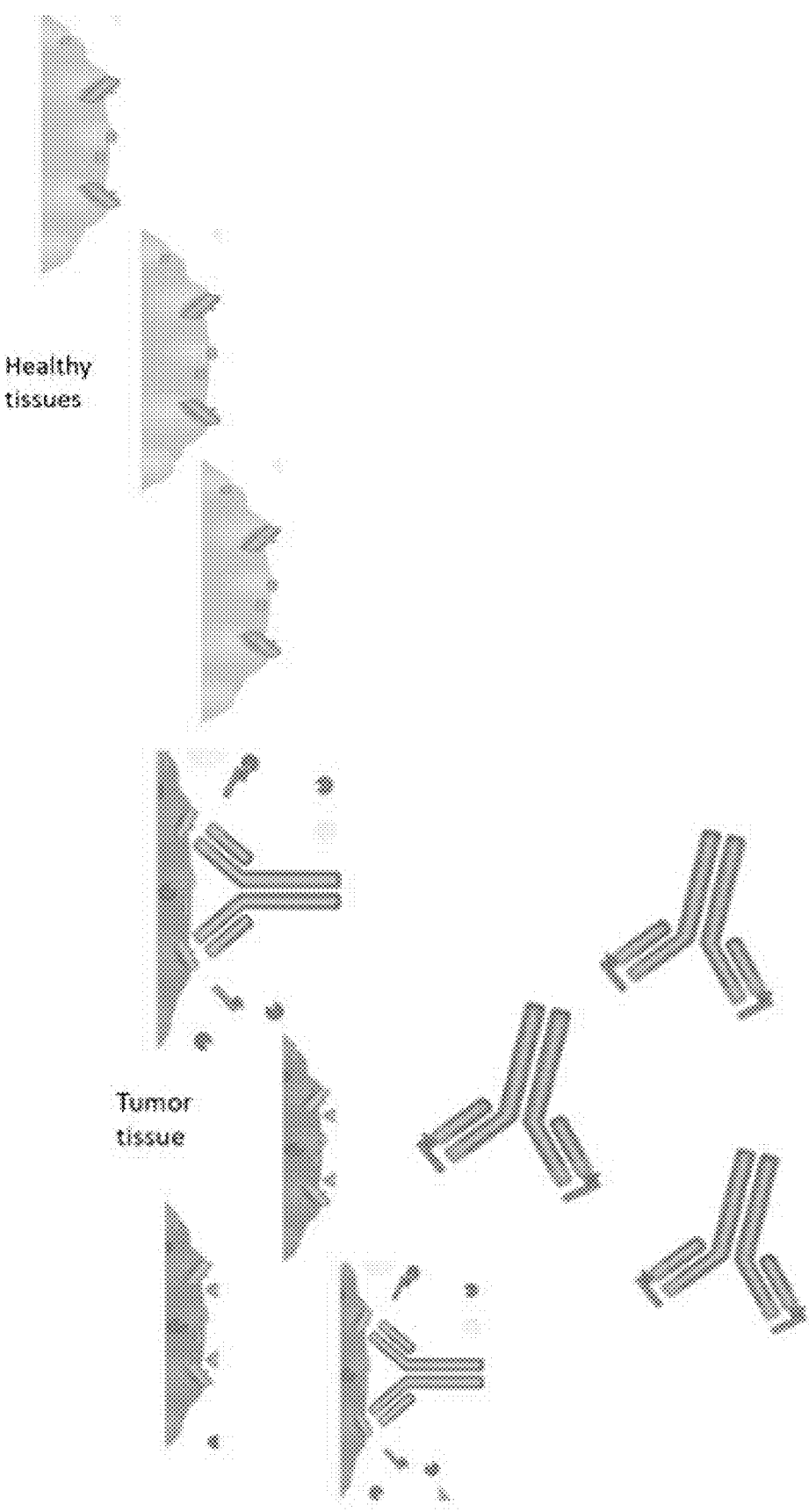
FIG. 3B schematically depicts: (1) binding of intact activatable antibody present in a composition after treatment with a method of the present disclosure upon administration to a subject; (2) lack of binding to healthy tissues of the administered intact activatable antibodies; and (3) activation of intact activatable antibody in the environment of only diseased (e.g., tumor) tissues and binding of the activated antibodies thereto.

Exemplary disease conditions include, for example, a cancer (e.g., where the diseased tissue is a tumor tissue) and an inflammatory or autoimmune condition (e.g., where the diseased tissue is inflamed tissue). In some embodiments, the CM comprises a substrate for an extracellular protease. As illustrated in FIGS. 3A and 3B, the CM of the intact activatable antibody of the present disclosure may be cleaved in the microenvironment of diseased tissues where proteases that cleave the CM are overexpressed relative to healthy tissue. Accordingly, the purified activatable antibody compositions of the present disclosure enable delivery of a target therapeutic dose of the intact activatable antibody to the relevant diseased tissue while minimizing the possibility of delivering a subtherapeutic dose to the diseased tissues and, additionally, avoids delivering clipped and thus, active antibody, to healthy tissues of the subject.

Suitable substrates may be readily identified using any of a variety of known techniques, including those described in U.S. Pat. Nos. 7,666,817, 8,563,269, PCT Publication No. WO 2014/026136, Boulware, et al., "Evolutionary optimization of peptide substrates for proteases that exhibit rapid hydrolysis kinetics," Biotechnolo. Bioeng. (2010) 106.3: 339-46, each of which is hereby incorporated by reference in its entirety. Exemplary substrates include those that are substrates for any one or more of the following proteases: an ADAM, an ADAM-like, or ADAMTS (such as, for example, ADAMS, ADAMS, ADAM10, ADAM12, ADAM15, ADAM17/TACE, ADAMDEC1, ADAMTS1, ADAMTS4, ADAMTS5); an aspartate protease (such as, for example, BACE, Renin, and the like); an aspartic cathepsin (such as, for example, Cathepsin D, Cathepsin E, and the like); a caspase (such as, for example, Caspase 1, Caspase 2, Caspase 3, Caspase 4, Caspase 5, Caspase 6, Caspase 7, Caspase 7, Caspase 8, Caspase 9, Caspase 10, Caspase 14, and the like); a cysteine proteinase (such as, for example, Cruzipain, Legumain, Otubain-2, and the like); a kallikrein-related peptidase (KLK) (such as, for example, KLK4, KLK5, KLK6, KLK7, KLK8, KLK10, KLK11, KLK13, KLK14, and the like); a metallo proteinase (such as, for example, Meprin, Neprilysin, prostate-specific membrane antigen (PSMA), bone morphogenetic protein 1 (BMP-1), and the like); a matrix metalloproteinase (MMP) (such as, for example, MMP1, MMP2, MMP3, MMP7, MMP8, MMP9, MMP10, MMP11, MMP12, MMP13, MMP14, MMP15, MMP16, MMP17, MMP19, MMP20, MMP23, MMP24, MMP26, MMP27, and the like); a serine protease (such as, for example, activated protein C, Cathepsin A, Cathepsin G, Chymase, a coagulation factor protease (such as, for example, FVIIa, FIXa, FXa, FXIa, FXIIa, and the like)); elastase, Granzyme B, Guanidinobenzoatase, HtrA1, Human Neutrophil Elastase, Lactoferrin, Marapsin, NS3/4A, PACE4, Plasmin, prostate-specific antigen (PSA), tissue plasminogen activator (tPA), Thrombin, Tryptase, urokinase (uPA), a Type II transmembrane Serine Protease (TTSP) (such as, for example, DESC1, DPP-4, FAP, Hepsin, Matriptase-2, MT-SP1/Matriptase, TMPRSS2, TMPRSS3, TMPRSS4, and the like), and the like. Specific activatable antibody CMs are described, for example, in WO 2010/081173, WO 2015/048329, WO 2015/116933, and WO 2016/118629, each of which is incorporated herein by reference in its entirety.

In some embodiments, at least one or more of the CMs present in the intact activatable antibody (e.g., one or both of a first and second CM (if present)) comprises a substrate for at least one MMP. In certain of these embodiments, the MMP is selected from the group consisting of MMP9, MMP14, MMP1, MMP3, MMP13, MMP17, MMP11, and MMP19. In a specific embodiment, at least one or more of the CMs present in the intact activatable antibody (e.g., one or both of a first and second CM (if present)) comprises a substrate for MMP14. In certain embodiments, the CM is a substrate for at least one protease selected from the group consisting of a matrix metalloprotease (MMP), thrombin, a neutrophil elastase, a cysteine protease, legumain, and a serine protease, such as matriptase (MT-SP1), and urokinase (uPA). Without being bound by theory, it is believed that these proteases are up-regulated or otherwise unregulated in at least one of cancer, inflammation, or autoimmunity.

In some embodiments, one or more CMs present in the intact activatable antibody (e.g., one or both of a first and second CM (if present)) comprises an amino acid sequence comprising substrates for at least two different proteases (i.e., at least a first protease and at least a second protease). In these embodiments, the cleavage site may be the same or different for the at least two different proteases. Suitable first and second proteases include any of those described hereinabove. In certain of these embodiments, the first protease is selected from the group consisting of an MMP, a thrombin, a neutrophil elastase, a cysteine protease, a uPA, a legumain and a matriptase and the second protease is selected from the group consisting of any of those described hereinabove. In some embodiments, the first protease is a matrix metalloprotease (MMP) and the second protease is a serine protease (SP).

The CM may be designed to comprise two or more known substrates for the at least two or more different proteases, wherein the two or more substrates are covalently linked in series, either directly or directly, to each other, and wherein the CM is coupled to the AB. For example, CM may comprise a first substrate covalently linked either directly or indirectly, to a second substrate, where the first substrate is a substrate for a first protease, and the second substrate is a substrate for a second protease, in which the first and second protease are different proteases, and where the CM is coupled to the AB. In some embodiments, the first substrate and the second substrate are each a peptide of no more than about 25 amino acid residues long, or no more than about 24, or no more than about 23, or no more than about 22, or no more than about 21, or no more than about 20, or no more than about 19, or no more than about 18, or no more than about 17, or no more than about 15 amino acid residues long.

In some embodiments, the intact activatable antibody comprises at least one substrate for a protease selected from the group consisting of an MMP, thrombin, a neutrophil elastase, a cysteine protease, uPA, legumain, and matriptase. In some embodiments the activatable antibody comprises two prodomains, and hence, a first CM and a second CM. In certain of these embodiments, the first CM and the second CM comprise a substrate for the same protease. In some of these embodiments, the first CM comprises a first substrate and the second CM comprises a second substrate where the first substrate and the second substrate are substrates for two different proteases.

In certain embodiments, at least one CM in the activatable antibody (e.g., if a second prodomain is present in the activatable antibody, at least one of a first CM, and a second CM) comprises an amino acid sequence selected from the group consisting of SEQ ID NOs:1-67. In some embodiments, each CM present in the activatable antibody (e.g., if a second prodomain is present in the activatable antibody, both of a first CM and a second CM) independently comprises an amino acid sequence selected from the group consisting of SEQ ID NOs:1-67. In certain of these embodiments, each CM present in the activatable antibody comprises the same amino acid sequence (e.g., if a second prodomain is present in the activatable antibody, the first CM and the second CM comprise the same amino acid sequence).

The MM components of the activatable antibodies employed in the compositions and processes of the invention may be of any of a variety of lengths. In some embodiments, each MM present in the activatable antibody (e.g., a first MM; a first MM and a second MM; and the like) are each a peptide of no more than about 30 amino acid residues in length, or no more than about 29, or no more than about 28, or no more than about 27, or no more than about 26, or no more than about 25, or no more than about 24, or no more than about 23, or no more than about 22, or no more than about 21, or no more than about 20 amino acid residues in length. Each MM present reduces the ability of the corresponding AB to specifically bind to its respective biological target.

The MM can inhibit the binding of the activatable antibody to the biological target in a variety of ways. For example, the MM can bind to the AB thereby inhibiting binding of the activatable antibody to the biological target. The MM can allosterically or sterically inhibit binding of the activatable antibody to biological target. In some embodiments, the MM binds specifically to the AB. Suitable MMs may be identified using any of a variety of known techniques, including those described in U.S. Patent Application Publication Nos. 2009/0062142 and 2012/0244154, and PCT Publication No. WO 2014/026136, each of which is hereby incorporated by reference in their entirety.

Often, the dissociation constant (Kd) of the activatable antibody toward the biological target is greater than the Kd of the corresponding AB (absent the MM) toward the biological target.

In some embodiments, the MM reduces binding of the AB to the biological target by at least about 50%, or at least about 60%, or at least about 65%, or at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99%, and even 100%, for at least about 2 hours, or at least about 4 hours, or at least about 6 hours, or at least about 8 hours, or at least about 12 hours, or at least about 24 hours, or at least about 28 hours, or at least about 30 hours, or at least about 36 hours, or at least about 48 hours, or at least about 60 hours, or at least about 72 hours, or at least about 84 hours, or at least about 96 hours, or at least about 5 days, or at least about 10 days, or at least about 15 days, or at least about 30 days, or at least about 45 days, or at least about 60 days, or at least about 90 days, or at least about 120 days, or at least about 150 days, or at least about 180 days, or at least about 1 month, or at least about 2 months, or at least about 3 months, or at least about 4 months, or at least about 5 months, or at least about 6 months, or at least about 7 months, or at least about 8 months, or at least about 9 months, or at least about 10 months, or at least about 11 months, or at least about 12 months or more. Illustrative MMs include those described in, for example, WO 2009/025846, WO 2010/096838, WO 2010/081173, WO 2013/163631, WO 2013/192546, WO 2013/192550, WO 2014/026136, WO 2014/052462, WO 2014/107599, WO 2014/197612, WO 2015/013671, WO 2015/048329, WO 2015/066279, WO 2015/116933, WO 2016/014974, WO 2016/118629, WO 2016/149201, WO 2016/179285, WO 2016/179257, WO 2016/179335, WO 2017/011580, PCT/US2017/059740, and U.S. Provisional Application Ser. Nos. 62/469,429, 62/572,467, each of which is incorporated herein by reference in their entireties.

Activatable antibodies employed in the practice of the present invention may contain one or more additional structural elements, such as, for example, one or more linkers, or other amino acid residue or peptide that may impart a structural benefit, such as an N-terminal spacer amino acid residue or amino acid sequence, and the like.

Linkers suitable for use in the activatable antibodies of the compositions and processes of the present invention may be any of a variety of lengths. Suitable linkers include those having a length in the range of from about 1 to about 20 amino acid residues, or from about 1 to about 19 amino acid residues, or from about 1 to about 18 amino acid residues, or from about 1 to about 17 amino acid residues, or from about 1 to about 16 amino acid residues, or from about 1 to about 15 amino acid residues, or from about 2 to about 15 amino acid residues, or from about 3 to about 15 amino acid residues, or from about 3 to about 14 amino acid residues, or from about 3 to about 13 amino acid residues, or from about 3 to about 12 amino acid residues. In some embodiments, the activatable antibody comprises one or more linkers each independently comprising 1, 2, 3, 4, 5, 6, 7, 8, 9, 10, 11, 12, 13, 14, 15, 16, 17, 18, 19, or 20 amino acid residues.

Typically, the linker is a flexible linker comprising one or more amino acid residues selected from the group consisting of Gly, Ser, Ala, and Thr, and often, the linker comprises one or more amino acid residues selected from the group consisting of Gly and Ser. Exemplary flexible linkers include a glycine homopolymer $(G)_n$ (wherein n is an integer that is at least 1, or an integer in the range of from about 1 to about 30, or an integer in the range of from about 1 to about 25, or an integer in the range of from about 1 to about 20, or an integer in the range of from about 1 to about 15, or an integer in the range of from about 1 to about 10); a glycine-serine co-polymer, including, for example, $(GS)_n$ (wherein n is an integer that is at least 1, or an integer in the range of from about 1 to about 30, or an integer in the range of from about 1 to about 25, or an integer in the range of from about 1 to about 20, or an integer in the range of from about 1 to about 15, or an integer in the range of from about 1 to about 10), $(GSGGS)_n$ (SEQ ID NO:68) (wherein n is an integer that is at least 1, or an integer in the range of from about 1 to about 30, or an integer in the range of from about 1 to about 25, or an integer in the range of from about 1 to about 20, or an integer in the range of from about 1 to about 15, or an integer in the range of from about 1 to about 10), $(GGGS)_n$ (SEQ ID NO:69) (wherein n is an integer that is at least 1, or an integer in the range of from about 1 to about 30, or an integer in the range of from about 1 to about 25, or an integer in the range of from about 1 to about 20, or an integer in the range of from about 1 to about 15, or an integer in the range of from about 1 to about 10); a linker that comprises or consists of glycine and serine residues, such as, for example, GGSG (SEQ ID NO:70), GGSGG (SEQ ID NO:71), GSGSG (SEQ ID NO:72), GSGGG (SEQ ID NO:73), GSSGGSGGSGG (SEQ ID NO:74), GSSGGSGGSGGS (SEQ ID NO:75), GSSGGSGGSGGSGGS (SEQ ID NO:76), GSSGGSGGSG (SEQ ID NO:77), GSSGGSGGSGS (SEQ ID NO:78), GGGS (SEQ ID NO:79), GSSG (SEQ ID NO:80), GGGSSGGSGGSGG (SEQ ID NO:81), GGGSG (SEQ ID NO:82), GGGSGG (SEQ ID NO:152), GSGGGS (SEQ ID NO:153), GSGGSG (SEQ ID NO:154), GGS, and the like; a linker that comprises or consists of glycine, serine, and threonine residues, such as, for example, GSSGT (SEQ ID NO:83); a glycine-alanine co-polymer; an alanine-serine co-polymer; as well as other flexible linkers known in the art.

In some embodiments, activatable antibodies employed in the practice of the present invention may also comprise a spacer located, for example, at the amino terminus of the MM. In some embodiments, the spacer is joined directly to each MM of the activatable antibody, for example, in the structural arrangement, from N-terminus to C-terminus, of spacer-MM-CM-AB, wherein each "-" refers independently to a direct or indirect (i.e., via any of the linkers described herein). Illustrative spacer amino acid sequences may comprise or consist of any of the following exemplary amino acid sequences: QGQSGS (SEQ ID NO:84); GQSGS (SEQ ID NO:85); QSGS (SEQ ID NO:86); SGS; GS; S; QGQSGQG (SEQ ID NO:87); GQSGQG (SEQ ID NO:88); QSGQG (SEQ ID NO:89); SGQG (SEQ ID NO:90); GQG; QG; G; QGQSGQ (SEQ ID NO:91); GQSGQ (SEQ ID NO:92); QSGQ (SEQ ID NO:93); QGQSG (SEQ ID NO:94); QGQS (SEQ ID NO:95); SGQ; GQ; and Q.

As described above, purified activatable antibody compositions may be prepared for any of a variety of activatable antibodies. Illustrative activatable antibodies may comprise a set of VL and VH CDRs that result in binding specificity for any of a number of biological targets. Illustrative specific CDRs include, for example, those in a VL and VH that together form an AB that has binding specificity for human CD166, in which the VL comprises a VL CDR1 having the amino acid sequence of SEQ ID NO:96, a VL CDR2 having the amino acid sequence of SEQ ID NO:97, and a VL CDR3 having the amino acid sequence of SEQ ID NO:98, and the VH comprises a VH CDR1 having the amino acid sequence of SEQ ID NO:99, a VH CDR2 having the amino acid sequence of SEQ ID NO:100, and a VH CDR3 having the amino acid sequence of SEQ ID NO:101. In these activatable antibodies, the MM may comprise an amino acid sequence selected from the group consisting of SEQ ID NOs:102-119. A specific anti-CD166 activatable antibody comprising these CDRs comprises a first light chain and a second light chain that are identical, and a first heavy chain and a second heavy chain that are identical, wherein each of the first and second light chains comprise identical first and second VL amino acid sequences, identical first and second MMs, and identical first and second CMs, wherein each of the first and second light chains comprises the amino acid sequence of SEQ ID NO:120, and wherein each of the first and second heavy chains comprise an amino acid sequence selected from the group consisting of SEQ ID NO:121 and SEQ ID NO:122.

Another set of illustrative CDRs include those in a VL and VH that together form an AB that has binding specificity for human PD1, in which the VL comprises a VL CDR1 having the amino acid sequence of SEQ ID NO:123 or SEQ ID NO:129, a VL CDR2 having the amino acid sequence of SEQ ID NO:124, and a VL CDR3 having the amino acid sequence of SEQ ID NO:125, and the VH comprises a VH CDR1 having the amino acid sequence of SEQ ID NO:126, a VH CDR2 having the amino acid sequence of SEQ ID NO:127, and a VH CDR3 having the amino acid sequence of SEQ ID NO:128. In these activatable antibodies, the MM may comprise an amino acid sequence selected from the group consisting of SEQ ID NOs:130-280. A specific anti-PD1 activatable antibody comprising these CDRs comprises a first light chain and a second light chain that are identical, and a first heavy chain and a second heavy chain that are identical, wherein each of the first and second light chains comprise identical first and second VL amino acid sequences, identical first and second MMs, identical first and second CMs, and identical first and second light constant domains, wherein each of the first and second light chains comprises the amino acid sequence of SEQ ID NO:281, and wherein each of the first and second heavy chains comprise identical first and second VH amino acid sequences and identical first and second heavy constant domains, and wherein each of the first and second heavy chains comprise the amino acid sequence of SEQ ID NO:282.

Another illustrative set of CDRs include those in a VL and VH that together form an AB that has binding specificity for human PDL1, in which the VL comprises a VL CDR1 having the amino acid sequence of SEQ ID NO:283, a VL CDR2 having the amino acid sequence of SEQ ID NO:284, and a VL CDR3 having the amino acid sequence of SEQ ID NO:285, and the VH comprises a VH CDR1 having the amino acid sequence of SEQ ID NO:286, a VH CDR2 having the amino acid sequence of SEQ ID NO:287, and a VH CDR3 having the amino acid sequence of SEQ ID NO:288. In these activatable antibodies, the MM may comprise an amino acid sequence selected from the group consisting of SEQ ID NOs:289-313. A specific anti-PDL1 activatable antibody comprising these CDRs comprises a first light chain and a second light chain that are identical, and a first heavy chain and a second heavy chain that are identical, wherein each of the first and second light chains comprise identical first and second VL amino acid sequences, identical first and second MMs, identical first and second CMs, and identical first and second light constant domains, wherein each of the first and second light chains comprises the amino acid sequence of SEQ ID NO:314, and wherein each of the first and second heavy chains comprise identical first and second VH amino acid sequences and identical first and second heavy constant domains, and wherein each of the first and second heavy chains comprise the amino acid sequence of SEQ ID NO:315.

In another aspect, the present disclosure includes a method for determining or monitoring a relative quantity of an activatable antibody and a clipped variant thereof during a composition production process, by subjecting a sample composition comprising a population of activatable antibody and a population of clipped variants thereof to a gel capillary electrophoresis procedure. The gel capillary electrophoresis procedure may be reducing SDS-cGE or non-reducing SDS-cGE. In one aspect, the method involves separating the population of intact prodomain-encoding polypeptide from the population of clipped variants thereof using a reducing SDS-cGE procedure, and quantifying the relative amounts of the population of activatable antibody and the population of clipped variants thereof by determining the peak area corresponding to intact prodomain-encoding polypeptide and the peak area corresponding to the clipped prodomain-encoding polypeptide(s) thereof. In another aspect, the method involves separating the population of activatable antibody from the population of clipped variants thereof using a non-reducing SDS-cGE procedure, and quantifying the relative amounts of the population of activatable antibody and the population of clipped variants thereof by determining the peak area corresponding to intact activatable antibody and the peak area corresponding to clipped variant thereof.

In some aspects, the gel capillary electrophoresis method described herein can identify the presence of clipped variants that are not observed by other chromatography methods such as size exclusion chromatography (e.g., SE-HPLC), anion exchange chromatography, or cation exchange chromatography.

Thus, in some aspects, the quantitative gel capillary electrophoresis method described herein may be used to evaluate product and process quality for an activatable antibody, e.g., for quality control monitoring in a pharmaceutical production process. In some aspects, the method may be used to determine whether a purified composition comprising an activatable antibody is suitable for use to prepare a pharmaceutical composition. In some aspects, the present disclosure includes a method for preparing a pharmaceutical composition comprising an activatable antibody comprising a) providing a purified composition comprising intact activatable antibody and clipped variant thereof, b) separating intact activatable antibody species from clipped variants thereof by subjecting the sample to a reducing or non-reducing SDS-cGE procedure, c) quantifying the relative amounts of the population of activatable antibody and the population of clipped variants thereof by determining the peak area corresponding to intact activatable antibody or intact prodomain-containing polypeptide and the peak area corresponding to clipped antibody or clipped prodomain-containing polypeptide(s) thereof, and d) selecting the purified composition for use in the preparation of a pharmaceutical composition when the relative quantity of clipped variant in the sample is less than a threshold value. In some aspects, the threshold value is 3% clipped variant. In some aspects, the threshold value is 2.5%, 2%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, or 0.2%.

In some aspects, the present disclosure provides a method for determining or monitoring a relative percentage of an activatable antibody and a clipped variant thereof during a composition production process, the method including:
 a) subjecting a sample composition comprising a population of activatable antibody and a population of clipped variants thereof to a gel capillary electrophoresis procedure;
 b) separating the population of activatable antibody from the population of clipped variants thereof in the gel capillary electrophoresis procedure; and
 c) quantifying the relative amounts of the population of activatable antibody and the population of clipped variants thereof by determining the peak area corresponding to intact prodomain-containing polypeptide and the peak area corresponding to clipped prodomain-containing polypeptide(s) thereof.

In some aspects, the sample composition is a cell harvest composition of a cell expressing the activatable antibody. In some aspects, the sample composition has been subjected to protein affinity chromatography. In some aspects, the sample composition has been subjected to ion exchange chromatography. In some aspects, the sample composition has been subjected to anion exchange chromatography. In some aspects, the sample composition has been subjected to cation exchange chromatography. In some aspects, the sample composition has been subjected to hydrophobic interaction chromatography. In some aspects, the sample composition has been subjected to multimodal chromatography. In some aspects, the relative percentage is monitored by quantifying the relative percentages of the population of activatable antibody and the population of clipped variants thereof after each of two or more of cell harvest, protein affinity chromatography, ion exchange chromatography, hydrophobic interaction chromatography, and multimodal chromatography. In some aspects, step a) includes contacting the activatable antibody and clipped variant thereof in the sample composition with a reducing agent. In some aspects, the reducing agent is dithioerythritol (DTE), dithiothreitol (DTT), beta-mercaptoethanol, or a combination thereof. In some aspects, step a) includes contacting the activatable antibody and clipped variant thereof in the sample composition with a denaturing agent. In some aspects, the denaturing agent is sodium dodecyl sulfate (SDS). In some aspects, the method further includes performing a gel capillary electrophoresis procedure using SDS protein molecular weight standards and producing a molecular weight standard calibration curve. In some aspects, step c) includes obtaining an electropherogram containing a peak corresponding to each of the activatable antibody and clipped variant thereof subjected to the gel capillary electrophoresis procedure. In some aspects, the method further includes performing peak integration for each peak corresponding to each of the activatable antibody and clipped variant thereof to obtain the peak area of clipped prodomain-encoding polypeptide and the peak area of intact prodomain-encoding polypeptide.

The following examples further illustrate the practice of the invention, but should not be construed as limiting its scope in any way.

EXAMPLES

Example 1

Analytical Methods

A. Total Protein Concentration

Total protein concentration of the aqueous feedstock and purified product was determined by UV spectroscopy. Samples of each eluate were drawn immediately after the separation step and frozen until use in the assays described herein, e.g., total protein, SDS-cGE, SE-HPLC, and HCP ELISA assays. Samples were serial diluted in ultrapure water and protein absorbance was measured using a UV spectrophotometer (Cary 60 UV-Vis Spectrophotometer, Agilent Technologies, Inc.) at a wavelength of 280 nm. Protein concentrations were determined in accordance with Beer-Lambert law at a wavelength of 280 nm using a calculated molar extinction coefficient based on amino acid sequence. See, e.g., Pace, et al., *Protein Science* (1995) 4:2411.

Total protein yield was calculated as follows:

$$\text{Total Protein Yield} = \frac{(\text{volume} \times \text{protein concentration at 280 nm})_{eluate}}{(\text{volume} \times \text{concentration at 280 nm})_{aqueous\ feedstock}} \times 100$$

B. Quantitation of Activatable Antibody by Reducing Gel Capillary Electrophoresis Using Sodium Dodecyl Sulfate (SDS-cGE)

The purity of activatable antibody compositions (% intact activatable antibody) was determined using sodium dodecyl sulfate-capillary gel electrophoresis (SDS-cGE) methodology and UV photodiode array (PDA) detection (PA 800 Plus Pharmaceutical Analysis System, Beckman Coulter, Inc., Brea, CA). Samples containing activatable antibody were reduced using 0.5 M 1,4-Dithioerythritol (Sigma Aldrich, Cat. No. D8255-5G), then heat denatured in the presence of sodium dodecyl sulfate (SDS). Once denatured, the samples were separated by size in a capillary containing SDS polymer matrix, which provides sieving selectivity for the electrophoresis separation.

The assay for IgG purity and heterogeneity were run in accordance with manufacturer's instructions using reagents that include SDS Protein Sizing Standards, buffers, and parts provided in the IgG Purity and Heterogeneity Assay Kit from SCIEX, as described in the manufacturer's instruction manual.

A molecular weight standard calibration curve was generated in accordance with manufacturer's instructions. Peak integration was performed and the electropherogram was inspected to identify the polypeptide peaks. Peaks corresponding to clipped prodomain-encoding polypeptide appears before the expected intact prodomain-encoding polypeptide peak.

Percent intact activatable antibody (i.e., % intact activatable antibody or "purity") and percent clipped impurity are determined as follows:

$$\% \text{ intact activatable antibody} = \frac{\% \text{ Peak Area}_{intact}}{(\% \text{ Peak Area}_{clipped} + \% \text{ Peak Area}_{intact})} \times 100$$

$$\% \text{ clipped impurity} = \frac{\% \text{ Peak Area}_{clipped}}{(\% \text{ Peak Area}_{clipped} + \% \text{ Peak Area}_{intact})} \times 100$$

where:

$$\% \text{ Peak Area}_{clipped} = \frac{\left(\begin{array}{c}\text{Peak Area of clipped}\\ \text{prodomain-encoding polypeptide}\end{array}\right)}{\left(\begin{array}{c}\text{Total Peak Area corresponding}\\ \text{to all species detected}\end{array}\right)} \times 100$$

$$\% \text{ Peak Area}_{intact} = \frac{\left(\begin{array}{c}\text{Peak Area of intact}\\ \text{prodomain-encoding polypeptide}\end{array}\right)}{\left(\begin{array}{c}\text{Total Peak Area corresponding}\\ \text{to all species detected}\end{array}\right)} \times 100$$

C. Quantitation of HMWS by Size Exclusion High Performance Liquid Chromatography (SE-HPLC)

Size exclusion high performance liquid chromatography (SE-HPLC) was used to quantitate the amount of HMWS in the compositions described herein.

A mobile phase containing 200 mM $K_2PO_4$ and 150 mM KCl in UltraPure water was prepared (pH 6.8±0.1). Analysis was conducted on an HPLC system with autosampler (Dionex U3000 HPLC, Ultimate™ WPS-3000TBRS thermostatted biocompatible auto-sampler, Thermofisher Scientific) with column: analytical column (TSKgel G3000SWx1, Cat. No. 08541, Tosoh Bioscience LLC), guard column (TSKgel Guard SWx1, 6 mm×40 mm, Cat. No. 08543, Tosoh Bioscience LLC), and fitted pre-column (0.5 μm pre-column frit, Upchurch Scientific, Cat. No. A-318). The column was equilibrated with the mobile phase at a flow rate of 0.5 mL/min prior to sample analysis. Samples for analysis were diluted as necessary to a target concentration of 1 mg/mL with deionized or higher-grade water. Reference material was the corresponding monomeric activatable antibody (i.e., non-aggregated activated antibody). The reference material was diluted if necessary to a target concentration of 1 mg/mL with phosphate buffered saline (PBS).

Sample analysis was conducted at wavelengths of 220 nm (4 nm bandwidth) and 280 nm (4 nm bandwidth) for UV detection; ambient column oven temperature; 5°±3° C. sample temperature in auto-sampler; flow rate of 0.5 mL/min; and a run time of 30 min/sample. A formulation buffer blank injection was performed at the beginning of each series of samples prior to injection of the reference material. 20 μg of reference material was injected, followed by 40 μg of the test sample. 20 μg of the reference material was injected after each series of injection of each series of test samples.

The chromatograms of the test samples were integrated using Smart Cobra Wizard in Chromeleon 7 CDS (Thermo Scientific). Low molecular weight species (LMWS) is detected to the right side of the main (reference material) peak. Peak(s) corresponding to high molecular weight species (HMWS) is/are detected to the left side of the main peak. Relative peak area percent was calculated on the basis of the sum of all peak areas for all the peaks in the chromatogram (total peak area). The peak area of each HMWS peak observed was summed, and the sum was divided by the total peak area and multiplied by 100 to generate the percent peak area corresponding to HMWS (i.e., % HMWS).

D. Host Cell Protein (HCP)

Quantitation of HCP (in ppm (ng/ml product)) was determined using a commercially available HCP ELISA Kit in accordance with the manufacturer's directions (CHO HCP ELISA Kit, (F550), Cygnus Technologies, Inc.).

Example 2

Comparative Example: Cation Exchange Chromatography

Figure 5:
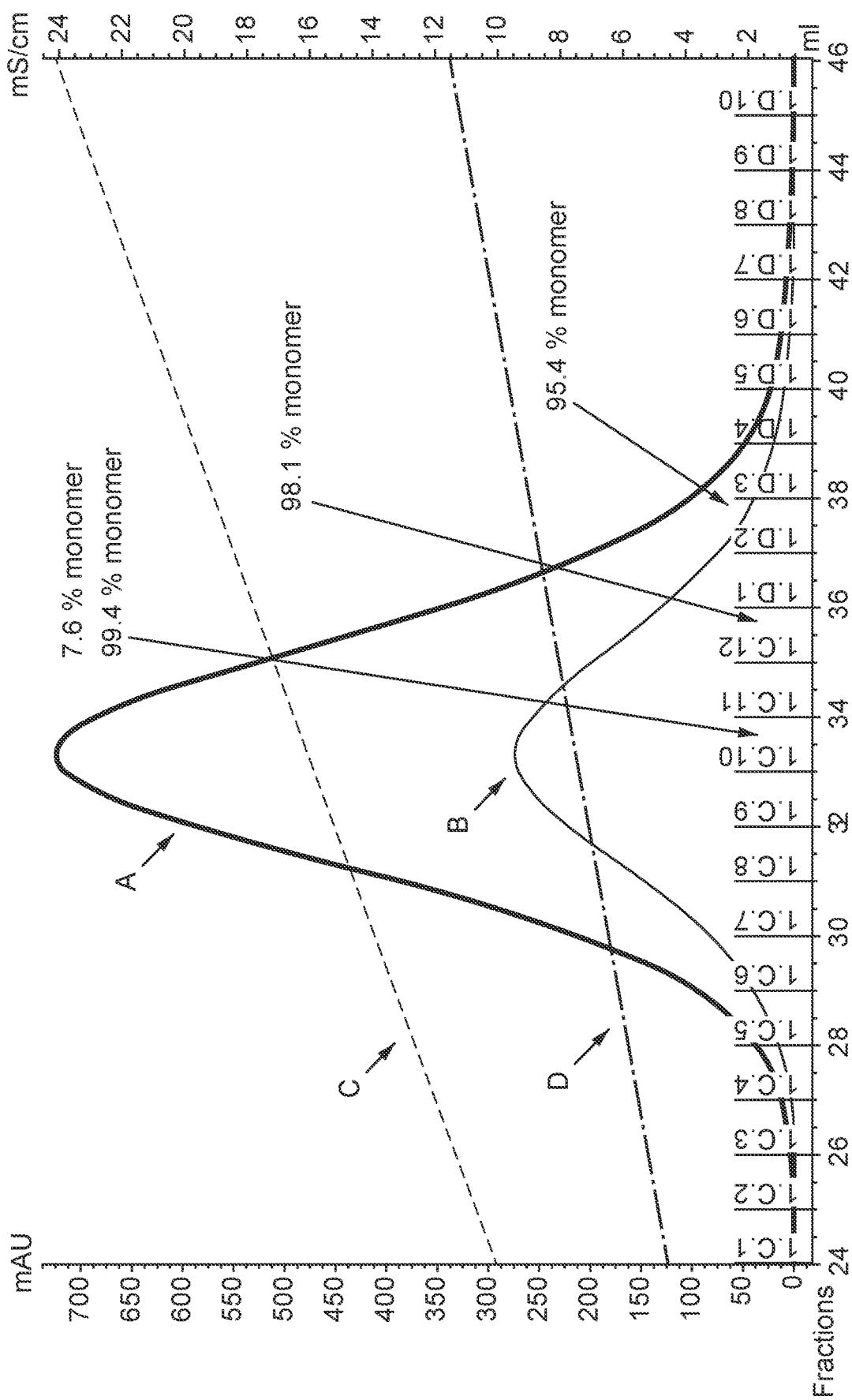
FIG. 5 depicts the evaluation of cation exchange chromatography for purifying an aqueous feedstock comprising intact activatable anti-CD166 antibody and a corresponding clipped impurity as described in Example 2. The column was eluted with a NaCl gradient by mixing a first buffer (25 mM NaOAc, 500 mM NaCl, pH 5.0 (80 CV grad)) into a second buffer (25 mM NaOAc, 25 mM NaCl, pH 5.0). Line "A" represents absorbance at 280 nm, Line "B" represents absorbance at 254 nm, Line "C" represents the conductivity in mS/cm, and Line "D" represents the percent of the first buffer mixed into the second buffer. The left y-axis presents absorbance in mAU, the right y-axis presents conductivity in mS/cm, and the x-axis presents fractions in mL.

Cation exchange chromatography was evaluated as a method of purifying an aqueous feedstock comprising intact activatable anti-CD166 antibody and a corresponding clipped impurity. The % clipped impurity of the aqueous feedstock was greater than 7.5%. The aqueous feedstock comprised >98% monomer. The anti-CD166 activatable antibody has two light chains and two heavy chains. Each light chain encodes an MM, a CM, a VL, and a constant region, and each has the amino acid sequence of SEQ ID NO: 120. Each heavy chain encodes a VH and a constant region, and each has the amino acid sequence of SEQ ID NO: 121. The VH and VL of each pair of heavy chain and light chain together form a Fab that is capable of binding human CD166, when not masked. The aqueous feedstock had a total protein load of 10 mg/ml, as determined by absorbance at a wavelength of 280 nm as described in Example 1A. The aqueous feedstock was adjusted to pH 5.0 by a 1:10 dilution with equilibrium buffer, and loaded onto a cation exchange resin (Capto S ImpAct, GE Lifesciences). The column was eluted with a NaCl gradient at pH 5 by mixing a first buffer (25 mM NaOAc, 500 mM NaCl, pH 5.0 (80 CV grad)) into a second buffer (25 mM NaOAc, 25 mM NaCl, pH 5.0). 1 mL fractions were collected. A single peak was observed in the chromatogram from which 1 ml fractions were collected and analyzed by reducing SDS-cGE. FIG. 5 presents the resulting chromatogram (line "A" presents absorbance at 280 nm). The results indicated that both intact activatable antibody and clipped impurity were present, but no (peak) separation was achieved. Accordingly, cation exchange chromatography did not result in effective separation of intact activatable antibody from clipped variants.

Example 3

Preparation of a Purified Composition of an Activatable Antibody

An aqueous feedstock comprising the same anti-CD166 activatable antibody described in Example 2 was treated using the hydrophobic chromatography process of the present invention.

Figure 4A:
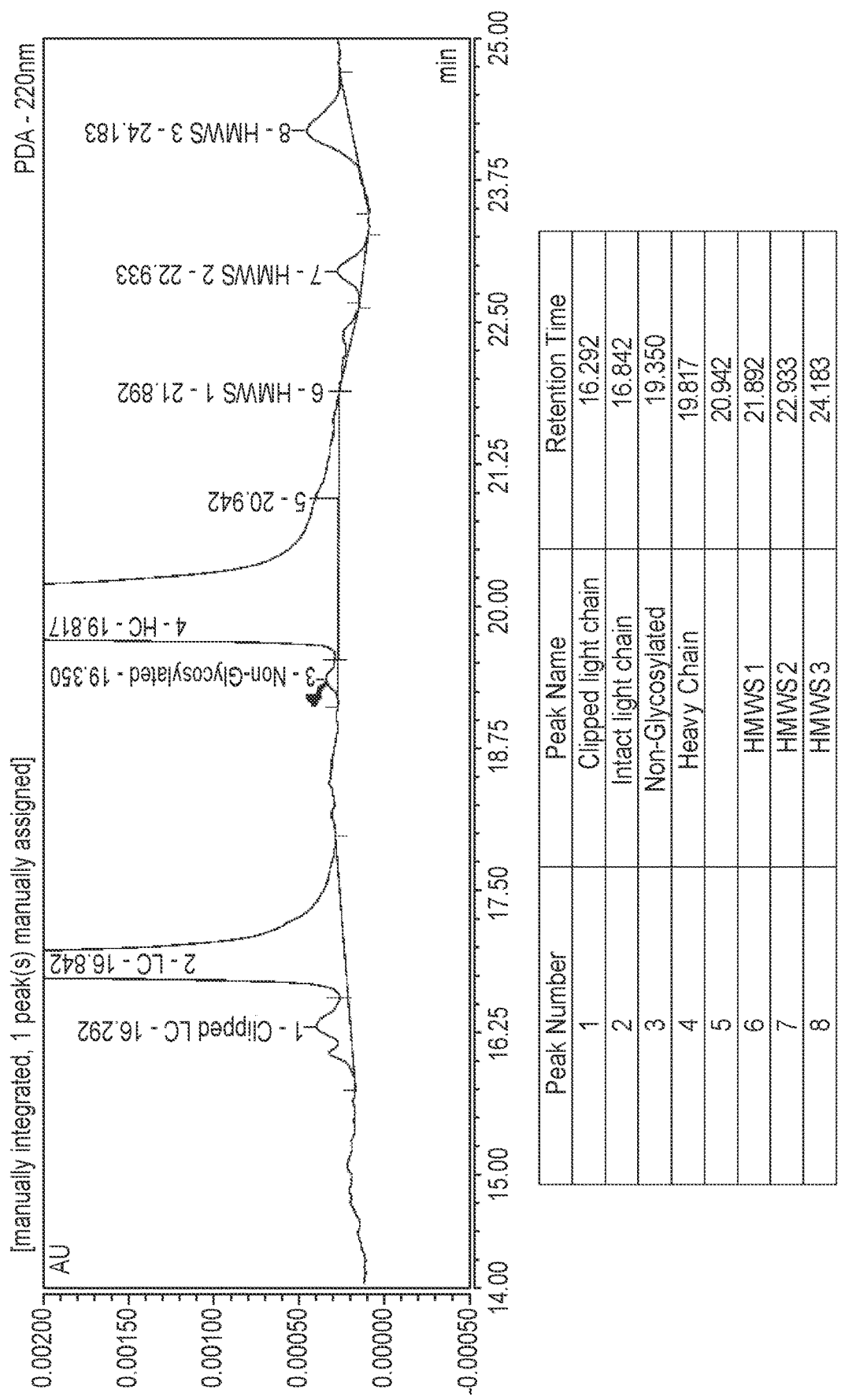
FIG. 4A depicts the results of reducing sodium dodecyl sulfate (SDS) capillary gel electrophoresis (SDS-cGE) performed on a sample comprising an anti-CD-166 activatable antibody following purification by protein A chromatography.
Figure 4B:
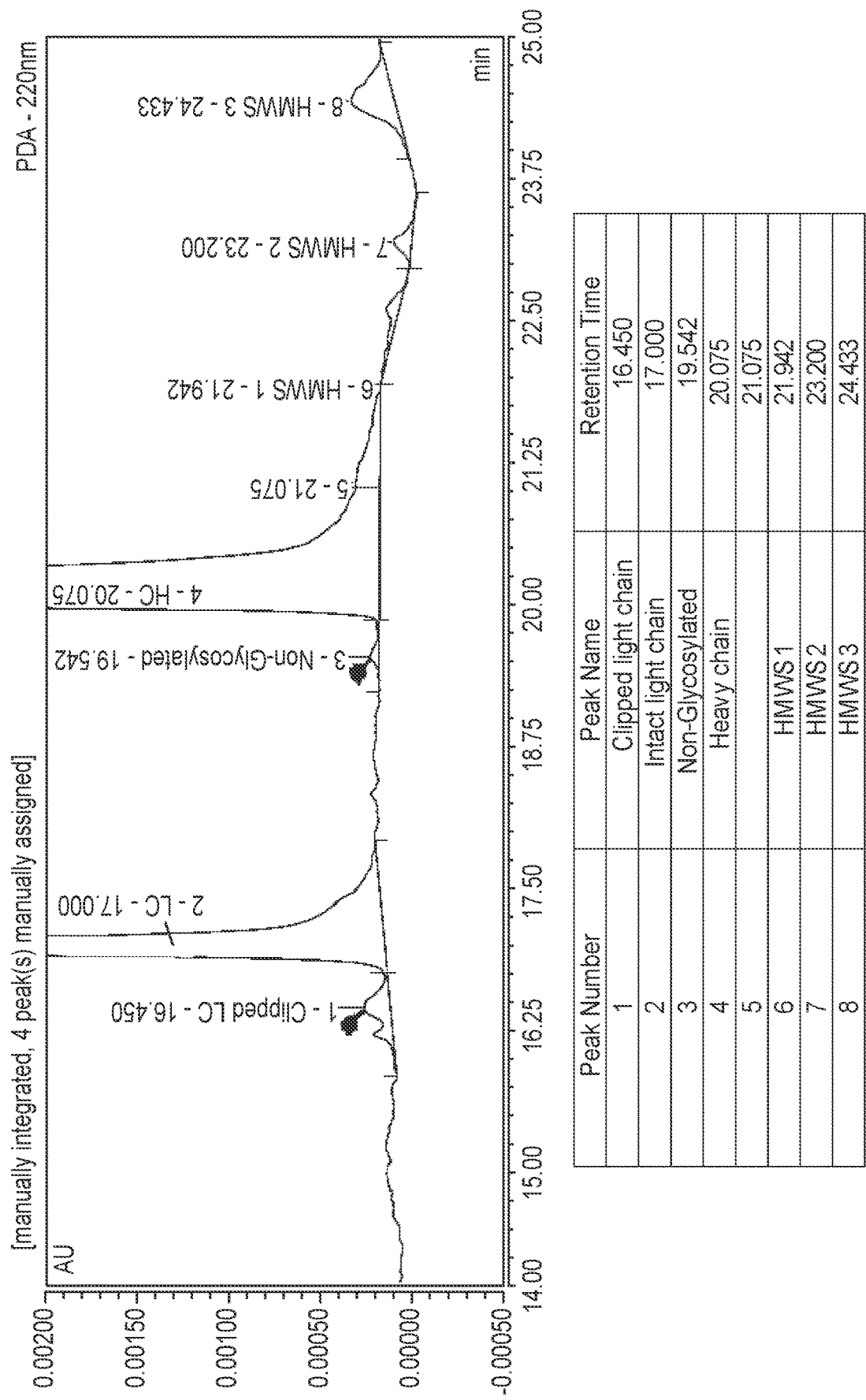
FIG. 4B depicts the results of reducing SDS-cGE performed on a sample of the eluate following anion ion exchange chromatography (anion IEX) for a sample comprising an anti-CD-166 activatable antibody. The aqueous feedstock for the anion IEX step comprised the eluate of the protein A chromatography step, the analysis of which is depicted in FIG. 4A.

Bioreactor harvest supernatant comprising intact activatable antibody and clipped impurity was subjected to a Protein A affinity chromatography step, followed by a virus inactivation step, and an anion exchange chromatography (anion IEX) step. These processes did not result in effective separation of intact activatable antibody from clipped variants. FIG. 4A depicts the results of SDS-cGE analysis of a sample of the eluate from the Protein A affinity chromatography step. A significant peak comprising clipped variant is observed (Peak 1, "clipped LC"). FIG. 4B depicts the results of SDS-cGE analysis of a sample of the eluate from the anion IEX step. A significant peak comprising clipped variant is observed (Peak 1, "clipped LC"), and the peak area of the clipped variant is not reduced compared to the eluate from the earlier Protein A chromatography step. Product from the anion IEX step was collected for further processing in a hydrophobic chromatography process that utilized a chromatography column loaded with a hydrophobic interaction chromatography stationary phase (i.e., a hydrophobic interaction chromatography (HIC) column).

The HIC column was conducted in bind-and-elute mode, using Capto™ Phenyl ImpRes (GE Healthcare) as resin (i.e., the stationary phase). This resin is an agarose-based resin with phenyl-containing ligands. An aqueous feedstock was prepared by conditioning product collected from the anion IEX step with a buffer containing 20 mM 2-(N-morpholino) ethanesulfonic acid (MES) and 1.5 M ammonium sulfate $(NH_4)_2SO_4$, pH 6. The aqueous feedstock was split into two aliquots, "Aliquot 1" and "Aliquot 2", for processing through the hydrophobic interaction chromatography column in two cycles, "Cycle 1" and "Cycle 2", respectively. The chromatography equipment, including column and buffers were placed in a temperature cabinet maintained at 22° C.±1° C.

The two aliquots were loaded onto the column in two cycles. Load densities were set to a maximum of 20 mg/mL (resin) for Cycle 1, and 16 mg/mL (resin) for Cycle 2. The column was eluted with a buffer containing 20 mM MES and 0.26 M ammonium sulfate, pH 6.0. The peak cut criteria (UV cell with 2 mm path length) were set to 50 mAU upward inflection and 600 mAU downward inflection. Eluate was collected and the column was cleaned with a 1 M NaOH solution. Total protein concentration was determined by UV absorbance as described in Example 1, and total protein yields were calculated based on volume and protein concentrations in the aqueous feedstock and eluate. The total protein yields for the hydrophobic chromatography process step are provided in Table 1, below.

TABLE 1

| Hydrophobic Chromatography Process (HIC) | |
| --- | --- |
| Sample | Yield (%, total protein) |
| Cycle 1 | >75% |
| Cycle 2 | >75% |

Relative quantities of intact activatable antibody and clipped impurity were determined by reducing SDS-cGE assays, as described in Example 1. The calculation of % intact activatable antibody and % clipped impurity was done on the basis of the light chain, which was the prodomain-encoding polypeptide.

A summary of process performance metrics for the hydrophobic chromatography process step is provided in Table 2, below.

TABLE 2

| Hydrophobic Chromatography Step - Process Performance | | | | | |
| --- | --- | --- | --- | --- | --- |
| Sample | % Intact Activatable Antibody by reducing SDS-cGE | % Clipped Impurity by reducing SDS-cGE | Fold Reduction, Clipped Impurity | % Reduction of Clipped Impurity | Quantity of Clipped Impurity in Eluate as % of Clipped Impurity in Aqueous Feedstock |
| Feed to Anion IEX step | >93% | >4% | — | — | |
| Product of Anion IEX/Feedstock to HIC Cycles 1, 2 | >93% | >4% | No reduction detected | No reduction detected | ~100% |
| HIC Eluate, Cycle 1 | >95% | <1% | >7 | >85% | <13% |
| HIC Eluate, Cycle 2 | >95% | <1% | >9 | >88% | <11% |

Figure 4C:
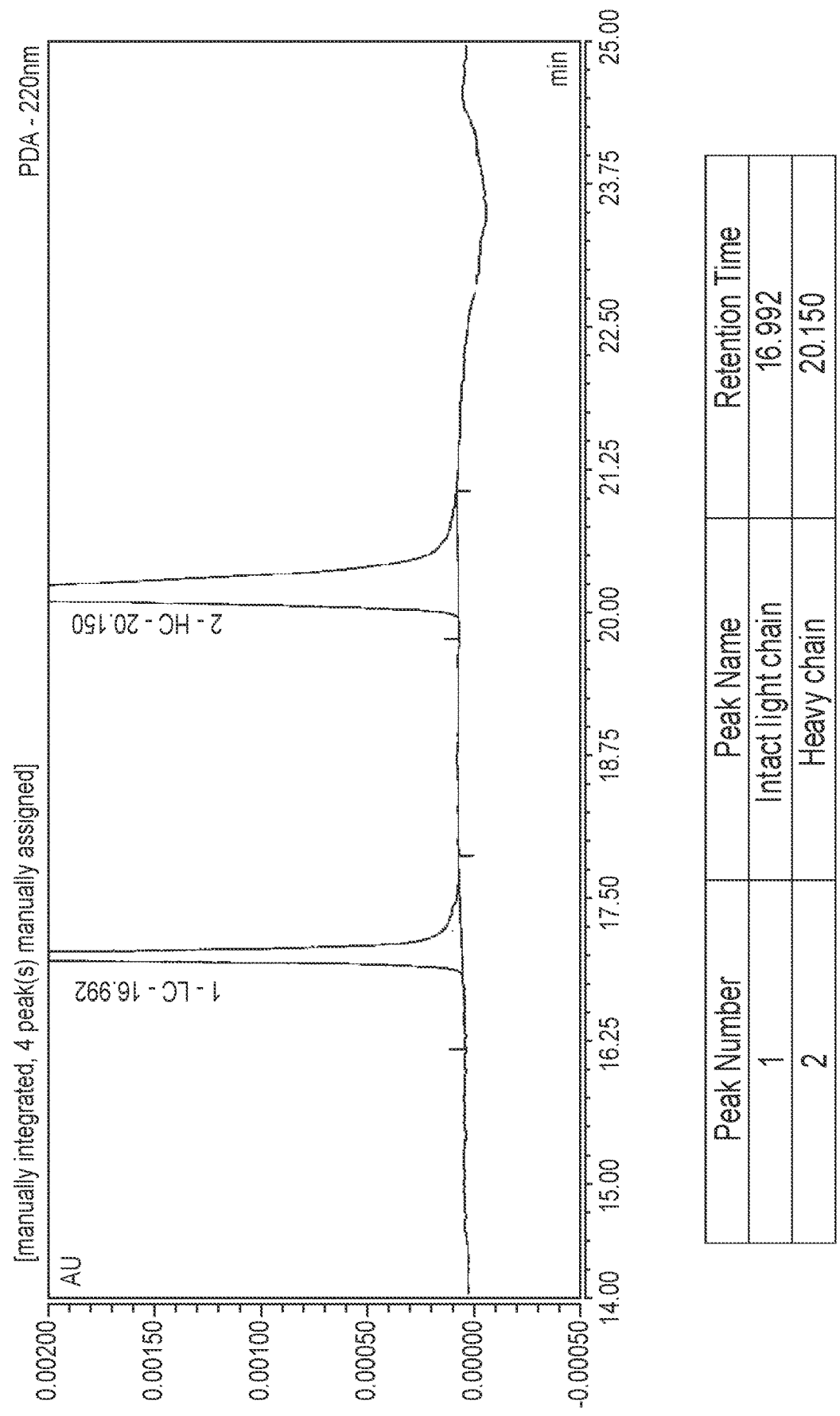
FIG. 4C depicts the results of reducing SDS capillary gel electrophoresis (SDS-cGE) performed on a sample comprising an anti-CD-166 activatable antibody following purification by hydrophobic interaction chromatography (HIC). The aqueous feedstock for the HIC step comprised the eluate of the anion IEX step, the analysis of which is depicted in FIG. 4B.

The anion IEX step (immediately upstream of the hydrophobic chromatography step) appeared to have no measurable impact on reducing the amount of clipped impurity from intermediate composition. See FIGS. 4A and 4B. In contrast, the hydrophobic chromatography process step (using a HIC column) had a significant impact on removing clipped impurity. See FIG. 4C, which depicts the results of SDS-cGE analysis of a sample of the eluate from the hydrophobic chromatography step. No peak corresponding to clipped variant is observed in FIG. 4C. The quantity of clipped species in the eluate, as compared to that in the aqueous feedstock, indicated that the hydrophobic chromatography process was effective at reducing the quantity of clipped impurity in the process stream by about 8- to 9.6-fold. Residual levels of clipped impurity in each eluate was substantially less than that present in the aqueous feedstock for both cycles. The purity level (% intact activatable antibody) remained high in the eluate of both cycles, with residual clipped impurity levels in the eluate at less than 1% clipped impurity, as measured by reducing SDS-cGE.

Host cell protein levels in the aqueous feedstock and eluate compositions were characterized using the HCP ELISA analytical method described in Example 1. The results are shown below in Table 3. The quantity of HCP is reported in ppm (i.e., HCP in ng/mL (as determined by a corresponding HCP ELISA) divided by product concentration in mg/mL (as determined by absorbance at a wavelength of 280 nm as described in Example 1A)).

TABLE 3

Quantitation of Host Cell Protein

| Sample | Host Cell Protein (ppm) | Fold Reduction | % Reduction | Quantity of HCP in Eluate, as % of HCP in Aqueous Feedstock |
|---|---|---|---|---|
| HIC (aqueous) Feedstock to Cycle 1, Cycle 2 | >20 ppm | — | — | |
| HIC Eluate, Cycle 1 | <4 ppm | 7 | >85% | <15% |
| HIC Eluate, Cycle 2 | <3 ppm | >7 | >85% | <15% |

The hydrophobic chromatography process step, using a HIC stationary phase, was effective at reducing HCP levels in the process stream by about 7-fold or more. Residual levels of HCP in the eluate were less than about 15% of feedstock levels.

HMWS levels were also assessed in the feedstock and eluate using the SE-HPLC assay described in Example 1. The results are shown below in Table 4.

TABLE 4

Quantitation of HMWS

| Sample | % HMWS (% Peak Area) | % Reduction of HMWS | Fold Reduction of HMWS | Quantity of HMWS in Eluate, as % of HMWS in Aqueous Feedstock |
|---|---|---|---|---|
| HIC Feedstock, Cycle 1 | >1 | — | — | — |
| HIC Feedstock, Cycle 2 | >1 | — | — | — |
| HIC Eluate, Cycle 1 | <1 | >85% | >7 | <15% |
| HIC Eluate, Cycle 2 | <1 | >90% | >13 | <10% |

The results indicated that the process was effective in removing 85% or more of HMWS from the process stream. The resulting eluate compositions contained less than about 15% (Cycle 1) and 10% (Cycle 2) of the HMWS present in the aqueous feedstocks.

A summary of the relative quantities of intact activatable antibody, clipped impurity, HCP, and HMWS in the eluate (purified) compositions is provided in Table 5, below.

TABLE 5

Purified Compositions

| Eluate Composition | Eluate, Cycle 1 | Eluate, Cycle 2 |
|---|---|---|
| % Intact Activatable Antibody* | >95% | >95% |
| % Clipped Impurity* | <1% | <1% |

TABLE 5-continued

Purified Compositions

| Eluate Composition | Eluate, Cycle 1 | Eluate, Cycle 2 |
|---|---|---|
| HCP (ppm) (by HCP ELISA, as described in Example 1) | <5 ppm | <5 ppm |
| % HMWS** | <0.5% | <0.5% |

*Determined by SDS-cGE, as described in Example 1, on the basis of % Peak Area corresponding to total light chain (intact and clipped).
**Determined by SE-HPLC, as described in Example 1.

Peak separation between the clipped impurity and the intact activatable antibody was achieved and resulted in successful separation of these species having very similar molecular weights and amino acid sequences. The results indicate that the hydrophobic chromatography process step was highly effective in generating compositions that are highly pure with respect to intact activatable antibody with low residual levels of clipped impurity, HCP, and HMWS.

Example 4

Preparation of a Purified Composition of an Activatable Anti-PD1 Antibody

Culture product comprising an anti-PD1 activatable antibody produced from two bioreactor runs (50 L scale ("Run 1") and 1,000 L scale ("Run 2")) was purified to remove various impurities, including clipped impurity. The anti-PD1 activatable antibody has two light chains, each encoding an MM, a CM, a VL, and a constant region, and each having the amino acid sequence of SEQ ID NO:281, and two heavy chains, each encoding a VH and a constant region, and each having the amino acid sequence of SEQ ID NO:282. Each VH and VL together form a Fab that is capable of binding the target, human PD1, when not masked.

The downstream purification process for each bioreactor run was similar. Bioreactor harvest supernatant comprising the activatable anti-PD1 antibody product was subjected to a Protein A-based affinity chromatography step, followed by a virus inactivation step, and an anion exchange chromatography (anion IEX) step. These processes did not result in effective separation of intact activatable antibody from clipped variants. Product was collected for further processing in a HIC column. The conductivity of product from the anion IEX step was adjusted to 127.0±13 mS/cm for Run 1 and 126 mS/cm±13 for Run 2 with 20 mM MES and 1.8 M ammonium sulfate, pH 6.0. Product was divided into aliquots that were sized according to the load capacity of the HIC column. Each aliquot (aqueous feedstock) was subsequently loaded onto a HIC column (Capto™ Phenyl ImpRes, GE Healthcare) operated in bind/elute (B/E) mode at a temperature of 22±1° C. The column was eluted with an aqueous solution of 20 mM MES, 0.4 M ammonium sulfate, pH 6.0. The eluate was collected and the column was stripped with a 0.01M NaOH solution.

Total protein concentration was determined by UV absorbance as described in Example 1, and total protein yields were calculated based on volume and protein concentrations in the aqueous feedstock and eluate. The total protein yield for each aliquot applied to the HIC column is presented in Table 6, below.

TABLE 6

Hydrophobic Chromatography Process (HIC), Total Protein Yield

| Run | Aliquot | Yield (%, total protein) |
|---|---|---|
| 1 | 1 | >80% |
|   | 2 | >80% |
| 2 | 1 | >75% |
|   | 2 | >75% |
|   | 3 | >80% |
|   | 4 | >80% |

The results indicate that total protein yields were relatively high for both runs.

Relative quantities of intact activatable antibody and clipped impurity were determined by reducing SDS-cGE assays as described in Example 1. The calculation of % intact activatable antibody and % clipped impurity was done on the basis of the light chain, which was the prodomain-encoding polypeptide.

A summary of process performance metrics for the hydrophobic chromatography process step for Run 1 and Run 2 is provided in Tables 7A and 7B, respectively, below.

TABLE 7A

Hydrophobic Chromatography Step - Process Performance, Run 1

| Sample | % Intact Activatable Antibody by Reducing SDS-cGE | % Clipped Activatable Antibody by Reducing SDS-cGE | Fold Reduction, Clipped Impurity | % Reduction, Clipped Impurity | Quantity of Clipped Species in Eluate, as % of Clipped Impurity in Aqueous Feedstock |
|---|---|---|---|---|---|
| Feed to Anion IEX step | >95% | >3% | — | — | — |
| Product of Anion IEX/Feed to HIC | >95% | >3% | No reduction detected | No reduction detected | ~100% |
| HIC Eluate, Run 1 | >97% | <1% | >37 | >96% | <4%% |
| HIC Eluate, Run 2 | >97% | <1% | >18% | >94% | <6% |

TABLE 7B

Hydrophobic Chromatography Step - Process Performance, Run 2

| Sample | % Intact Activatable antibody by Reducing SDS-cGE | % Clipped Impurity by Reducing SDS-cGE | Fold Reduction, Clipped Impurity | % Reduction, Clipped Impurity | Quantity of Clipped Impurity in Eluate, as % of Clipped Impurity in Aqueous Feedstock |
|---|---|---|---|---|---|
| Feed to Anion IEX step | >96% | >3% | — | — | — |
| Product of Anion IEX/Feedstock to HIC | >96% | >3% | No reduction detected | No reduction detected | ~100% |
| HIC Eluate, Aliquot 1 | >97% | <1% | >35 | >95% | <3% |
| HIC Eluate, Aliquot 2 | >97% | <1% | >17 | >93% | <6% |
| HIC Eluate, Aliquot 3 | >97% | <1% | >35 | >95% | <3% |
| HIC Eluate, Aliquot 4 | >97% | <1% | >17 | >93% | <6% |

As in the process scheme described in Example 3, the anion IEX step upstream of the hydrophobic chromatography step appeared to have no detectable impact on reducing the amount of clipped impurity from the intermediate composition. In contrast, the hydrophobic chromatography process step was highly effective at reducing the quantity of clipped impurity in the process stream. Intermediate compositions were also analyzed for the presence of HCP using the HCP ELISA assay described in Example 1. The results are shown in Tables 8A (Run 1) and 8B (Run 2).

TABLE 8A

Quantitation of Host Cell Protein (Run 1)

| Sample | Host Cell Protein (ppm HCP) | Fold Reduction | % Reduction | HCP in Eluate as % of HCP in Aqueous Feedstock |
|---|---|---|---|---|
| HIC Feedstock | >4 ppm | — | — | |
| HIC Eluate, Aliquot 1 | <2 ppm | >4 | >75% | <25 |
| HIC Eluate, Aliquot 2 | <2 ppm | >4 | >75% | <25 |

TABLE 8B

Quantitation of Host Cell Protein (Run 2)

| Sample | Host Cell Protein (ppm HCP) | Fold Reduction | % Reduction | HCP in Eluate as % of HCP in Feedstock |
|---|---|---|---|---|
| HIC Feedstock | >3 ppm | — | — | — |
| HIC Eluate, Aliquot 1 | <1 ppm | >4 | >75% | <25% |
| HIC Eluate, Aliquot 2 | <1 ppm | >4 | >75% | <25% |
| HIC Eluate, Aliquot 3 | <1 ppm | >4 | >75% | <25% |
| HIC Eluate, Aliquot 4 | <1 ppm | >4 | >75% | <25% |

The results indicate that the hydrophobic chromatography process step was effective at reducing the amount of HCP in the process stream by at least 4 fold.

HMWS levels were also assessed in aqueous feedstock and eluate samples using the SE-HPLC assay described in Example 1. The HMWS quantitation results are provided in Tables 9A (Run 1) and 9B (Run 2).

TABLE 9A

Quantitation of HMWS, (Run 1)

| Sample | HMWS (% Area) | Fold Reduction of HMWS | % Reduction of HMWS | HMWS in Eluate as % of HMWS in Aqueous Feedstock |
|---|---|---|---|---|
| Feed to HIC | >2% | — | — | — |
| HIC Eluate - Aliquot 1 | <1.5% | >2 | >55% | <45% |
| HIC Eluate - Aliquot 2 | <1% | >2.5 | >65% | <35% |

TABLE 9B

Quantitation of HMWS (Run 2)

| Sample | HMWS (% Area) | Fold Reduction of HMWS | % Reduction of HMWS | HMWS in Eluate as % of HMWS in Aqueous Feedstock |
|---|---|---|---|---|
| Feed to HIC | >2% | — | — | — |
| HIC Eluate - Aliquot 1 | <1% | >2.5 | >65% | <35% |
| HIC Eluate - Aliquot 2 | <1% | >2.5 | >65% | <35% |
| HIC Eluate - Aliquot 3 | <1% | >2.5 | >65% | <35% |
| HIC Eluate - Aliquot 4 | <1% | >4 | >75% | <25% |

The results indicate that the hydrophobic chromatography process was highly effective at reducing levels of HMWS from the process stream.

A summary of the relative quantities of intact activatable antibody, clipped impurity, HCP, and HMWS in the purified compositions generated by the hydrophobic chromatography process of the present invention is provided in Table 10A (Run 1) and Table 10B (Run 2), below.

TABLE 10A

Purified Compositions, Run 1 (50 L)

| Eluate Composition | Eluate, Aliquot 1 | Eluate, Aliquot 2 |
|---|---|---|
| % Intact Activatable Antibody* | >95% | >95% |
| % Clipped Impurity* | <1% | <1% |
| HCP (ppm) (by HCP ELISA, as described in Example 1) | <1.5 ppm | <1.5 ppm |
| % HMWS** | <1.5% | <1% |

*Determined by SDS-cGE, as described in Example 1, on the basis of % Peak Area corresponding to total light chain (intact and clipped).
**Determined by SE-HPLC, as described in Example 1.

TABLE 10B

Purified Compositions, Run 2 (1000 L)

| Eluate Composition | Eluate, Aliquot 1 | Eluate, Aliquot 2 | Eluate, Aliquot 3 | Eluate, Aliquot 4 |
|---|---|---|---|---|
| % Intact Activatable Antibody* | >95% | >95% | >95% | >95% |
| % Clipped impurity* | <1% | <1% | <1% | <1% |
| HCP (ppm) (HCP ELISA) | <1 ppm | <1 ppm | <1 ppm | <1 ppm |
| % HMWS** | <1% | <1% | <1% | <1% |

*Determined by SDS-cGE, as described in Example 1, on the basis of % Peak Area corresponding to total light chain (intact and clipped).
**Determined by SE-HPLC, as described in Example 1.

The results indicate that the hydrophobic chromatography process of the present invention, in this case using a HIC column, was successful in removing clipped species, HCP, and HMWS from the process stream, thus generating highly pure compositions of intact activatable antibody.

Example 5

Preparation of a Purified Composition of an Anti-PDL1 Activatable Antibody

Culture product comprising an anti-PDL1 activatable antibody was treated using the hydrophobic chromatography process of the present invention to remove various impurities. The anti-PDL1 activatable antibody has two light chains, each encoding an MM, a CM, a VL, and a constant region, and each having the amino acid sequence of SEQ ID NO:314, and two heavy chains, each encoding a VH and a constant region, and each having the amino acid sequence of SEQ ID NO:315. Each VH and VL together form a Fab that is capable of binding the target human PDL1, when not masked.

Bioreactor harvest supernatant comprising intact activatable antibody and clipped impurity was subjected to a Protein A affinity chromatography step, followed by a virus inactivation step, and an anion IEX step. These processes did not result in effective separation of intact activatable antibody from clipped variants. Product from the anion IEX step was collected for further processing in a hydrophobic chromatography process that utilized a chromatography column loaded with a multimodal chromatography stationary phase (i.e., a multimodal chromatography (MMC) column).

The MMC column was conducted in bind-and-elute mode, using Capto™ MMC ImpRes (GE Healthcare) as resin (i.e., a stationary phase with N-benzoyl-homocysteine ligands) at a temperature of 22±4° C.

Intermediate product composition (pH 5.9) was conditioned with 25 mM MES, 30 mM NaCl, then split into two aliquots (aqueous feedstock) and processed in two cycles. The load density was 30 mg/ml$_{resin}$ for each run. The column was washed, then eluted with 25 mM MES, 30 mM NaCl, 90 mM Arginine HCl at pH 5.9. The eluate was collected and the column was cleaned with a 1 M NaOH solution.

Total protein concentration was determined by UV absorbance, as described in Example 1, and total protein yields were calculated based on volume and protein concentrations in the aqueous feedstock and eluate. The total protein yields for the hydrophobic chromatography process step are provided in Table 11, below.

TABLE 11

| Hydrophobic Chromatography Process (MMC) | |
|---|---|
| Sample | Yield (%, total protein) |
| MMC Feedstock | — |
| Eluate, Aliquot 1 | >75% |
| Eluate, Aliquot 2 | >75% |

The results indicate that relatively high total protein yields were obtained from the process.

Relative quantities of intact activatable antibody and clipped impurity were determined by reducing SDS-cGE, as described in Example 1. The results are summarized in Table 12.

TABLE 12

| Hydrophobic Chromatography Step using MMC - Process Performance | | | | | |
|---|---|---|---|---|---|
| Sample | % Intact Activatable Antibody by Reducing SDS-cGE | % Clipped Impurity by Reducing SDS-cGE | Fold Reduction, Clipped Impurity | % Reduction of Clipped Impurity | Quantity of Clipped Impurity in Eluate, as % of Clipped Impurity in Aqueous Feedstock |
| Feed to Anion IEX step | >95% | >0.5% | — | — | — |
| Product of Anion IEX/Aqueous Feedstock to MMC | >95% | >0.5% | No reduction detected | No reduction detected | ~100% |
| MMC Eluate, Aliquot 1 | >98% | <0.5% | >8 | >85% | <12% |
| MMC Eluate, Aliquot 2 | >98% | <0.5% | >8 | >85% | <12% |

The results indicate that implementation of the hydrophobic chromatography process, in this case, using an MMC column, effectively removed more than 85% of clipped impurity from the process stream, resulting in a greater than 8-fold reduction of this impurity. Levels of intact activatable antibody (purity) were high in both eluant samples at greater than 98%. By contrast, the anion IEX step did not appear effective at reducing the level of clipped impurity in the process stream.

MMC feedstock and eluate compositions were also analyzed for the presence of HCP. The results are shown in Table 13.

TABLE 13

Quantitation of Host Cell Protein

| Sample | Host Cell Protein (ppm HCP) | Fold Reduction | % Reduction | Quantity of HCP in Eluate as % of HCP in MMC Feedstock |
|---|---|---|---|---|
| MMC Aqueous Feedstock | >55 ppm | — | — | — |
| MMC Eluate, Aliquot 1 | <9 ppm | >6 | >84% | <16% |
| MMC Eluate, Aliquot 2 | <6 ppm | >11 | >90% | <9% |

The results indicate that the hydrophobic chromatography step, using an MMC chromatography column, was effective at reducing the amount of HCP in the MMC feedstock composition by greater than 6-fold (greater than 84%) for Aliquot 1 and greater than 11-fold (greater than 90%) for Aliquot 2. Residual quantities of HCP in the eluate were less than 16% and about 9% of feedstock levels for Aliquots 1 and 2, respectively.

HMWS quantities were also assessed in feedstock and eluate samples using the SE-HPLC assay described in Example 1. The HMWS quantitation results are provided in Table 14, below.

TABLE 14

Quantitation of HMWS

| Sample | % HMWS (% Area) | Fold Reduction | % Reduction | Quantity of HMWS in Eluate as % of HMWS in Aqueous Feedstock |
|---|---|---|---|---|
| Product of Anion IEX Step/Feed to MMC | >3% | — | — | — |
| MMC Eluate - Aliquot 1 | <1% | >4 | >75% | <25 |
| MMC Eluate - Aliquot 2 | <1% | >9 | >85% | <12 |

The results indicate that the hydrophobic chromatography process step, in this case using an MMC column, was highly effective at removing a substantial fraction of HMWS from the process stream.

A summary of the relative quantities of intact activatable antibody, clipped impurity, HCP, and HMWS in the purified compositions generated by the hydrophobic chromatography process of the present invention is provided in Table 15, below.

TABLE 15

Purified Compositions

| Eluate Composition | Eluate, Run 1 | Eluate, Run 2 |
|---|---|---|
| % Intact Activatable Antibody* | >98% | >98% |
| % Clipped impurity* | <0.5% | <0.5% |
| HCP (ppm) (by HCP ELISA, as described in Example 1) | <9 ppm | <5 ppm |
| % HMWS** | <1 | <1 |

*Determined by SDS-cGE, as described in Example 1, on the basis of % Peak Area corresponding to total light chain (intact and clipped).
**Determined by SE-HPLC, as described in Example 1.

The results indicate that the hydrophobic chromatography process step was highly effective in generating relatively pure compositions of intact activatable antibody that have, if at all present, low residual levels of clipped impurity, HCP, and HMWS.

Example 6

Preparation of a Purified Composition of an Activatable Anti-PDL1 Antibody from Aqueous Feedstock with High Levels of Clipped Impurity A. Aqueous Feedstock: 3.1% Clipped Impurity Aqueous feedstock comprising the anti-PDL1 antibody described in Example 5 was loaded onto an MMC column. The composition of the aqueous feedstock included 3.1% clipped impurity and greater than 98% of the activatable antibody in monomeric form (i.e., less than 2% HMWS).

The MMC column was conducted in bind-and-elute mode, using Capto™ MMC ImpRes (GE Healthcare) as resin (i.e., a stationary phase with N-benzoyl-homocysteine ligands) at a temperature of 22±4° C. The aqueous feedstock was conditioned with 25 mM MES, 30 mM NaCl (pH 6). The column was washed with 25 mM MES, 30 mM NaCl, 20 mM Arginine HCl at pH 6, then eluted with 25 mM MES, 30 mM NaCl, 90 mM Arginine HCl at pH 6. The eluate was collected and the column was cleaned with a 1 M NaOH solution.

Total protein concentration was determined by UV absorbance, as described in Example 1, and total protein yield was calculated based on volume and protein concentrations in the aqueous feedstock and eluate. The level of clipped impurity in the resulting eluate was reduced by greater than 7.5-fold, such that less than about 13% of the clipped impurity in the aqueous feedstock remained in the eluate. The quantity of monomeric activatable antibody remained at greater than 98%. Total protein yield was greater than 65%.

B. Aqueous Feedstock: 13.5% Clipped Impurity

Aqueous feedstock comprising the anti-PDL1 antibody described in Example 5 was loaded onto an MMC column (loaded with Capto™ ImpRes resin (GE Healthcare), and processed as described in part A, above. The composition of the aqueous feedstock included 13.5% clipped impurity and 96.8% of the activatable antibody in monomeric form (i.e., greater than 3% HMWS). The level of clipped impurity in the resulting eluate was reduced by greater than 7-fold (<14% of the clipped impurity in the aqueous feedstock) and the quantity of monomeric activatable antibody was greater than 98% (i.e., less than 2% HMWS). Total protein yield was greater than 65%.

The results from these experiments suggest that the hydrophobic chromatography process can be employed to purify aqueous feedstock with relatively high clipped impurity loads. The hydrophobic chromatography process results in a composition that is substantially depleted of clipped impurity.

The sequence listing is shown below in Table 16.

TABLE 16

Amino Acid Sequences

| SEQ ID NO. | DESCRIPTION | SEQUENCE |
|---|---|---|
| 1 | CM | LSGRSDNH |
| 2 | CM | TGRGPSWV |
| 3 | CM | PLTGRSGG |
| 4 | CM | TARGPSFK |
| 5 | CM | NTLSGRSENHSG |
| 6 | CM | NTLSGRSGNHGS |
| 7 | CM | TSTSGRSANPRG |
| 8 | CM | TSGRSANP |
| 9 | CM | VHMPLGFLGP |
| 10 | CM | AVGLLAPP |
| 11 | CM | AQNLLGMV |
| 12 | CM | QNQALRMA |
| 13 | CM | LAAPLGLL |
| 14 | CM | STFPFGMF |
| 15 | CM | ISSGLLSS |
| 16 | CM | PAGLWLDP |
| 17 | CM | VAGRSMRP |
| 18 | CM | VVPEGRRS |
| 19 | CM | ILPRSPAF |
| 20 | CM | MVLGRSLL |
| 21 | CM | QGRAITFI |
| 22 | CM | SPRSIMLA |
| 23 | CM | SMLRSMPL |
| 24 | CM | ISSGLLSGRSDNH |
| 25 | CM | AVGLLAPPGGLSGRSDNH |
| 26 | CM | ISSGLLSSGGSGGSLSGRSDNH |
| 27 | CM | LSGRSGNH |
| 28 | CM | SGRSANPRG |
| 29 | CM | LSGRSDDH |
| 30 | CM | LSGRSDIH |
| 31 | CM | LSGRSDQH |
| 32 | CM | LSGRSDTH |
| 33 | CM | LSGRSDYH |
| 34 | CM | LSGRSDNP |
| 35 | CM | LSGRSANP |
| 36 | CM | LSGRSANI |
| 37 | CM | LSGRSDNI |
| 38 | CM | MIAPVAYR |
| 39 | CM | RPSPMWAY |
| 40 | CM | WATPRPMR |
| 41 | CM | FRLLDWQW |
| 42 | CM | ISSGL |
| 43 | CM | ISSGLLS |
| 44 | CM | ISSGLL |
| 45 | CM | ISSGLLSGRSANPRG |
| 46 | CM | AVGLLAPPTSGRSANPRG |
| 47 | CM | AVGLLAPPSGRSANPRG |
| 48 | CM | ISSGLLSGRSDDH |
| 49 | CM | ISSGLLSGRSDIH |
| 50 | CM | ISSGLLSGRSDQH |
| 51 | CM | ISSGLLSGRSDTH |
| 52 | CM | ISSGLLSGRSDYH |
| 53 | CM | ISSGLLSGRSDNP |
| 54 | CM | ISSGLLSGRSANP |
| 55 | CM | ISSGLLSGRSANI |
| 56 | CM | AVGLLAPPGGLSGRSDDH |
| 57 | CM | AVGLLAPPGGLSGRSDIH |
| 58 | CM | AVGLLAPPGGLSGRSDQH |
| 59 | CM | AVGLLAPPGGLSGRSDTH |
| 60 | CM | AVGLLAPPGGLSGRSDYH |
| 61 | CM | AVGLLAPPGGLSGRSDNP |
| 62 | CM | AVGLLAPPGGLSGRSANP |
| 63 | CM | AVGLLAPPGGLSGRSANI |
| 64 | CM | ISSGLLSGRSDNI |
| 65 | CM | AVGLLAPPGGLSGRSDNI |
| 66 | CM | GLSGRSDNHGGAVGLLAPP |
| 67 | CM | GLSGRSDNHGGVHMPLGFLGP |
| 68 | Linker | GSGGS |
| 69 | Linker | GGGS |
| 70 | Linker | GGSG |
| 71 | Linker | GGSGG |
| 72 | Linker | GSGSG |

TABLE 16-continued

Amino Acid Sequences

| SEQ ID NO. | DESCRIPTION | SEQUENCE |
|---|---|---|
| 73 | Linker | GSGGG |
| 74 | Linker | GSSGGSGGSGG |
| 75 | Linker | GSSGGSGGSGGS |
| 76 | Linker | GSSGGSGGSGGSGGGS |
| 77 | Linker | GSSGGSGGSG |
| 78 | Linker | GSSGGSGGSGS |
| 79 | Linker | GGGS |
| 80 | Linker | GSSG |
| 81 | Linker | GGGSSGGSGGSGG |
| 82 | Linker | GGGSG |
| 83 | Linker | GSSGT |
| 84 | Spacer | QGQSGS |
| 85 | Spacer | GQSGS |
| 86 | Spacer | QSGS |
| 87 | Spacer | QGQSGQG |
| 88 | Spacer | GQSGQG |
| 89 | Spacer | QSGQG |
| 90 | Spacer | SGQG |
| 91 | Spacer | QGQSGQ |
| 92 | Spacer | GQSGQ |
| 93 | Spacer | QSGQ |
| 94 | Spacer | QGQSG |
| 95 | Spacer | QGQS |
| 96 | VL CDR1 | RSSKSLLHSNGITYLY |
| 97 | VL CDR2 | QMSNLAS |
| 98 | VL CDR3 | AQNLELPYT |
| 99 | VH CDR1 | GFSLSTYGMGVG |
| 100 | VH CDR2 | NIWWSEDKH |
| 101 | VH CDR3 | IDYGNDYAFTY |
| 102 | MM | LCHPLVLSAWESCSS |
| 103 | MM | LCHPAVLSAWESCSS |
| 104 | MM | LCHPLVASAWESCSS |
| 105 | MM | LEGWCLHPLCLWGAG |
| 106 | MM | LCAPLVLSAWESCSS |
| 107 | MM | LCHALVLSAWESCSS |
| 108 | MM | LCHPLALSAWESCSS |
| 109 | MM | LCHPLVLSAAESCSS |
| 110 | MM | LCHPLVLSAWASCSS |
| 111 | MM | HPLVL |
| 112 | MM | LEGACLHPLCLWGAG |
| 113 | MM | LEGWCAHPLCLWGAG |
| 114 | MM | LEGWCLAPLCLWGAG |
| 115 | MM | LEGWCLHACLWGAG |
| 116 | MM | LEGWCLHPACLWGAG |
| 117 | MM | LEGWCLHPLCAWGAG |
| 118 | MM | LEGWCLHPLCLAGAG |
| 119 | MM | CLHPLC |
| 120 | Human αCD166 CX-191/CX-2009 Light Chain (spacer-MM-LP1-CM-LP2-Ab) | QGQSGQGLCHPAVLSAWESCSSG GGSSGGSAVGLLAPPGGLSGRSDN HGGSDIVMTQSPLSLPVTPGEPASI SCRSSKSLLHSNGITYLYWYLQKP GQSPQLLIYQMSNLASGVPDRFSG SGSGTDFTLKISRVEAEDVGVYYC AQNLELPYTFGQGTKLEIKRTVAA PSVFIFPPSDEQLKSGTASVVCLLN NFYPREAKVQWKVDNALQSGNSQ ESVTEQDSKDSTYSLSSTLTLSKAD YEKHKVYACEVTHQGLSSPVTKSF NRGEC |
| 121 | Human αCD166 Heavy Chain (HuCD166_HcCDdes-HC)) | QITLKESGPTLVKPTQTLTLTCTFS GFSLSTYGMGVGWIRQPPGKALE WLANIWWSEDKHYSPSLKSRLTIT KDTSKNQVVLTITNVDPVDTATYY CVQIDYGNDYAFTYWGQGTLVTV SSASTKGPSVFPLAPSSKSTSGGTA ALGCLVKDYFPEPVTVSWNSGAL TSGVHTFPAVLQSSGLYSLSSVVT VPSSSLGTQTYICNVNHKPSNTKV DKKVEPKSCDKTHTCPPCPAPELL GGPSVFLFPPKPKDTLMISRTPEVT CVVVDVSHEDPEVKFNWYVDGVE VHNAKTKPREEQYNSTYRVVSVL TVLHQDWLNGKEYKCKVSNKALP APIEKTISKAKGQPREPQVYTLPPS REEMTKNQVSLTCLVKGFYPSDIA VEWESNGQPENNYKTTPPVLDSD GSFFLYSKLTVDKSRWQQGNVFSC SVMHEALHNHYTQKSLSLSPG |
| 122 | Human αCD166 Heavy Chain (HuCD166_HcC) | QITLKESGPTLVKPTQTLTLTCTFS GFSLSTYGMGVGWIRQPPGKALE WLANIWWSEDKHYSPSLKSRLTIT KDTSKNQVVLTITNVDPVDTATYY CVQIDYGNDYAFTYWGQGTLVTV SSASTKGPSVFPLAPSSKSTSGGTA ALGCLVKDYFPEPVTVSWNSGAL TSGVHTFPAVLQSSGLYSLSSVVT VPSSSLGTQTYICNVNHKPSNTKV DKKVEPKSCDKTHTCPPCPAPELL GGPSVFLFPPKPKDTLMISRTPEVT CVVVDVSHEDPEVKFNWYVDGVE VHNAKTKPREEQYNSTYRVVSVL TVLHQDWLNGKEYKCKVSNKALP APIEKTISKAKGQPREPQVYTLPPS REEMTKNQVSLTCLVKGFYPSDIA VEWESNGQPENNYKTTPPVLDSD GSFFLYSKLTVDKSRWQQGNVFSC SVMHEALHNHYTQKSLSLSPGK |

TABLE 16-continued

Amino Acid Sequences

| SEQ ID NO. | DESCRIPTION | SEQUENCE |
|---|---|---|
| 123 | CX-188 1.5 VL CDR1 | RASESVDAYGISFMN |
| 124 | 1.5 VL CDR2 | AASNQGS |
| 125 | 1.5 VL CDR3 | QQSKDVPWT |
| 126 | 1.5 VH CDR1 | GFTFSGYAMS |
| 127 | 1.5 VH CDR2 | YISNSGGNAH |
| 128 | 1.5 VH CDR3 | EDYGTSPFVY |
| 129 | 1.4 VL CDR1 | RASESVDSYGISFMN |
| 130 | PD001-Mask | AMSGCSWSAFCPYLA |
| 131 | PD002 | DVNCAIWYSVCTTVP |
| 132 | PD003 | LVCPLYALSSGVCMG |
| 133 | PD004 | SVNCRIWSAVCAGYE |
| 134 | PD005 | MLVCSLQPTAMCERV |
| 135 | PD006 | APRCYMFASYCKSQY |
| 136 | PD007 | VGPCELTPKPVCNTY |
| 137 | PD008 | ETCNQYERSSGLCFA |
| 138 | PD009 | APRTCYTYQCSSFYT |
| 139 | PD010 | GLCSWYLSSSGLCVD |
| 140 | PD011 | VPWCQLTPRVMCMWA |
| 141 | PD012 | NWLDCQFYSECSVYG |
| 142 | PD013 | SCPLYVMSSFGGCWD |
| 143 | PD014 | MSHCWMFSSSCDGVK |
| 144 | PD015 | VSYCTWLIEVTCLRG |
| 145 | PD016 | VLCAAYALSSGICGG |
| 146 | PD017 | TTCNLYQQSSMFCNA |
| 147 | PD018 | APRCYMFASYCKSQY |
| 148 | PD019 | PCDQNPYFYPYVCHA |
| 149 | PD020 | SVCPMYALSSMLCGA |
| 150 | PD021 | LSVECYVFSRCSSLP |
| 151 | PD022 | FYCTYLVSLTCHPQ |
| 152 | Linker | GGGSGG |
| 153 | Linker | GSGGGS |
| 154 | Linker | GSGGSG |
| 155 | PD023 | SMAGCQWSSFCVQRD |
| 156 | PD024 | IYSCYMFASRCTSDK |
| 157 | PD025 | SRCSVYEVSSGLCDW |
| 158 | PD026 | GMCSAYAYSSKLCTI |
| 159 | PD027 | MTTNTCNLLCQQFLT |
| 160 | PD028 | FQPCLMFASSCFTSK |
| 161 | PD029 | WNCHPAGVGPVFCEV |
| 162 | PD030 | ALCSMYLASSGLCNK |
| 163 | PD031 | NYLSCQFFQNCYETY |
| 164 | PD032 | GWCLFSDMWLGLCSA |
| 165 | PD033 | EFCARDWLPYQCSSF |
| 166 | PD034 | TSYCSIEHYPCNTHH |
| 167 | PD035 | PYICSSFPLDCQAGQ |
| 168 | PD036 | VGCEWYMSSSGMCSR |
| 169 | PD037 | EVCGGCSMQSVSCWP |
| 170 | PD038 | FTECQLSPKAICMSN |
| 171 | PD039 | KYCLFSEYVEGTCLN |
| 172 | PD040 | SGCPMYAWGWDECWR |
| 173 | PD041 | VDCPWYASSSAICSR |
| 174 | PD042 | DMLLCQIRGSCAAWG |
| 175 | PD043 | ECHPYQASASLWCGY |
| 176 | PD044 | MMMGCMWSAWCPPSR |
| 177 | PD045 | NAYFRCSLMCNMIMF |
| 178 | PD046 | ACCKESVHSVHDCKR |
| 179 | PD047 | ACIGINSYMSNYCYL |
| 180 | PD048 | ANCSFLELTNKFCTI |
| 181 | PD049 | AYCSYLMFASNPCII |
| 182 | PD050 | CFTSKCPCLCYSLLA |
| 183 | PD051 | CLCRDINCWLGCSKT |
| 184 | PD052 | CWCDIYCSPYQCSSF |
| 185 | PD053 | DCIYYYQQSANLCSY |
| 186 | PD054 | DCTGVNYYIDKHCTN |
| 187 | PD055 | DECHGYLRSSGLCGG |
| 188 | PD056 | DICSAYAASSGFCYY |
| 189 | PD057 | DIICVLTPTAWCGRT |
| 190 | PD058 | DNCCMYCSWWIACRD |
| 191 | PD059 | DSCQWYMLSADLCGT |
| 192 | PD060 | DSVCFSSSSFLCHKS |
| 193 | PD061 | DTMCAIWWTVCSGGR |
| 194 | PD062 | ECTYQTSSFHEACMS |
| 195 | PD063 | EGCNLYERSSYGCNN |
| 196 | PD064 | EGCTAFAMSAGICGG |

TABLE 16-continued

Amino Acid Sequences

| SEQ ID NO. | DESCRIPTION | SEQUENCE |
|---|---|---|
| 197 | PD065 | EQSCSLTPIAFCWSE |
| 198 | PD066 | EWCNAYISSSKLCST |
| 199 | PD067 | FEVCYMFASACRNGM |
| 200 | PD068 | FSCSWYAESSSLCDI |
| 201 | PD069 | FVCQMFEASSGLCGG |
| 202 | PD070 | FYCPCCMFASSCGSR |
| 203 | PD071 | FYCSYLPGASHQCSH |
| 204 | PD072 | FYCSYLYMCEVCCYE |
| 205 | PD073 | GFCTQHTVLTWCPTS |
| 206 | PD074 | GSCPSYAVSAGLCYA |
| 207 | PD075 | GSQCFLTPTAFCTHT |
| 208 | PD076 | GTCHPYMQSSKICNN |
| 209 | PD077 | GVECFVFTGGCGGYG |
| 210 | PD078 | HELCNGHWVPCCWAY |
| 211 | PD079 | ICDSYYAVSSGLCLL |
| 212 | PD080 | IGCAWYVSSAGWCSP |
| 213 | PD081 | INLCWMFASECGEHH |
| 214 | PD082 | KCWLAEMTNLEHCNM |
| 215 | PD083 | KHCSDFAYSSRLCDR |
| 216 | PD084 | KVCSSYASSSGLCGW |
| 217 | PD085 | LDSCYMFASYCVQAV |
| 218 | PD086 | LLACHPIFVTVCQTR |
| 219 | PD087 | LLSCPYNPEHVCHTS |
| 220 | PD088 | LMCSLYALSSNLCGR |
| 221 | PD089 | LMWCVLFLWSWCCRI |
| 222 | PD090 | LPICHLTPTAVCTHI |
| 223 | PD091 | LSNMCLAFGSCLYAW |
| 224 | PD092 | LSRCHPIWYTICQNP |
| 225 | PD093 | LTQCMSVHKECGGYE |
| 226 | PD094 | LVNCRIWSWVCEEAT |
| 227 | PD095 | LYCSWYQMSSAVCKE |
| 228 | PD096 | MECGWYALSARFCEV |
| 229 | PD097 | MTCSPYAMSAHFCNE |
| 230 | PD098 | MVCSLYAYSASLCGA |
| 231 | PD099 | NALCWSTFSWWCDMD |
| 232 | PD-100 | NFTCMLTPKAYCVQT |
| 233 | PD-101 | NGACIFTLSWCTNKT |
| 234 | PD-102 | NGCELYAAASGLCRT |
| 235 | PD-103 | NIECSVFGRCCCDNY |
| 236 | PD-104 | PACRPMFWNRSCDNI |
| 237 | PD-105 | PCRVSNMFFPYNCLD |
| 238 | PD-106 | PIMCMLLPESYCWIW |
| 239 | PD-107 | PQSCYMFASLCMPNG |
| 240 | PD-108 | PRCPQGLPLYQCSSF |
| 241 | PD-109 | PSVECLVFKRCYALP |
| 242 | PD-110 | PVCQRSATIYNCNWF |
| 243 | PD-111 | QCAAYYISSFGGCSN |
| 244 | PD-112 | QFGCFMLARDFCGTY |
| 245 | PD-113 | QMMCPYNPEHKCHQK |
| 246 | PD-114 | QRECWMFASSCNSKN |
| 247 | PD-115 | QSNMCTTYICSSFNY |
| 248 | PD-116 | QSRCHSLAPYLCSSF |
| 249 | PD-117 | RAYCSLLFADSCNNN |
| 250 | PD-118 | RCIGINQYIDSNCYN |
| 251 | PD-119 | RLSCFMFASQCALEF |
| 252 | PD-120 | RQCIILMNHRQCFFK |
| 253 | PD-121 | RSCTPYMMSSSLCNT |
| 254 | PD-122 | RYCHYWKMPYECSSF |
| 255 | PD-123 | SCVSLSWFDMLKCYE |
| 256 | PD-124 | SDNCEIWWTVCSAAM |
| 257 | PD-125 | SFCWSYLVSSGLCGV |
| 258 | PD-126 | SMCMNNYGTTIIVICGN |
| 259 | PD-127 | SMVGCGWSTFCPSRG |
| 260 | PD-128 | SSLHCANGHTCPFCL |
| 261 | PD-129 | SVCSYYEESSGICSP |
| 262 | PD-130 | SWCGWYAASSGVCAL |
| 263 | PD-131 | TCISQTIDSYLNCVN |
| 264 | PD-132 | TFCNLYTKSSNICMS |
| 265 | PD-133 | TYCVFHEYLDNTCNN |
| 266 | PD-134 | VATGCPNLMLCGSWP |
| 267 | PD-135 | VEYCSLLLGNRCDYW |
| 268 | PD-136 | VGCNMYLMSAGLCVD |
| 269 | PD-137 | VLYCSWDSGTCVGSH |
| 270 | PD-138 | VMFSCYYLETCAPGV |
| 271 | PD-139 | VRIGLCPESCLVSGF |

TABLE 16-continued

Amino Acid Sequences

| SEQ ID NO. | DESCRIPTION | SEQUENCE |
|---|---|---|
| 272 | PD-140 | VTCTYYATSSSLCNT |
| 273 | PD-141 | VTGCILLPKAWCWGD |
| 274 | PD-142 | VWCSIYEYSSNLCSR |
| 275 | PD-143 | WMLECQYNNTCNNMT |
| 276 | PD-144 | WPCSPLEYYNNICNV |
| 277 | PD-145 | WTYDCHLNQTCPTYY |
| 278 | PD-146 | YCSINMYLIGGNCMY |
| 279 | PD-147 | YFCSLYANSAGFCGG |
| 280 | PD-148 | YVSCYMFSSSCPSTW |
| 281 | CX-188 LC | QGQSGQGTSYCSIEHYPCNTHHGGGSSGGSISSGLLSGRSDNPGGGSDIQLTQSPSSLSASVGDRVTITCRASESVDAYGISFMNWFQQKPGKAPKLLIYAASNQGSGVPSRFSGSGSGTDFTLTISSMQPEDFATYYCQQSKDVPWTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 282 | CX-188 HC | EVQLVESGGGLVQPGGSLRLSCAASGFTFSGYAMSWVRQAPGKGLEWVAYISNSGGNAHYADSVKGRFTISRDNSKNTLYLQMNSLRAEDTAVYYCTREDYGTSPFVYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG |
| 283 | VL CDRL1-PDL1 | RASQSISSYLN |
| 284 | CDRL2 | AASSLQS |
| 285 | CDRL3 | DNGYPST |
| 286 | CDRH1 | SYAMS |
| 287 | CDRH2 | SSIWRNGIVTVYADS |
| 288 | CDRH3 | WSAAFDY |
| 289 | MM-PDL1 | YCEVSELFVLPWCMG |
| 290 | MM | SCLMHPHYAHDYCYV |
| 291 | MM | LCEVLMLLQHPWCMG |
| 292 | MM | IACRHFMEQLPFCHH |
| 293 | MM | FGPRCGEASTCVPYE |
| 294 | MM | ILYCDSWGAGCLTRP |
| 295 | MM | GIALCPSHFCQLPQT |
| 296 | MM | DGPRCFVSGECSPIG |
| 297 | MM | LCYKLDYDDRSYCHI |
| 298 | MM | PCHPHPYDARPYCNV |
| 299 | MM | PCYWHPFFAYRYCNT |
| 300 | MM | VCYYMDWLGRNWCSS |
| 301 | MM | LCDLFKLREFPYCMG |
| 302 | MM | YLPCHFVPIGACNNK |
| 303 | MM | IFCHMGVVVPQCANY |
| 304 | MM | ACHPHPYDARPYCNV |
| 305 | MM | PCHPAPYDARPYCNV |
| 306 | MM | PCHPHAYDARPYCNV |
| 307 | MM | PCHPHPADARPYCNV |
| 308 | MM | PCHPHPYAARPYCNV |
| 309 | MM | PCHPHPYDAAPYCNV |
| 310 | MM | PCHPHPYDARPACNV |
| 311 | MM | PCHPHPYDARPYCAV |
| 312 | MM | PCHAHPYDARPYCNV |
| 313 | MM | PCHPHPYDARAYCNV |
| 314 | Light Chain CX-072 | QGQSGSGIALCPSHFCQLPQTGGGSSGGSGGSGGISSGLLSGRSDNHGGSDIQMTQSPSSLSASVGDRVTITCRASQSISSYLNWYQQKPGKAPKLLIYAASSLQSGVPSRFSGSGSGTDFTLTISSLQPEDFATYYCQQDNGYPSTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 315 | Heavy Chain CX-072 (+IgG4 S228P) | EVQLLESGGGLVQPGGSLRLSCAASGFTFSSYAMSWVRQAPGKGLEWVSSIWRNGIVTVYADSVKGRFTISRDNSKNTLYLQMNSLRAEDTAVYYCAKWSAAFDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG |

ASPECTS OF THE INVENTION

The following are non-limiting aspects of the invention described herein:

1. A process for producing a purified composition of intact activatable antibody, the process comprising:
   (a) loading an aqueous feedstock comprising water, an intact activatable antibody, a clipped impurity, and a first salt onto a chromatography column,
      wherein the chromatography column comprises a stationary phase that comprises a support matrix and ligands bound thereto,
         wherein the ligands comprise a hydrophobic substituent, and
      wherein the intact activatable antibody comprises (i) at least a first antigen binding domain (AB) that has a specific binding affinity for a first biological target, and (ii) a first prodomain,
      wherein the at least first AB comprises a first antibody light variable domain (VL) and a first antibody heavy variable domain (VH),
      wherein the first prodomain comprises a first masking moiety (MM) and a first cleavable moiety (CM), and
      wherein the first AB is coupled to the first prodomain; and
   (b) eluting the chromatography column with an eluent comprising water and a second salt to generate an eluate that comprises a purified composition comprising intact activatable antibody,
      wherein the eluate is substantially depleted of the clipped impurity.

2. The process of aspect 1, wherein the elution step (b) is carried out under isocratic conditions.

3. The process of any of aspects 1-2, wherein after step (b), the process further comprises a column cleaning step that comprises washing the chromatography column with a cleaning agent, and wherein the process does not comprise a step of eluting bound clipped impurity prior to the cleaning step.

4. The process of any of aspects 1-3, wherein the first salt and the second salt each independently comprise an anion selected from the group consisting of $PO_4^{3-}$, $SO_4^{2-}$, $OH^-$, $HPO_4^{2-}$, $CH_3COO^-$, citrate ion, an amino acid anion, $F^-$, $Cl^-$, $Br^-$, $H_2PO_4^-$, $I^-$, $NO_3^-$, $ClO_4^-$, and $SCN^-$.

5. The process of any of aspects 1-4, wherein the first and second salts each independently comprise a cation selected from the group consisting of $N(CH_3)_4^+$, $NH_4^+$, $Cs^+$, $Rb^+$, $K^+$, $Na^+$, $H^+$, $Ca^+$, $Mg^{2+}$, $Al^{3+}$, and an amino acid cation.

6. The process of any of aspects 1-5, wherein the ligands comprise one or more hydrophobic substituents selected from the group consisting of a straight chain alkyl substituent, a branched alkyl substituent, and an aryl substituent.

7. The process of any of aspects 1-6, wherein the ligands comprise a $C_4$ to $C_{10}$ alkyl substituent.

8. The process of any of aspects 1-7, wherein the ligands comprise a branched alkyl substituent.

9. The process of any of aspects 1-8, wherein the ligands comprise an aryl substituent.

10. The process of aspect 9, wherein the aryl substituent is phenyl.

11. The process of any of aspects 1-10, wherein the stationary phase is a hydrophobic interaction chromatography (HIC) stationary phase.

12. The process of aspect 11, wherein the first salt and the second salt each independently comprise an anion selected from the group consisting of $PO_4^{3-}$, $SO_4^{2-}$, $OH^-$, $HPO_4^{2-}$, $F^-$, $CH_3COO^-$, citrate ion, an amino acid anion, and $Cl^-$.

13. The process of any of aspects 11-12, wherein the first salt and second salt each independently comprise an anion selected from the group consisting of $PO_4^{3-}$, $SO_4^{2-}$, and $HPO_4^{2-}$.

14. The process of any of aspects 11-13, wherein the first and second salt each independently comprise a cation selected from the group consisting of $N(CH_3)_4^+$, $NH_4^+$, $Cs^+$, $Rb^+$, $K^+$, $Na^+$, $H^+$, $Ca^+$, $Mg^{2+}$, $Al^{3+}$, and an amino acid cation.

15. The process of any of aspects 11-14, wherein the first and second salt each independently comprise a cation selected from the group consisting of $NH_4^+$, $K^+$, $Na^+$, $Li^+$, and $Mg^{2+}$.

16. The process of any of aspects 11-15, wherein the first and second salt each independently comprise a cation selected from the group consisting of $NH_{4+}$, $K^+$, and $Na^+$.

17. The process of any of aspects 11-16, wherein the first and second salt each independently comprise a cation selected from the group consisting of $NH_4^+$, $K^+$, and $Na^+$ and an anion selected from the group consisting of $PO_4^{3-}$, $SO_4^{2-}$, $OH^-$, $HPO_4^{2-}$, $CH_3COO^-$, citrate ion, $F^-$, $Cl^-$, $Br^-$, $H_2PO_4^-$, $I^-$, $NO_3^-$, $ClO_4^-$, and $SCN^-$.

18. The process of any of aspects 11-17, wherein the first and second salt are each independently selected from the group consisting of $(NH_4)_2SO_4$, $Na_2SO_4$, $Na_3PO_4$, $K_3PO_4$, NaCl, KCl, and $CH_3COONH_4$.

19. The process of any of aspects 11-18, wherein the first and second salt are each independently selected from the group consisting of $(NH_4)_2SO_4$, $Na_2SO_4$, $Na_3PO_4$, and $K_3PO_4$.

20. The process of any of aspects 11-19, wherein the first and second salt are each independently selected from the group consisting of $(NH_4)_2SO_4$ and $Na_2SO_4$, 21. The process of any of aspects 11-20, wherein the first salt and the second salt are the same salt.

22. The process of any of aspects 11-20, wherein the first salt and the second salt are different salts.

23. The process of any of aspects 11-22, wherein the aqueous feedstock and eluent comprise a first salt concentration and a second salt concentration, respectively, and wherein the first salt concentration is greater than the second salt concentration.

24. The process of any of aspects 1-10, wherein the stationary phase is a multimodal chromatography (MMC) stationary phase, whereby the ligands further comprise at least one further substituent that facilitates separation on the basis of an interaction other than hydrophobicity.

25. The process of aspect 24, wherein the at least one further substituent facilitates separation on the basis of an interaction selected from the group consisting of electrostatic, hydrogen bonding, and thiophilicity.

26. The process of any of aspects 24-25, wherein the at least one further substituent is selected from the group consisting of a sulfide substituent, a carboxyl substituent, and an amine substituent.

27. The process of any of aspects 24-26, wherein the at least one further substituent comprises a carboxyl substituent.

28. The process of any of aspects 24-27, wherein the at least one further substituent comprises an amine substituent.

29. The process of any of aspects 24-28, wherein the at least one further substituent comprises a sulfide substituent.

30. The process of any of aspects 24-29, wherein the first salt and the second salt each independently comprise an anion selected from the group consisting of $Cl^-$, $Br^-$, $H_2PO_4$, $I^-$, $NO_3^-$, an amino acid anion, $ClO_4^-$, and $SCN^-$.

31. The process of any of aspects 24-30, wherein the first and second salt each independently comprise a cation selected from the group consisting of $N(CH_3)_4^+$, $NH_4^+$, $Ba^+$, $Ca^{2+}$, $Mg^{2+}$, $Cs^+$, $Rb^+$, $K^+$, $Na^+$, and an amino acid cation.

32. The process of any of aspects 24-31, wherein at least one of the first and second salt is an amino acid cation.

33. The process of aspect 32, wherein the amino acid cation is an arginine cation.

34. The process of any of aspects 24-33, wherein the first salt and the second salt are the same.

35. The process of any of aspects 24-33, wherein the first salt and the second salt are different.

36. The process of any of aspects 24-31, wherein the first salt is comprises an Na+ cation and the second salt comprises both an Na+ cation and an arginine cation.

37. The process of any of aspects 24-36, wherein the aqueous feedstock and eluate comprise a first salt concentration and a second salt concentration, respectively, and wherein the second salt concentration is greater than the first salt concentration.

38. The process of aspect 37, wherein the second salt concentration is at least 2 times greater than the first salt concentration.

39. The process of aspect 37, wherein the second salt concentration is at least 3 times greater than the first salt concentration.

40. The process of aspect 36 or 37, wherein the concentration of Na+ cation in the second salt is the same as the concentration of Na+ cation in the first salt, and wherein the second salt further comprises an arginine cation not present in the first salt.

41. The process of any of aspects 11-20, wherein the first and second salt are the same, and are selected from the group consisting of $(NH_4)_2SO_4$ and $Na_2SO_4$.

42. The process of aspect 23 or 41, wherein the first salt concentration is at least 2 times greater than the second salt concentration.

43. The process of aspect 23 or 41, wherein the first salt concentration is at least 3 times greater than the second salt concentration.

44. The process of any of aspects 1-43, wherein the aqueous feedstock comprises a pH in the range of from about 5.0 to about 8.0, or about 5.0 to about 7.5, or from about 5.0 to about 7.0, or from about 5.5 to about 6.5.

45. The process of any of aspects 1-44, wherein the pH of the aqueous feedstock is greater than the pH of the eluent.

46. The process of any of aspects 1-44, wherein the pH of the aqueous feedstock is lower than the pH of the eluent.

47. The process of any of aspects 1-44, wherein the pH of the aqueous feedstock is about the same as the pH of the eluent.

48. The process of aspect 47, wherein the pH of the aqueous feedstock and the pH of the eluent is about 5.5 to about 6.5.

49. The process of aspect 47, wherein the pH of the aqueous feedstock and the pH of the eluent is about 5.8 to about 6.2.

50. The process of aspect 11, wherein the first and second salt are individually selected from the group consisting of $(NH_4)_2SO_4$ and $Na_2SO_4$, and wherein the pH of the aqueous feedstock and the pH of the eluent is about 5.5 to about 6.5.

51. The process of aspect 50, wherein the first salt concentration is about 1.0 to 2.0 M, and wherein the second salt concentration is about 0.2 to about 0.6 M.

52. The process of aspect 50, wherein the first salt concentration is at least two times, at least three times greater, at least four times greater, or at least five times greater than the second salt concentration.

53. The process of aspect 24, wherein the first salt is NaCl and the second salt is NaCl and arginine HCl, and wherein the pH of the he aqueous feedstock and the pH of the eluent is about 5.5 to about 6.5.

54. The process of aspect 53, wherein the first salt concentration is about 30 mM NaCl and the second salt concentration is about 30 mM NaCl and about 90 mM arginine HCl.

55. The process of aspect 53, wherein the second salt concentration is at least two times, at least three times greater, at least four times greater, or at least five times greater than the first salt concentration.

56. The process of any of aspects 1-55, wherein steps (a) and (b) are carried out at a temperature in the range of from about 3° C. to about 40° C., or in the range of from about 10° C. to about 30° C., or in the range of from about 15° C. to about 30° C., or in the range of about 22° C.+/−4° C.

57. The process of aspect 56, wherein steps (a) and (b) are carried about at a temperature of 22° C.+/−4° C.

58. The process of any of aspects 1-57, wherein the process results in a total protein yield of at least about 70%, or at least about 71%, or at least about 72%, or at least about 73%, or at least about 74%, or at least about 75%, or at least about 76%, or at last about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, as determined by absorbance at a wavelength of 280 nm.

59. The process of any of aspects 1-58, wherein the ratio of quantity of clipped impurity in the aqueous feedstock to quantity of clipped impurity in the eluate on a percent clipped impurity basis is at least about 2, or at least about 3, or at least about 4, or at least about 5, or at least about 6, or at least about 7, or at least about 8, or at least about 9, or at least about 10, or at least about 15, or at least about 20, as determined by reducing SDS-cGE.

60. The process of any of aspects 1-59, wherein the eluate comprises less than about less than about 15%, or less than about 14%, or less than about 13%, or less than about 12%, or less than about 11%, or less than about 10%, or less than about 10%, or less than about 9%, or less than about 8%, or less than about 7%, or less than about 6% of the relative quantity of clipped impurity present in the aqueous feedstock, as determined by reducing SDS-cGE.

61. The process of aspect 60, wherein the eluate comprises less than about 5%, or less than about 4%, or less than about 3%, or less than about 2%, or less than about 1%, or less than about 0.9%, or less than about 0.8%, or less than about 0.7%, or less than about 0.6%, or less than about 0.5% clipped impurity, as determined by reducing SDS-cGE.

62. The process of aspect 61, wherein the eluate comprises less than about 2%, or less than about 1%, or less than about 0.9%, or less than about 0.8%, or less than about 0.7%, or less than about 0.6%, or less than about 0.5% clipped impurity, as determined by reducing SDS-cGE.

63. The process of any of aspects 1-62, wherein the eluate comprises a relative quantity of clipped impurity in the range of from about 0.1% to about 15% clipped impurity, or from about 0.1% to about 10% clipped impurity, or from about 0.1% to about 10% clipped impurity, or from about 0.1% to about 5% clipped impurity, or from about 0.1% to about 4% clipped impurity, or from about 0.1% to about 3% clipped impurity, or from about 0.1% to about 2% clipped impurity, or from about 0.1% to about 1% clipped impurity, as determined by reducing SDS-cGE.

64. The process of any of aspects 1-62, wherein the eluate comprises no detectable clipped impurity, as determined by reducing SDS-cGE.

65. The process of any of aspects 1-64, wherein the aqueous feedstock and the eluate each independently comprises a buffer selected from the group consisting of MES, MOPS, or HEPES.

66. The process of any of aspects 59-64, wherein the first AB comprises an antibody light chain and an antibody heavy chain, and wherein first prodomain is coupled to the antibody light chain of the first AB via a peptide bond, and wherein the relative quantity of clipped impurity is determined based on the light chain clipped variant and light chain of the intact activatable antibody as determined by reducing SDS-cGE.

67. The process of any of aspects 1-64, wherein the first prodomain is coupled to the first AB via a peptide bond.

68. The process of any of aspects 1-67, wherein the aqueous feedstock further comprises an impurity selected from the group consisting of host cell protein (HCP) and high molecular weight species (HMWS).

69. The process of aspect 68, wherein the aqueous feedstock further comprises HCP.

70. The process of aspect 69, wherein the ratio of the quantity of HCP in the aqueous feedstock to the quantity of HCP in the eluate on a ppm basis is at least about 2, or at least about 3, or at least about 4, or at least about 5, or at least about 6, or at least about 7, or at least about 8, or at least about 9, or at least about 10, as determined by a corresponding HCP ELISA assay.

71. The process of any of aspects 69-70, wherein the eluate comprises less than about 150 ppm, or less than about 140 ppm, or less than about 130 ppm, or less than about 120 ppm, or less than about 110 ppm, or less than about 100 ppm, or less than about 90 ppm, or less than about 80 ppm, or less than about 70 ppm, or less than about 60 ppm, or less than about 50 ppm, or less than about 45 ppm, or less than about 40 ppm, or less than about 35 ppm, or less than about 30 ppm, or less than about 25 ppm, or less than about 20 ppm, or less than about 15 ppm, or less than about 10 ppm HCP, or less than about 5 ppm HCP, or less than about 1 ppm HCP, as measured by a corresponding HCP ELISA.

72. The process of any of aspects 69-70, wherein the eluate comprises a quantity of HCP in the range of from about 0.5 ppm HCP to about 150 ppm HCP, or from about 0.5 ppm HCP to about 140 ppm HCP, or 0.5 ppm HCP to about 130 ppm HCP, or from about 0.5 ppm HCP to about 120 ppm, or from about 0.5 ppm HCP to about 110 ppm, or from about 0.5 ppm HCP to about 100 ppm HCP, or from about 0.5 ppm HCP to about 90 ppm HCP, or from about 0.5 ppm HCP to about 90 ppm HCP, or from about 0.5 ppm HCP to about 80 ppm HCP, or from about 0.5 ppm HCP to about 70 ppm HCP, or from about 0.5 ppm HCP to about 60 ppm HCP, or from about 0.5 ppm to about 50 ppm HCP, or from about 0.5 ppm HCP to about 45 ppm HCP, or from about 0.5 ppm HCP to about 40 ppm HCP, or from about 0.5 ppm HCP to about 40 ppm HCP, or from about 0.5 ppm HCP to about 35 ppm HCP, or from about 0.5 ppm HCP to about 30 ppm HCP, or from about 1 ppm HCP to about 25 ppm HCP, or from about 1 ppm HCP to about 20 ppm HCP, or from about 0.5 ppm HCP to about 15 ppm HCP, or from about 0.5 ppm HCP to about 10 ppm HCP.

73. The process of any of aspects 69-70, wherein the eluate comprises no detectable HCP, as measured by a corresponding HCP ELISA assay.

74. The process of any of aspects 1-73, wherein the aqueous feedstock further comprises HMWS.

75. The process of aspect 74, wherein the ratio of the quantity of HMWS in the aqueous feedstock to the quantity of HMWS in the eluate on a percent peak area basis is at least about 2, or at least about 3, or at least about 4, or at least about 5, as measured by Size Exclusion (SE)-HPLC.

76. The process of any of aspects 74-75, wherein the eluate comprises less than about 5% HMWS, or less than about 4% HMWS, or less than about 3% HMWS, or less than about 2% HMWS, or less than about 1% HMWS, as measured by SE-HPLC.

77. The process of any of aspects 74-75, wherein the eluate comprises a quantity of HMWS in the range of from about 0.2% HMWS to about 5% HMWS, or from about 0.2% HMWS to about 4% HMWS, or from about 0.2% HMWS to about 3% HMWS, or from about 0.2% HMWS to about 2% HMWS, or from about 0.2% HMWS to about 1% HMWS, as determined by SE-HPLC.

78. The process of any of aspects 74-75, wherein the eluate comprises no detectable HMWS, as measured by SE-HPLC.

79. The process of any of aspects 1-78, wherein the eluate comprises at least about 90% intact activatable antibody, or at least about 91%, or at least about 92%, or at least about 93%, or at least about 94%, or at least about 95% intact activatable antibody, as determined by reducing SDS-cGE.

80. The process of aspect 79, wherein the first AB comprises an antibody light chain and an antibody heavy chain, and wherein first prodomain is coupled to the antibody light chain of the first AB via a peptide bond, and wherein the percent intact activatable antibody is determined based on the light chain of the intact activatable antibody and light chain clipped variant as determined by reducing SDS-cGE.

81. The process of any of aspects 1-80, wherein prior to step (a), the process further comprises:
(a°) subjecting a bioharvest composition comprising the intact activatable antibody and the clipped impurity to one or more intervening unit operations selected from the group consisting of a centrifugation step, a filtration step, an affinity chromatography step, a virus inactivation step, a size exclusion chromatography step, a virus filtration step, an ion exchange chromatography step, and a combination of any two or more thereof, to produce one or more bulk intermediate product compositions, wherein the aqueous feedstock comprises at least one bulk intermediate product composition.

82. The process of any of aspects 1-81, wherein the eluate is subjected to one or more downstream unit operations to generate a downstream product composition.

83. The process of aspect 82, wherein the one or more downstream unit operations is selected from the group consisting of a further purification process, a chemical synthesis process, a dilution process, a solvent exchange process, a formulating process, a lyophilization process, and any combination of two or more thereof.

84. The process of aspect 82 or 83, wherein the one or more downstream unit operations comprises a further purification process selected from the group consisting of a centrifugation step, a filtration step, an affinity chromatography step, a virus inactivation step, a size exclusion chromatography step, a virus filtration step, an ion exchange chromatography step, and any combination of two or more thereof.

85. The process of any of aspects 82-84, wherein the one or more downstream unit operations comprises a lyophilization process.

86. The process of any of aspects 82-85, wherein the one or more downstream unit operations is a chemical synthesis process.

87. The process of aspect 86, wherein the chemical synthesis process is a chemical conjugation reaction.

88. The process of any of aspects 1-87, wherein the aqueous feedstock comprises greater than about 0.5% clipped impurity, or greater than about 0.6%, or greater than about 0.7%, or greater than about 0.8%, or greater than about 0.9%, or greater than about 1%, or greater than about 1.5%, or greater than about 2%, or greater than about 2.5%, or greater than about 3%, or greater than about 3.5%, or greater than about 4%, or greater than about 4.5% clipped impurity, as determined by reducing SDS-cGE.

89. The process of any of aspects 1-88, wherein the intact activatable antibody comprises a second AB and a second prodomain, and wherein the clipped impurity comprises single-arm clipped impurity, as determined by mass spectrometry.

90. The process of aspect 89, wherein the second AB is the same as the first AB, and
wherein the second prodomain is the same as the first prodomain.

91. The process of aspect 89 or 90, wherein the clipped impurity consists essentially of single-arm clipped impurity, as determined by mass spectrometry.

92. The process of aspect 89 or 90, wherein the clipped impurity consists of single-arm clipped impurity, as determined by mass spectrometry.

93. A purified intact activatable antibody composition produced by the process of any of aspects 1-92.

94. A purified product composition comprising the downstream product composition of any of aspects 82-87.

95. The process of any of aspects 1-92, wherein the eluate comprises at least about 90% intact activatable antibody, as determined by reducing SDS-cGE, less than about 15% clipped impurity, as determined by reducing SDS-cGE, less than about 5% HMWS, as determined by SE-HPLC, and less than about 150 ppm HCP, as determined by a corresponding HCP ELISA.

96. The process of aspect 95, wherein the eluate comprises less than about 5% clipped impurity, as determined by reducing SDS-cGE.

97. The process of aspect 96, wherein the eluate comprises less than about 3% clipped impurity, as determined by reducing SDS-cGE.

98. A purified intact activatable antibody composition comprising the eluate produced by the process of any of aspects 1-97.

99. A purified intact activatable antibody composition comprising at least about 90% intact activatable antibody, as determined by reducing SDS-cGE, less than about 15% clipped impurity, as determined by reducing SDS-cGE, less than about 5% HMWS, as determined by SE-HPLC, and less than about 150 ppm HCP, as determined by a corresponding HCP ELISA.

100. The purified intact activatable antibody composition of aspect 98 or 99, wherein the composition comprises less than about 14% clipped impurity, or less than about 13% clipped impurity, or less than about 12% clipped impurity, or less than about 12% clipped impurity, or less than about 11% clipped impurity, or less than about 10% clipped impurity, or less than about 9% clipped impurity, or less than about 8% clipped impurity, or less than about 7% clipped impurity, or less than about 6% clipped impurity, as determined by reducing SDS-cGE.

101. The purified intact activatable antibody composition of any of aspects 98-100, wherein the composition comprises less than about 5% clipped impurity, or less than about 4% clipped impurity, or less than about 3% clipped impurity, or less than about 2% clipped impurity, as determined by reducing SDS-cGE.

102. The purified intact activatable antibody composition of any of aspects 98-101, wherein the composition comprises less than about 1% clipped impurity, or less than about 0.9% clipped impurity, or less than about 0.8% clipped impurity, or less than about 0.7% clipped impurity, or less than about 0.6% clipped impurity, or less than about 0.5% clipped impurity, as determined by reducing SDS-cGE.

103. The purified intact activatable antibody composition of aspect 98 or 99, wherein the composition comprises a relative quantity of clipped impurity in the range of from about 0.1% to about 15% clipped impurity, or from about 0.1% to about 10% clipped impurity, or from about 0.1% to about 10% clipped impurity, or from about 0.1% to about 5% clipped impurity, or from about 0.1% to about 4% clipped impurity, or from about 0.1% to about 3% clipped impurity, or from about 0.1% to about 2% clipped impurity, or from about 0.1% to about 1% clipped impurity, as determined by reducing SDS-cGE.

104. The purified intact activatable antibody composition of aspect 98 or 99, wherein the composition comprises no detectable clipped impurity, as determined by reducing SDS-cGE.

105. The purified intact activatable antibody composition of any of aspects 98-104, wherein the composition comprises less than about 140 ppm HCP, or less than about 130 ppm HCP, or less than about 120 ppm HCP, or less than about 110 ppm HCP, or less than about 100 ppm HCP, or less than about 90 ppm HCP, or less than about 80 ppm HCP, or less than about 70 ppm HCP, or less than about 60 ppm HCP, or less than about 50 ppm HCP, or less than about 45 ppm HCP, or less than about 40 ppm HCP, or less than about 35 ppm HCP, or less than about 30 ppm HCP, or less than about 25 ppm HCP, or less than about 20 ppm HCP, or less than about 15 ppm HCP, or less than about 10 ppm HCP, as determined by a corresponding HCP ELISA assay.

106. The purified intact activatable antibody composition of any of aspects 98-105, wherein the composition comprises a quantity of HCP in the range of from about 1 ppm HCP to about 150 ppm HCP, or from about 1 ppm HCP to about 140 ppm HCP, or 1 ppm HCP to about 130 ppm HCP, or from about 1 ppm HCP to about 120 ppm, or from about 1 ppm HCP to about 110 ppm, or from about 1 ppm HCP to about 100 ppm HCP, or from about 1 ppm HCP to about 90 ppm HCP, or from about 1 ppm HCP to about 90 ppm HCP, or from about 1 ppm HCP to about 80 ppm HCP, or from about 1 ppm HCP to about 70 ppm HCP, or from about 1 ppm HCP to about 60 ppm HCP, or from about 1 ppm to about 50 ppm HCP, or from about 1 ppm HCP to about 45 ppm HCP, or from about 1 ppm HCP to about 40 ppm HCP, or from about 1 ppm HCP to about 40 ppm HCP, or from about 1 ppm HCP to about 35 ppm HCP, or from about 1 ppm HCP to about 30 ppm HCP, or from about 1 ppm HCP to about 25 ppm HCP, or from about 1 ppm HCP to about 20 ppm HCP, or from about 1 ppm HCP to about 15 ppm HCP, or from about 1 ppm HCP to about 10 ppm HCP.

107. The purified intact activatable antibody composition of any of aspects 98-106, wherein the composition comprises less than about 4% HMWS, or less than about 3% HMWS, or less than about 2% HMWS, or less than about 1% HMWS, as determined by SE-HPLC.

108. The purified intact activatable antibody composition of aspect 98 or 99, wherein the composition comprises a quantity of HMWS in the range of from about 0.2% HMWS to about 5% HMWS, or from about 0.2% HMWS to about 4% HMWS, or from about 0.2% HMWS to about 3% HMWS, or from about 0.2% HMWS to about 2% HMWS, or from about 0.2% HMWS to about 1% HMWS, as determined by SE-HPLC 109. The purified intact activatable antibody composition of any of aspects 98-108, wherein the composition comprises at least about 91%, or at least about 92%, or at least about 93%, or at least about 94%, or at least about 95% intact activatable antibody, as determined by reducing SDS-cGE.

110. The purified intact activatable antibody composition of any of aspects 98-109, wherein the composition is lyophilized.

111. A pharmaceutically acceptable composition comprising the composition of any of aspects 98-110 and a pharmaceutically acceptable excipient.

112. The process of any of aspects 1-92, or 95-97, the purified intact activatable antibody composition of any of aspects 93, or 98-110, the purified product composition of aspect 94, or the pharmaceutically acceptable composition of aspect 111, wherein the first CM in the intact activatable antibody comprises a substrate for a protease that is overexpressed in a diseased tissue relative to healthy tissue.

113. The process of any of aspects 1-92, 95-97, or 112, the purified intact activatable antibody composition of any of aspects 93, 98-110, the purified product composition of any of aspects 94 or 112, or the pharmaceutically acceptable composition of any of aspects 110 or 111, wherein the intact activatable antibody further comprises (iii) a second AB that has a specific binding affinity for a second biological target, and (iv) a second prodomain,
  wherein the second AB comprises a second VL, and a second VH,
  wherein the second prodomain comprises a second MM and a second CM, and
  wherein the second AB is coupled to the second prodomain.

114. The process, purified intact activatable antibody composition, purified product composition, or pharmaceutically acceptable composition of aspect 113, wherein the second CM comprises a substrate for a protease that is overexpressed in a diseased tissue relative to healthy tissue.

115. The process, purified intact activatable antibody composition, purified product composition, or pharmaceutically acceptable composition of any of aspects 113-114, wherein the first CM and the second CM comprise identical amino acid sequences.

116. The process, purified intact activatable antibody composition, purified product composition, or pharmaceutically acceptable composition of any of aspects 113-115, wherein the first CM and the second CM comprise different amino acid sequences.

117. The process, purified intact activatable antibody composition, purified product composition, or pharmaceutically acceptable composition of any of aspects 113-116, wherein the first biological target and the second biological target are different.

118. The process, purified intact activatable antibody composition, purified product composition, or pharmaceutically acceptable composition of any of aspects 113-117, wherein at least one of the first biological target and the second biological target is a T cell co-receptor.

119. The process, purified intact activatable antibody composition, purified product composition, or pharmaceutically acceptable composition of aspect 118, wherein the T cell co-receptor is a cluster of differentiation 3 (CD3) T cell co-receptor.

120. The process, purified intact activatable antibody composition, purified product composition, or pharmaceutically acceptable composition of any of aspects 113-115, wherein the second AB is identical to the first AB, and wherein the second prodomain is identical to the first prodomain.

121. The process, purified intact activatable antibody composition, purified product composition, or pharmaceutically acceptable composition of aspect 120, wherein the first biological target and the second biological target are CD166.

122. The process, purified intact activatable antibody composition, purified product composition, or pharmaceutically acceptable composition of aspect 120, wherein the first biological target and the second biological target are PD-1.

123. The process, purified intact activatable antibody composition, purified product composition, or pharmaceutically acceptable composition of aspect 120, wherein the first biological target and the second biological target are PDL-1.

While the foregoing invention has been described in some detail for purposes of clarity and understanding, it will be clear to one skilled in the art from a reading of this disclosure that various changes in form and detail can be made without departing from the true scope of the invention. It is understood that the materials, examples, and embodiments described herein are for illustrative purposes only and not intended to be limiting and that various modifications or changes in light thereof will be suggested to persons skilled in the art and are to be included within the spirit and scope of the appended claims.

We claim:

1. A method for determining or monitoring relative amounts of an activatable antibody and a clipped variant thereof during a composition production process, the method comprising:
 a) subjecting a sample composition from each of two or more operations of an activatable antibody composition production process, wherein each sample composition comprises a population of activatable antibody and a population of clipped variants thereof, to a gel capillary electrophoresis procedure to thereby separate the population of activatable antibody from the population of clipped variants thereof in the gel capillary electrophoresis procedure, wherein the two or more operations of an activatable antibody composition production process are selected from the group consisting of a cell harvest, protein affinity chromatography, ion exchange chromatography, hydrophobic interaction chromatography, and multimodal chromatography; and
 b) quantifying the relative amounts of the population of activatable antibody and the population of clipped variants thereof in each sample composition by determining the peak area corresponding to intact prodomain-containing polypeptide and the peak area corresponding to clipped prodomain-containing polypeptide(s) thereof to thereby monitor the relative amounts of the activatable antibody and the clipped variant thereof during the composition production process,
  wherein the intact activatable antibody comprises (i) at least a first antigen binding domain (AB) that has a specific binding affinity for a first biological target, and (ii) a first prodomain,
  wherein the at least first AB comprises a first antibody light variable domain (VL) and a first antibody heavy variable domain (VH),
  wherein the first prodomain comprises a first masking moiety (MM) and a first cleavable moiety (CM),
  wherein the first AB is coupled to the first prodomain,
  wherein the clipped variant of the intact activatable antibody comprises the AB of the activatable antibody but lacks all or a portion of the MM.

2. The method of claim 1, wherein step a) further comprises contacting the activatable antibody and clipped variant thereof in the sample composition with a reducing agent.

3. The method of claim 2, wherein the reducing agent is selected from the group consisting of dithioerythritol (DTE), dithiothreitol (DTT), beta-mercaptoethanol, and any combination thereof.

4. The method of claim 1, wherein step a) further comprises contacting the activatable antibody and clipped variant thereof in the sample composition with a denaturing agent.

5. The method of claim 4, wherein the denaturing agent is sodium dodecyl sulfate (SDS).

6. A process for producing a purified composition of intact activatable antibody, the process comprising:
 (a) loading an aqueous feedstock comprising water, an intact activatable antibody, a detectable clipped impurity of the intact activatable antibody, and a first salt onto a chromatography column,
  wherein the chromatography column comprises a stationary phase that comprises a support matrix and ligands bound thereto,
   wherein the ligands comprise a hydrophobic substituent, and
  wherein the intact activatable antibody comprises (i) at least a first antigen binding domain (AB) that has a specific binding affinity for a first biological target, and (ii) a first prodomain,
   wherein the at least first AB comprises a first antibody light variable domain (VL) and a first antibody heavy variable domain (VH),
   wherein the first prodomain comprises a first masking moiety (MM) and a first cleavable moiety (CM),
   wherein the first AB is coupled to the first prodomain, and
  wherein the clipped impurity of the intact activatable antibody comprises the AB of the activatable antibody but lacks all or a portion of the MM; and
 (b) eluting the chromatography column with an eluent comprising water and a second salt to generate an eluate that comprises a purified composition comprising intact activatable antibody,
  wherein the eluting step (b) is performed such that the eluate has a relative level of clipped impurity reduced by at least 20% compared to a level of clipped impurity in the aqueous feedstock in step (a).

7. The process of claim 6, wherein the elution step (b) is carried out under isocratic conditions.

8. The process of claim 6, wherein after step (b), the process further comprises a column cleaning step that comprises washing the chromatography column with a cleaning agent, and wherein the process does not comprise a step of eluting bound clipped impurity prior to the cleaning step.

9. The process of claim 6, wherein the stationary phase is a hydrophobic interaction chromatography (HIC) stationary phase.

10. The process of claim 6, wherein the stationary phase is a multimodal chromatography (MMC) stationary phase.

11. The process of claim 6, wherein the aqueous feedstock further comprises an impurity selected from the group consisting of host-cell protein (HCP) and high molecular weight species (HMWS).

12. The process of claim 11, wherein the aqueous feedstock further comprises HCP.

13. The process of claim 12, wherein the ratio of quantity of HCP in the aqueous feedstock to the quantity of HCP in the eluate on a ppm basis is at least about 2.

14. The process of claim 12, wherein the aqueous feedstock further comprises HMWS.

15. The process of claim 14, wherein the ratio of the quantity of HMWS in the aqueous feedstock to the quantity of HMWS in the eluate on a percent peak area basis is at least about 2, as measured by size exclusion high performance liquid chromatography (SE-HPLC).

16. The process of claim 6, wherein prior to step (a), the process further comprises:

(a)⁰ subjecting a bioharvest composition comprising the intact activatable antibody and the clipped impurity to one or more intervening unit operations selected from the group consisting of a centrifugation step, a filtration step, an affinity chromatography step, a virus inactivation step, a size exclusion chromatography step, a virus filtration step, an ion exchange chromatography step, and a combination of any two or more thereof, to produce one or more bulk intermediate product compositions, wherein the aqueous feedstock comprises at least one bulk intermediate product composition.

17. The process of claim 6, wherein the eluate is subjected to one or more downstream unit operations to generate a downstream product composition.

18. The process of claim 6, wherein the aqueous feedstock comprises greater than about 1% clipped impurity, as measured by reducing SDS-cGE.

19. The process of claim 6, wherein the aqueous feedstock comprises greater than about 2% clipped impurity, as measured by reducing SDS-cGE.

20. The process of claim 6, wherein the aqueous feedstock comprises greater than about 3% clipped impurity, as measured by reducing SDS-cGE.

21. The process of claim 6, wherein the aqueous feedstock comprises greater than about 4% clipped impurity, as measured by reducing SDS-cGE.

22. The process of claim 6, wherein the process results in at least a 2-fold reduction of clipped impurity, as measured by reducing SDS-capillary gel electrophoresis.

23. The process of claim 18, wherein the process results in at least a 2-fold reduction of clipped impurity, as measured by reducing SDS-capillary gel electrophoresis.

24. The process of claim 19, wherein the process results in at least a 2-fold reduction of clipped impurity, as measured by reducing SDS-capillary gel electrophoresis.

25. The process of claim 20, wherein the process results in at least a 2-fold reduction of clipped impurity, as measured by reducing SDS-capillary gel electrophoresis.

26. The process of claim 21, wherein the process results in at least a 2-fold reduction of clipped impurity, as measured by reducing SDS-capillary gel electrophoresis.

27. The process of claim 22, wherein the process results in at least a 3-fold reduction of clipped impurity, as measured by reducing SDS-capillary gel electrophoresis.

28. The process of claim 23, wherein the process results in at least a 3-fold reduction of clipped impurity, as measured by reducing SDS-capillary gel electrophoresis.

29. The process of claim 24, wherein the process results in at least a 3-fold reduction of clipped impurity, as measured by reducing SDS-capillary gel electrophoresis.

30. The process of claim 25, wherein the process results in at least a 3-fold reduction of clipped impurity, as measured by reducing SDS-capillary gel electrophoresis.

31. The process of claim 6, wherein the aqueous feedstock comprises a pH in the range of from about 5.0 to about 7.5.

32. The process of claim 6, wherein the aqueous feedstock comprises a pH in the range of from about 5.5 to about 6.5.

33. The process of claim 6, wherein the MM can bind to the AB.

34. The process of claim 6, wherein the eluate comprises less than about 5% clipped impurity.

35. The process of claim 6, wherein the eluate comprises less than about 3% clipped impurity.

36. The process of claim 6, wherein the eluate comprises less than about 2% clipped impurity.

37. The process of claim 6, wherein the eluate comprises less than about 1% clipped impurity.

38. The process of claim 6, wherein steps (a) and (b) are carried out at a temperature in the range of from 18° C. to about 30° C. and at a pH of about 5.0 to about 8.0.

39. The process of claim 6, wherein steps (a) and (b) are carried out at a temperature in the range of from about 22° C. to about 30° C.

40. The process of claim 6, wherein the pH of the aqueous feedstock is about 5.5 to about 6.5, wherein the pH of the eluent is about 5.5 to about 6.5, and wherein steps (a) and (b) are carried out at a temperature in the range of from about 22° C. to about 28° C.

41. The process of claim 6, wherein the aqueous feedstock comprises an amount of intact activatable antibody and an amount of clipped impurity of the intact activatable antibody, and wherein steps (a) and (b) are performed such that the amount of clipped impurity in the eluate is reduced by 2-fold as determined by SDS-cGE.

42. The process of claim 6, wherein the aqueous feedstock comprises an amount of intact activatable antibody, an amount of clipped impurity of the intact activatable antibody, an amount of HCP, and an amount of HMWS, and wherein steps (a) and (b) are performed such that the amount of clipped impurity is reduced by 7- to 10-fold as determined by SDS-cGE, wherein the amount of HCP is reduced by 8- to 10-fold as determined by ELISA, wherein the amount of HMWS is reduced by 7- to 13-fold as determined by SE-HPLC in the eluate, and wherein the eluate has a yield of 75-85% of the intact activatable antibody.

43. The process of claim 6, wherein the MM binds specifically to the AB.

44. The process of claim 6, wherein the MM has less than 50 amino acids.

* * * * *